(12) United States Patent
Kondo et al.

(10) Patent No.: US 11,935,234 B2
(45) Date of Patent: Mar. 19, 2024

(54) METHOD FOR DETECTING ABNORMALITY, NON-TRANSITORY COMPUTER-READABLE RECORDING MEDIUM STORING PROGRAM FOR DETECTING ABNORMALITY, ABNORMALITY DETECTION APPARATUS, SERVER APPARATUS, AND METHOD FOR PROCESSING INFORMATION

(71) Applicant: Panasonic Corporation, Osaka (JP)

(72) Inventors: Kenji Kondo, Kyoto (JP); Jun Ozawa, Nara (JP); Hirohiko Kimura, Fukui (JP); Harumi Itoh, Fukui (JP); Masato Tanaka, Fukui (JP); Shinichi Fujimoto, Fukui (JP)

(73) Assignee: PANASONIC CORPORATION, Osaka (JP)

( * ) Notice: Subject to any disclaimer, the term of this patent is extended or adjusted under 35 U.S.C. 154(b) by 368 days.

(21) Appl. No.: 17/492,732

(22) Filed: Oct. 4, 2021

(65) Prior Publication Data

US 2022/0028072 A1 Jan. 27, 2022

Related U.S. Application Data

(63) Continuation of application No. PCT/JP2020/019397, filed on May 15, 2020.

(30) Foreign Application Priority Data

May 22, 2019 (JP) .................................. 2019-096123
Apr. 14, 2020 (JP) .................................. 2020-072407

(51) Int. Cl.
*G06T 7/13* (2017.01)
*G06T 7/00* (2017.01)
(Continued)

(52) U.S. Cl.
CPC .............. *G06T 7/0012* (2013.01); *G06T 7/13* (2017.01); *G16H 30/40* (2018.01); *G16H 50/20* (2018.01);
(Continued)

(58) Field of Classification Search
CPC .................................................... G06T 7/0012
See application file for complete search history.

(56) References Cited

U.S. PATENT DOCUMENTS

2005/0207630 A1* 9/2005 Chan ..................... G06T 7/0012
382/131
2007/0177785 A1* 8/2007 Raffy ..................... G16H 30/20
382/131

(Continued)

FOREIGN PATENT DOCUMENTS

WO 2009/090894 7/2009

OTHER PUBLICATIONS

International Search Report of PCT application No. PCT/JP2020/019397 dated Jul. 28, 2020.

(Continued)

*Primary Examiner* — Oneal R Mistry
(74) *Attorney, Agent, or Firm* — WENDEROTH, LIND & PONACK, L.L.P.

(57) ABSTRACT

A computer obtains a chest X-ray image, detects boundary lines in the chest X-ray image using a model constructed through machine learning, sets a third lung area including at least one of a first lung area or a second lung area, extracts a vascular index indicating at least one of thickness or density of at least one pulmonary blood vessel present in an area included in the third lung area, determines whether the area included in the third lung area is in an abnormal state on a basis of the vascular index and a reference index based on indices extracted in advance from an area in chest X-ray (Continued)

images in a normal state corresponding to the area included in the third lung area, and outputs, if determining that the area included in the third lung area is in an abnormal state, information indicating a result of the determination.

30 Claims, 40 Drawing Sheets

(51) Int. Cl.
    *G16H 30/40*     (2018.01)
    *G16H 50/20*     (2018.01)

(52) U.S. Cl.
    CPC ............... *G06T 2207/10116* (2013.01); *G06T 2207/20021* (2013.01); *G06T 2207/20081* (2013.01); *G06T 2207/20084* (2013.01); *G06T 2207/30048* (2013.01); *G06T 2207/30061* (2013.01); *G06T 2207/30101* (2013.01)

(56) References Cited

U.S. PATENT DOCUMENTS

| | | | | |
|---|---|---|---|---|
| 2010/0312094 | A1* | 12/2010 | Guttman | A61B 34/20 600/411 |
| 2016/0005220 | A1* | 1/2016 | Weingarten | G06T 7/0012 382/131 |
| 2018/0101645 | A1* | 4/2018 | Sorenson | G06V 30/19167 |
| 2019/0320934 | A1* | 10/2019 | Odry | G06N 3/006 |
| 2019/0371474 | A1* | 12/2019 | Borsic | A61B 34/10 |

OTHER PUBLICATIONS

Xiaosong Wang et al., "ChestX-ray8: Hospital-scale Chest X-ray Database and Benchmarks on Weakly-Supervised Classification and Localization of Common Thorax Diseases", CVPR2017, May 5, 2017.

Olaf Ronneberger et al., "U-Net: Convolutional Networks for Biomedical Image Segmentation", Medical Image Computing and Computer-Assisted Intervention(MICCAI), Springer, LNCS, vol. 9351, pp. 234-241, Nov. 18, 2015.

Jonathan Long et al., "Fully Convolutional Networks for Semantic Segmentation", In CVPR, Nov. 14, 2014.

Jinwon An et al., "Variational Autoencoder based Anomaly Detection using Reconstruction Probability", SNU Data Mining Center, Feb. 2015 Special Lecture on IE, Dec. 27, 2015.

Paola Campadelli et al., "A Fully Automated Method for Lung Nodule Detection From Postero-Anterior Chest Radiographs", IEEE Transactions on Medical Imaging, vol. 25, No. 12, Dec. 12, 2006, pp. 1588-1603.

* cited by examiner

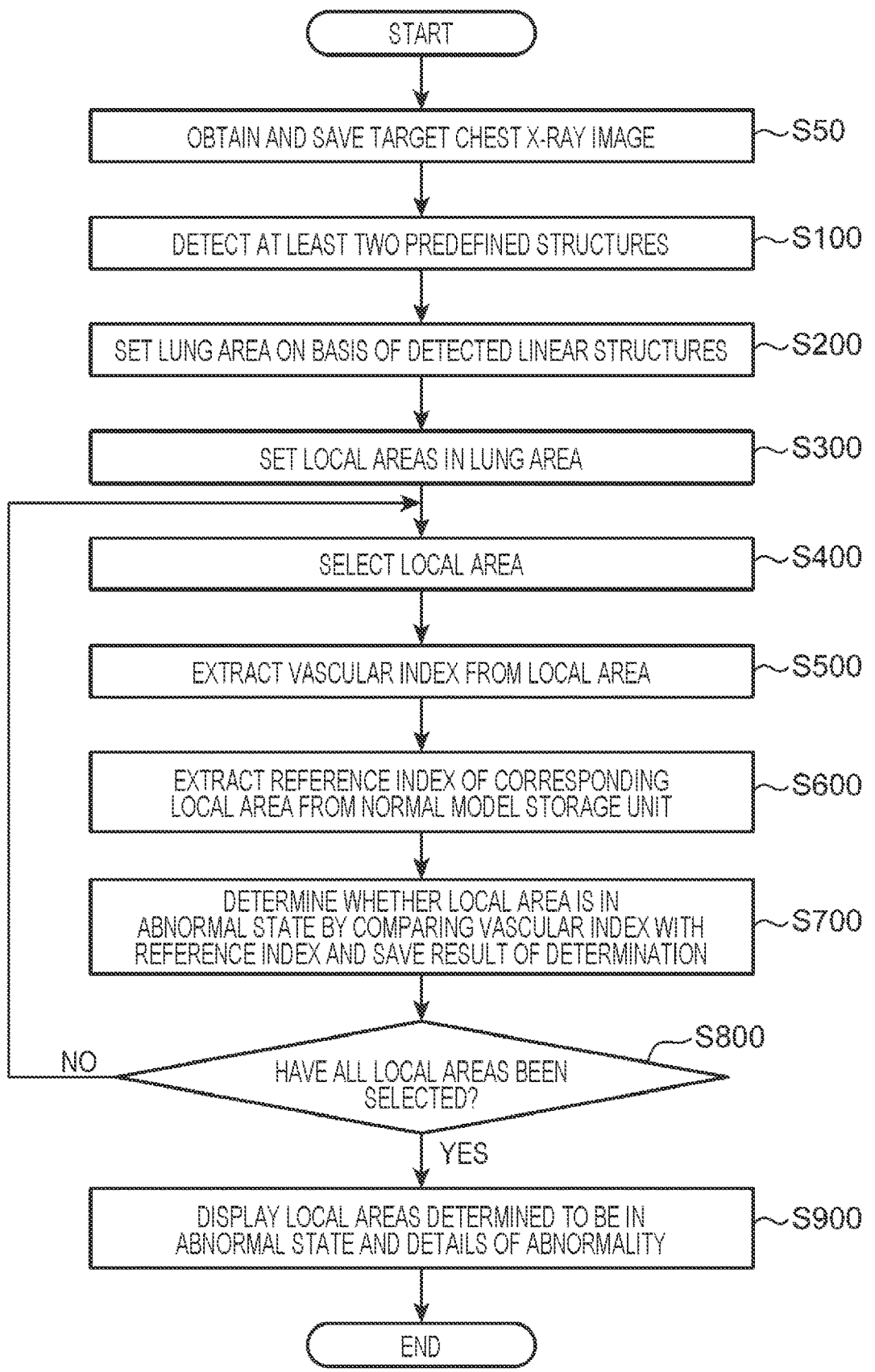

Ix

Py

Py  Ix

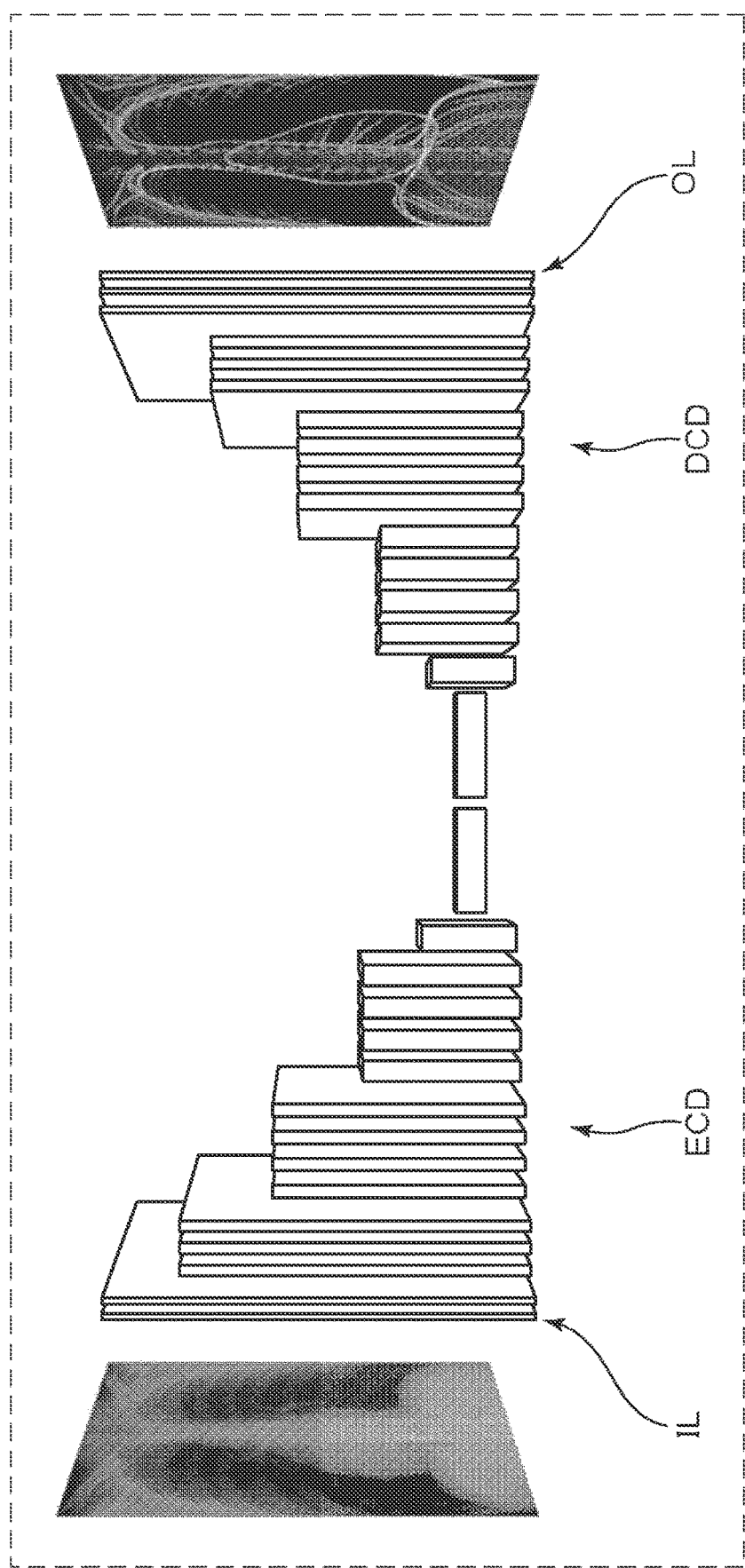

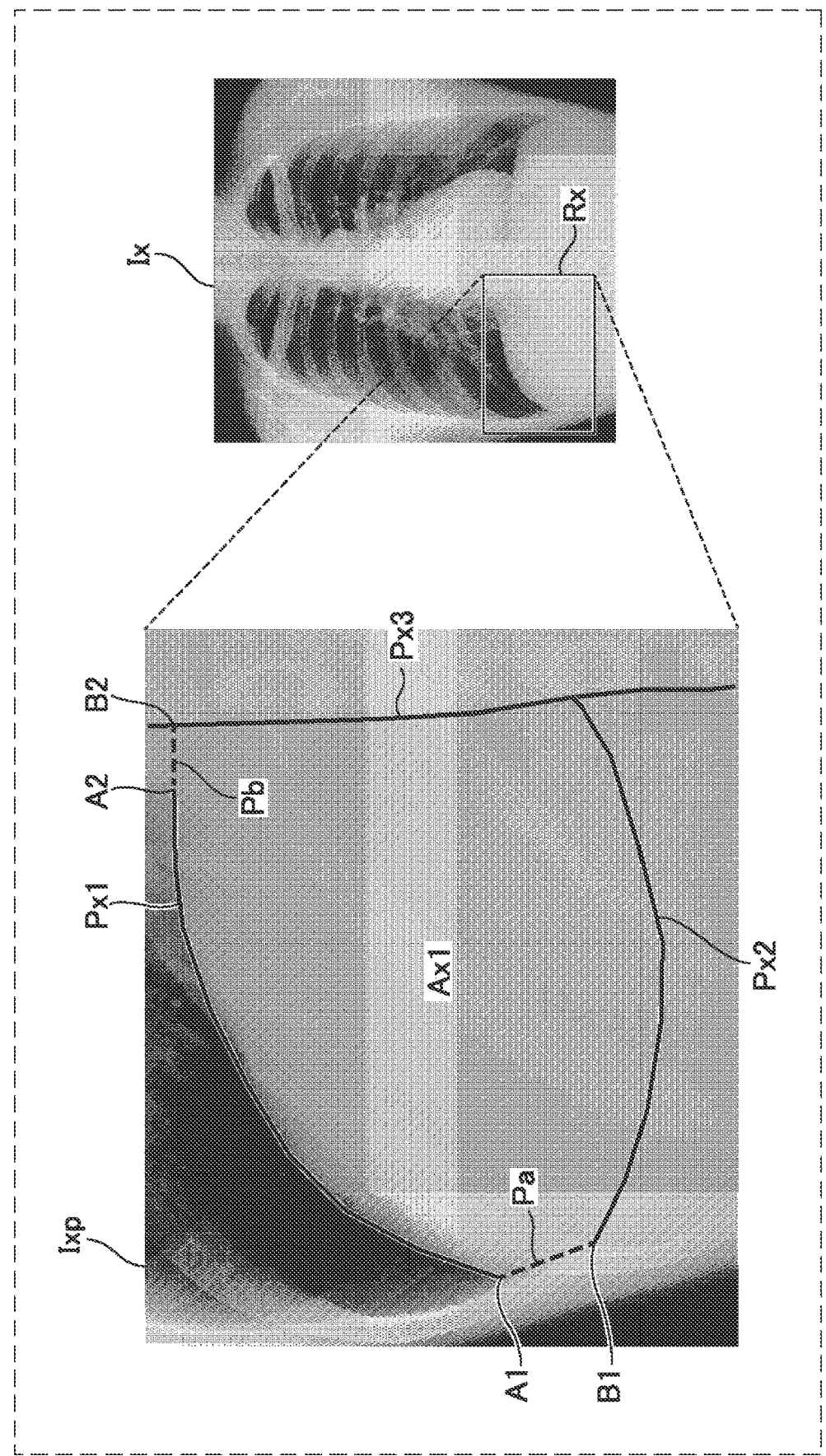

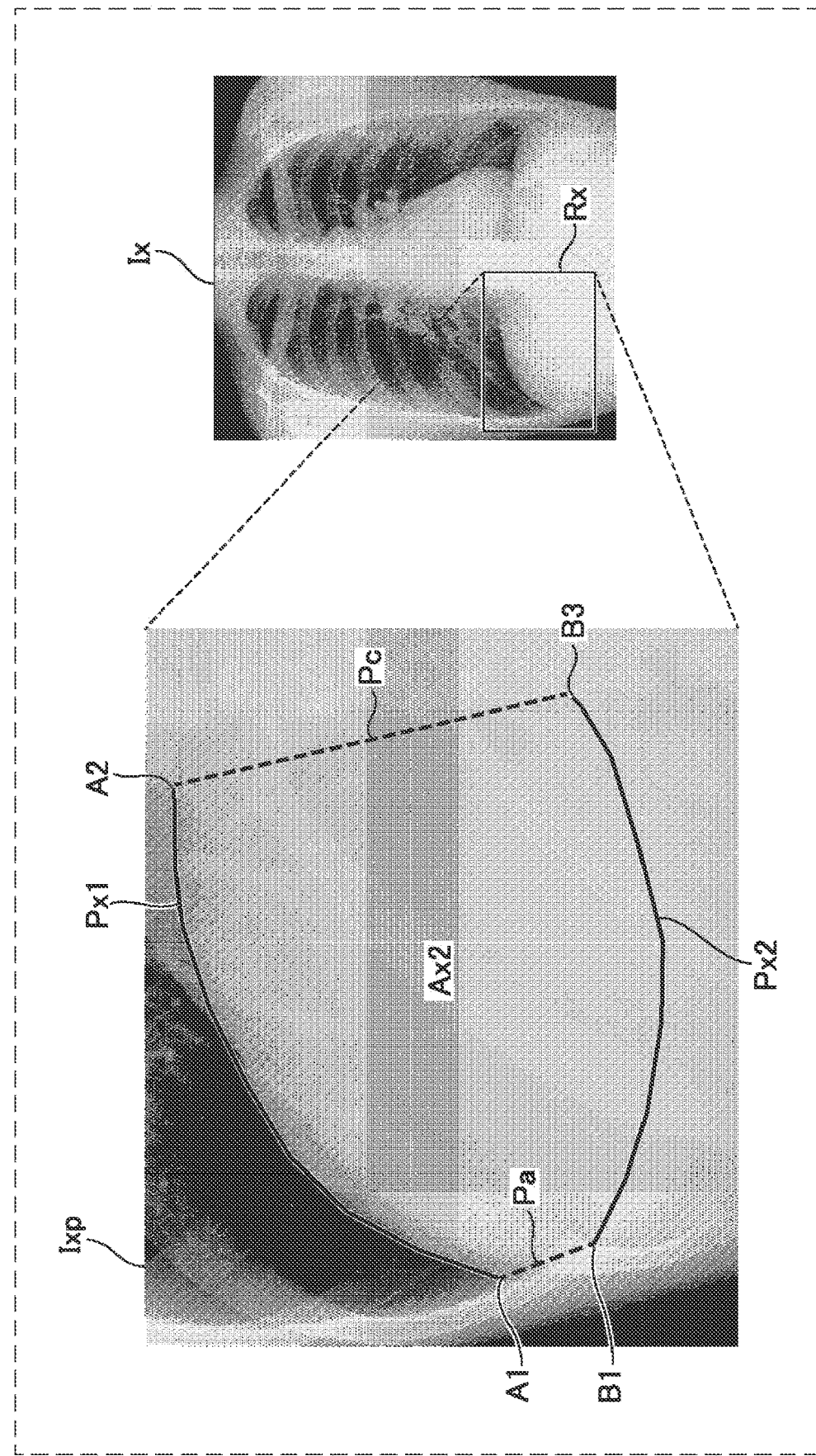

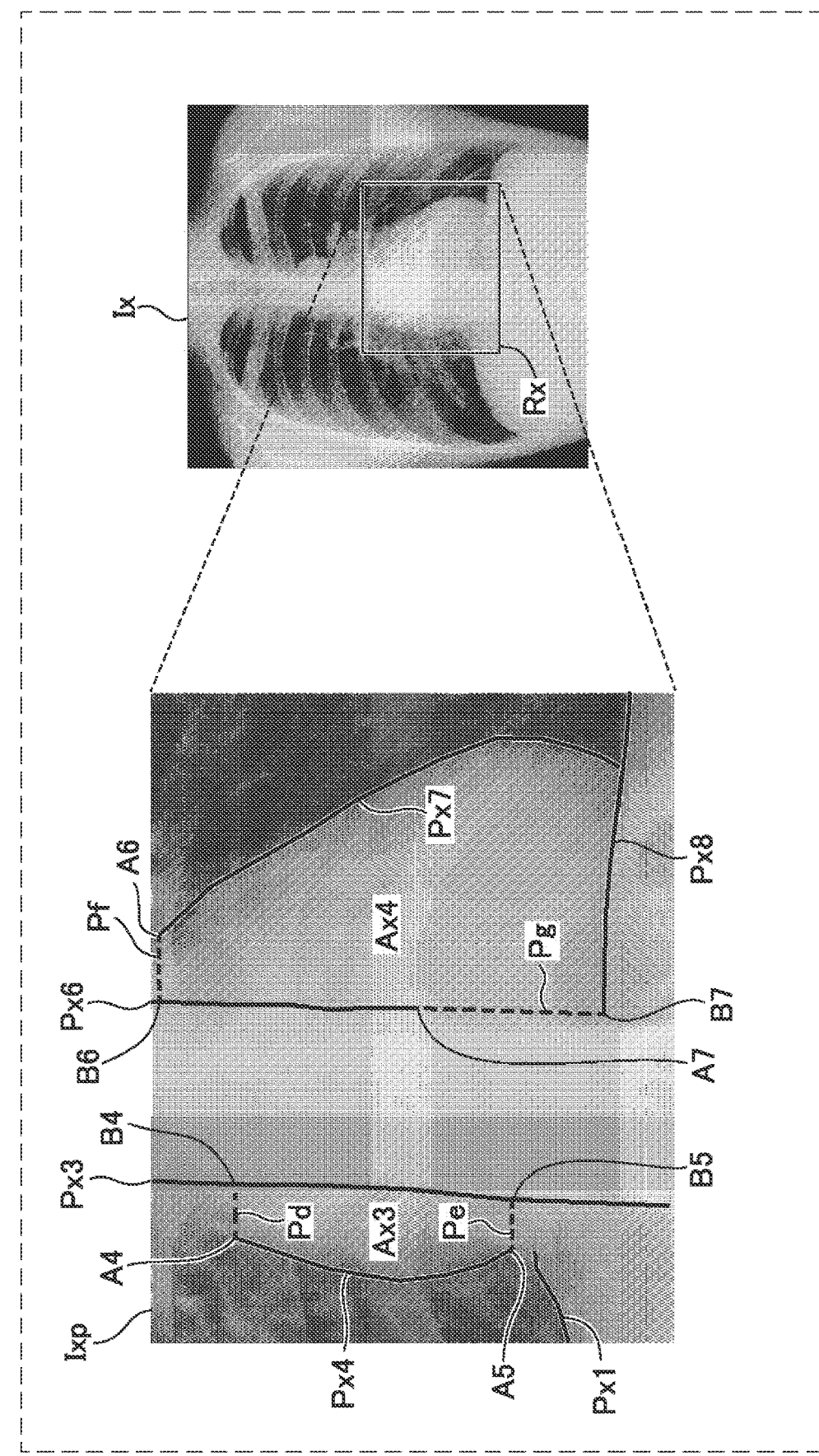

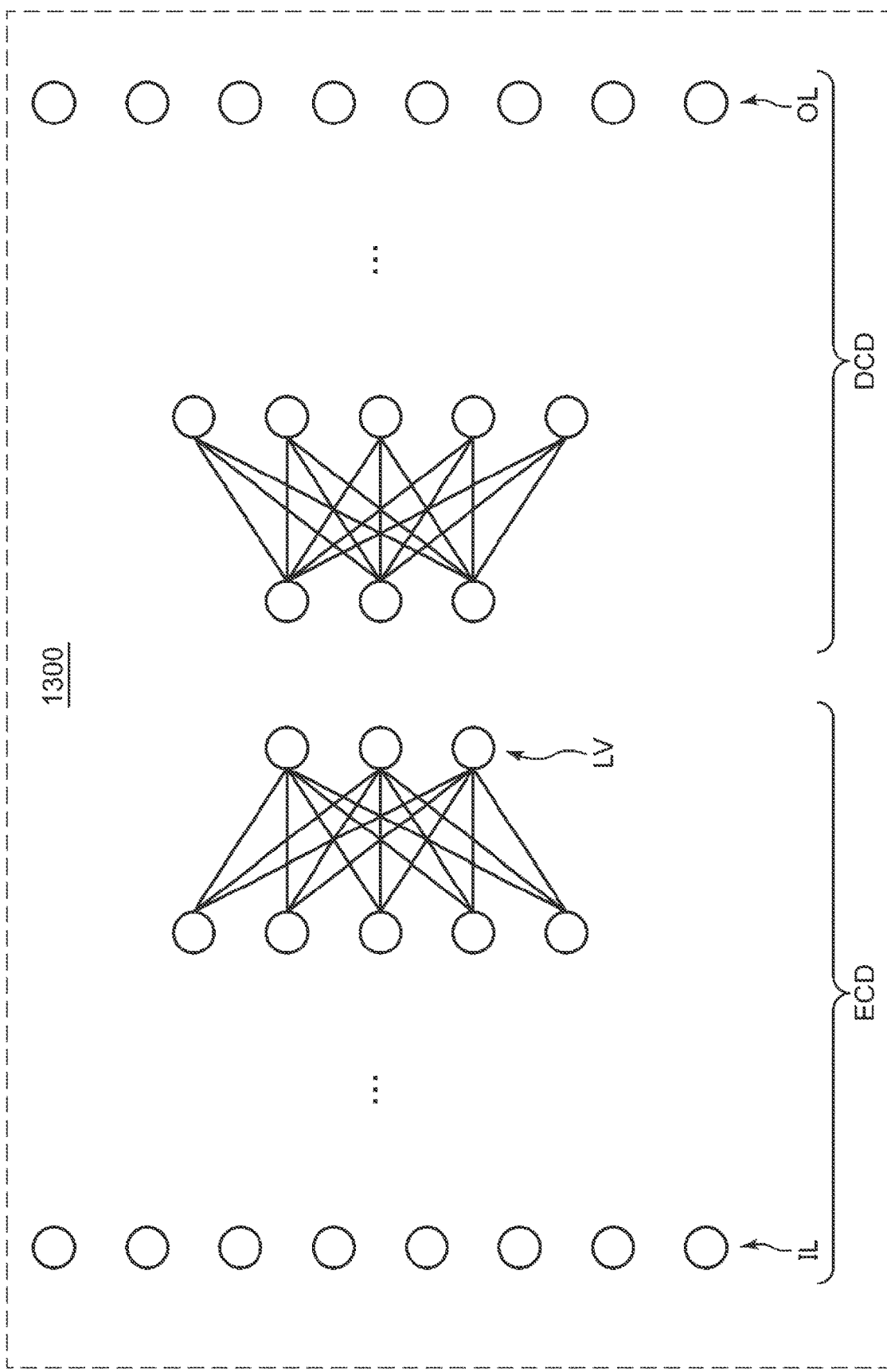

METHOD FOR DETECTING ABNORMALITY, NON-TRANSITORY COMPUTER-READABLE RECORDING MEDIUM STORING PROGRAM FOR DETECTING ABNORMALITY, ABNORMALITY DETECTION APPARATUS, SERVER APPARATUS, AND METHOD FOR PROCESSING INFORMATION

BACKGROUND

1. Technical Field

The present disclosure relates to a technique for processing a medical image and more specifically to a technique for detecting an abnormal state in a chest X-ray image.

2. Description of the Related Art

During these years, apparatuses, software, and/or the like that detect lesion areas in medical images or that estimate findings and disease names are being developed. A diagnosis that employs such an apparatus and/or software is called "computer-aided diagnosis (CAD)" and expected to reduce a burden on a doctor performing interpretation.

A diagnosis employing a chest X-ray image is the most common method among various methods for diagnosing chest diseases. This is because costs of devices for capturing chest X-ray images and costs of capturing chest X-ray images are low and such devices are widely used.

Examples of the CAD for a chest X-ray image include a technique for detecting a lesion area after performing machine learning using images of lesions (refer to X. Wang, Y. Peng, L. Lu, Z. Lu, M. Bagheri, and R. Summers, "ChestX-ray8: Hospital-Scale Chest X-Ray Database and Benchmarks on Weakly-Supervised Classification and Localization of Common Thorax Diseases", CVPR, 2017) and a technique for detecting an abnormal area using frame images obtained by successively capturing images of a chest (refer to International Publication No. 2009/090894).

International Publication No. 2009/090894 discloses a technique for determining whether a state of ventilation is abnormal for each sub-area and whether a state of blood flow is abnormal for each sub-area by dividing a lung area in each of frame images into sub-areas and conducting an image analysis in the same sub-area between the frame images.

SUMMARY

In the technique described in International Publication No. 2009/090894, however, a density histogram is created from signal values of pixels of a chest X-ray image, a threshold is obtained through a discriminant analysis or the like, and areas whose signals are higher than the obtained threshold are extracted as candidates for a lung area to be extracted. Further improvements, therefore, are necessary.

In one general aspect, the techniques disclosed here feature a method for detecting an abnormality. The method includes obtaining, using a computer, a chest X-ray image, detecting, in the obtained chest X-ray image using the computer and a model constructed through machine learning before the detecting, boundary lines of images of anatomical structures whose ranges of X-ray transmittances are different from one another, setting, using the computer, a third lung area in the chest X-ray image including at least one of a first lung area where one or more lungs and a heart overlap or a second lung area where one of the lungs and a liver overlap on a basis of the detected boundary lines, extracting, using the computer, a vascular index indicating at least one of thickness or density of at least one pulmonary blood vessel present in an area included in the third lung area, determining, using the computer, whether the area included in the third lung area is in an abnormal state on a basis of the vascular index and a reference index based on indices extracted, using a method used to extract the vascular index, in advance from an area in chest X-ray images in a normal state corresponding to the area included in the third lung area, and outputting, if it is determined that the area included in the third lung area is in an abnormal state, information indicating a result of the determining using the computer.

According to the above aspect, further improvement can be achieved.

It should be noted that this general or specific aspect may be implemented as an apparatus, a system, an integrated circuit, a computer program, a computer-readable storage medium, or any selective combination thereof. The computer-readable storage medium may be, for example, a non-transitory storage medium such as a compact disc read-only memory (CD-ROM).

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 3 is a flowchart according to the first embodiment;

FIG. 7 is a diagram schematically illustrating the architecture of a U-Net;

FIG. 8 is a diagram illustrating an example of a method for setting an area where one of lungs and a liver overlap and the area;

FIG. 9 is a diagram illustrating another example of the method for setting an area where one of the lungs and the liver overlap and the area;

FIG. 10 is a diagram illustrating an example of a method for setting an area where one or more of the lungs and a heart overlap and the area;

FIG. 33 is a diagram illustrating the network configuration of a variational autoencoder;

DETAILED DESCRIPTION

Underlying Knowledge Forming Basis of Aspect of the Present Disclosure

First, underlying knowledge forming the basis of an aspect of the present disclosure will be described. International Publication No. 2009/090894 discloses a technique in which a density histogram is created from signal values of pixels of a chest X-ray image, a threshold is obtained through a discriminant analysis or the like, and areas whose signals are higher than the obtained threshold are extracted as candidates for a lung area to be extracted, and edges are detected near boundaries of the candidates in order to determine a boundary line of the lung area. In a chest X-ray image, however, signal values of pixels in an area where one or more lungs and a heart overlap are not as large as signal values of pixels in an area where one of the lungs and another organ do not overlap, and signal values of pixels in an area where one of the lungs and the liver overlap are not as high as signal values of pixels in an area where one of the lungs and another organ do not overlap. This will be described with reference to FIGS. 39 and 40.

Figure 39:
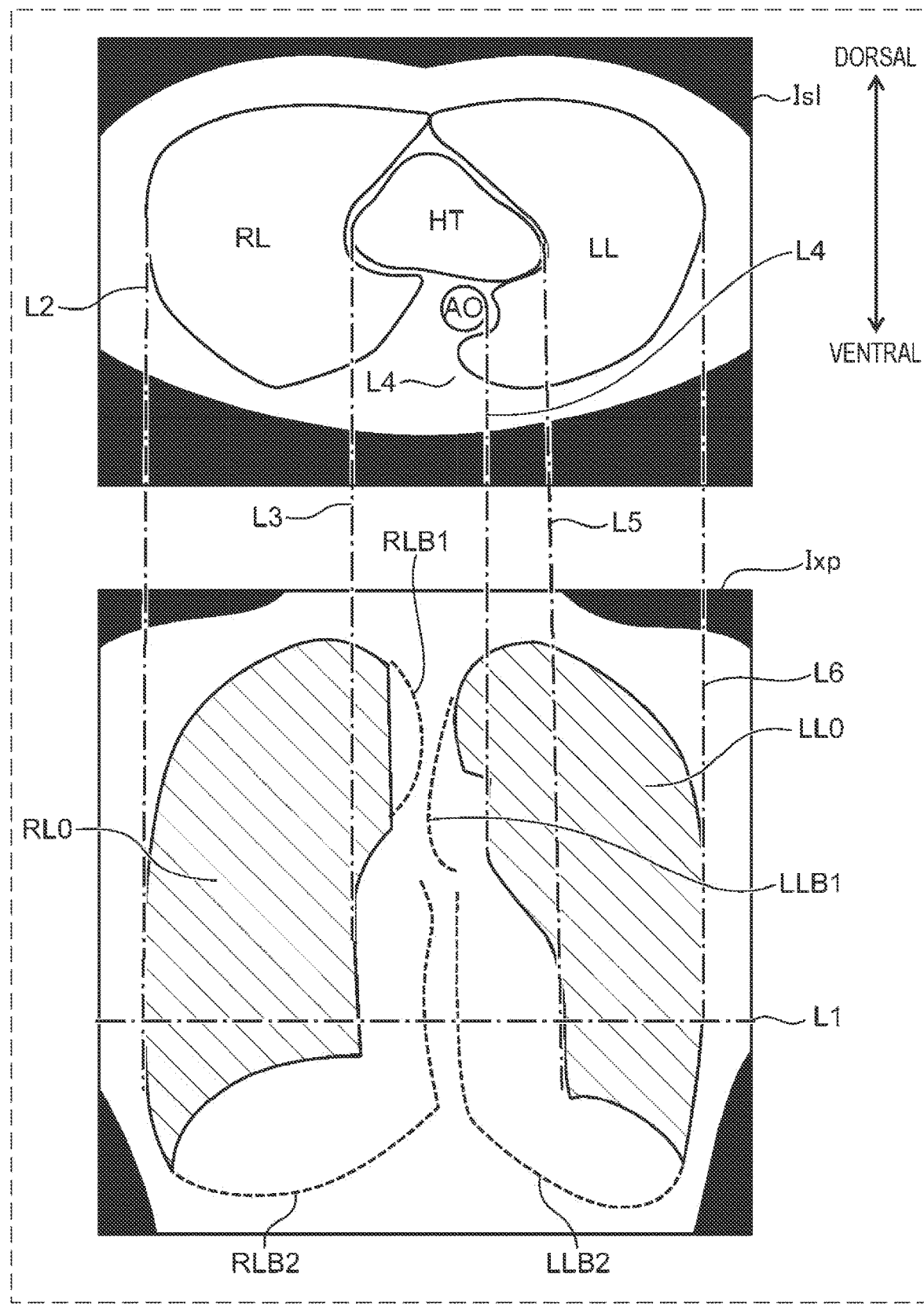
FIG. 39 is a diagram illustrating a chest X-ray front image and a computed tomography (CT) slice image.

FIG. 39 illustrates a chest X-ray front image Ixp and a CT slice image Isl indicating a cross section at a position L1 of the chest X-ray front image Ixp. The slice image Isl includes a right lung RL, a left lung LL, a heart HT, and a descending aorta AO. A dash-dot line L2 connects the chest X-ray front image Ixp and the slice image Isl to each other at a right end of the right lung RL. "Left" and "right" herein are based on not a chest X-ray image but a body of a subject. A dash-dot line L3 connects the chest X-ray front image Ixp and the slice image Isl to each other at a right end of a right atrium. A dash-dot line L4 connects the chest X-ray front image Ixp and the slice image Isl to each other at a left end of the descending aorta AO. A dash-dot line L5 connects the chest X-ray front image Ixp and the slice image Isl to each other at a left end of a left ventricle. A dash-dot line L6 connects the chest X-ray front image Ixp and the slice image Isl to each other at a left end of the left lung LL. Because the X-ray absorbance of the lungs is low, signal values of pixels in areas RL0 and LL0 in the chest X-ray front image Ixp are small, and the areas RL0 and LL0 are determined as areas where the right lung RL and the left lung LL are present, respectively. It can be seen from the slice image Isl, however, that the right lung RL and the left lung LL are also present in front of and behind the heart HT. It is therefore important to make an image diagnosis in such an area in the chest X-ray front image Ixp, that is, an area where one or more of the lungs and the heart overlap, in order not to overlook a lung lesion in the area.

Figure 40:
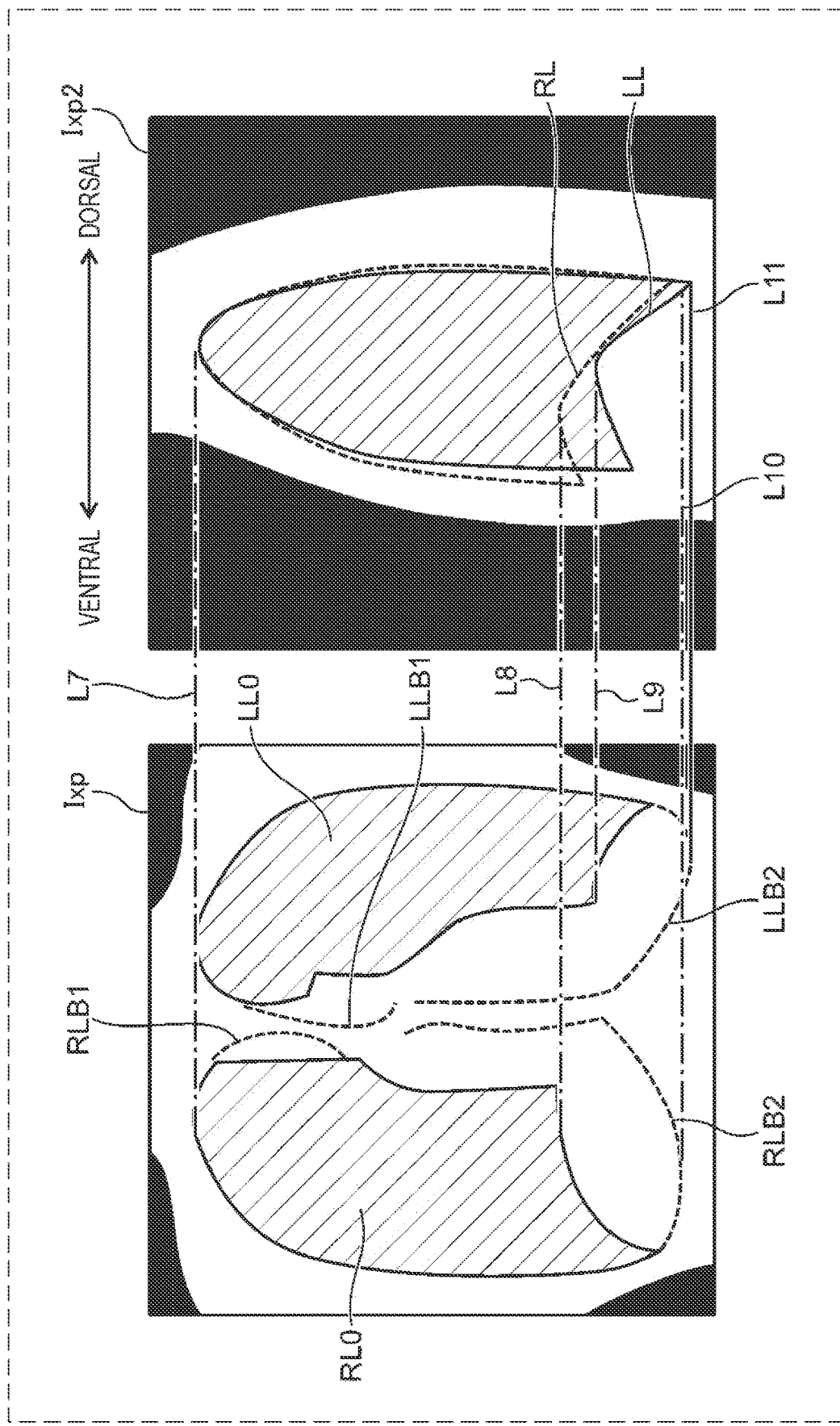
FIG. 40 is a diagram illustrating the chest X-ray front image and a chest X-ray side image.

FIG. 40 illustrates the chest X-ray front image Ixp and a chest X-ray side image Ixp2 side-by-side. In the chest X-ray side image Ixp2, an area RL where the right lung is present is indicated by a broken line, and an area LL where the left lung is present is indicated by a solid line. A dash-dot line L7 connects the chest X-ray front image Ixp and the chest X-ray side image Ixp2 to each other at an upper end of the lungs. A dash-dot line L8 connects the chest X-ray front image Ixp and the chest X-ray side image Ixp2 to each other at an upper end of a right diaphragm dome. A dash-dot line L9 connects the chest X-ray front image Ixp and the chest X-ray side image Ixp2 to each other at an upper end of a left diaphragm dome. A dash-dot line L10 connects the chest X-ray front image Ixp and the chest X-ray side image Ixp2 to each other at a lower end of the right lung (dorsal). A solid line L11 connects the chest X-ray front image Ixp and the chest X-ray side image Ixp2 to each other at a lower end of the left lung (dorsal). As described above, because the X-ray absorbance of the lungs is small, the signal values of the pixels in the areas RL0 and LL0 in the chest X-ray front image Ixp are small, and the areas RL0 and LL0 are determined as areas where the right lung RL and the left lung LL are present, respectively. It can be seen from the chest X-ray side image Ixp2, however, that the right lung is also present under the dash-dot line L8 and the left lung is also present under the dash-dot line L9. Although not illustrated in FIG. 40, the liver is below the right lung across a diaphragm, and a stomach and other organs are below the left lung across the diaphragm. It is therefore important to make an image diagnosis in such an area in the chest X-ray front image Ixp, that is, an area where one of the lungs and another organ overlap, in order not to overlook a lung lesion in the area. The other organ may be the liver or the stomach.

With the method for determining boundary lines of a lung area disclosed in International Publication No. 2009/090894, therefore, it is difficult to detect an abnormality in an area where one or more of the lungs and the heart overlap and an area where one of the lungs and the liver overlap in a chest X-ray image. The present inventor paid attention to various linear structures (an example of boundary lines) drawn in chest X-ray images and conceived the following aspects of the present disclosure with which whether there is an abnormality can be determined in the area where one or more of the lungs and the heart overlap and/or the area where one of the lungs and the liver overlap.

A first aspect of the present disclosure is a method for detecting an abnormality. The method includes
  obtaining, using a computer, a chest X-ray image,
  detecting, in the obtained chest X-ray image using the computer and a model constructed through machine learning before the detecting, boundary lines of images of anatomical structures whose ranges of X-ray transmittances are different from one another,
  setting, using the computer, a third lung area in the chest X-ray image including at least one of a first lung area where one or more lungs and a heart overlap or a second lung area where one of the lungs and a liver overlap on a basis of the detected boundary lines,
  extracting, using the computer, a vascular index indicating at least one of thickness or density of at least one pulmonary blood vessel present in an area included in the third lung area,
  determining, using the computer, whether the area included in the third lung area is in an abnormal state on a basis of the vascular index and a reference index based on indices extracted, using a method used to extract the vascular index, in advance from an area in chest X-ray images in a normal state corresponding to the area included in the third lung area, and
  outputting, if it is determined that the area included in the third lung area is in an abnormal state, information indicating a result of the determining using the computer.

In the first aspect, boundary lines are detected while focusing upon various boundary lines drawn in chest X-ray images. A third lung area including a first lung area where one or more of the lungs and the heart overlap and/or a second lung area where one of the lungs and the liver overlap, therefore, can be set on the basis of the boundary lines. According to the first aspect, whether there is an abnormality in an area included in the third lung area can be determined. If it is determined that there is an abnormality in the area included in the third lung area, information indicating a result of the determination is output. Useful information, therefore, can be provided for the user. As a result, the method for detecting an abnormality according to the first aspect can not only provide useful information for an interpreter but also be used by a clinician or a radiologist to give a diagnosis or study by himself/herself or a medical student to be educated or study by himself/herself. With the method for detecting an abnormality according to the first aspect, an abnormality can be detected in the first lung area (an area in a chest X-ray image where one or more of the lungs and the heart overlap) and/or the second lung area (an area in a chest X-ray image where one of the lungs and the liver overlap) on the basis of a vascular index, the first and second lung areas being often not included as abnormality detection target areas in the case of abnormality detection techniques in conventional diagnosis aiding techniques for chest X-ray images.

In the above first aspect, for example,
  in the detecting, boundary lines of at least two of a left ventricle shadow, a descending aorta shadow, a left diaphragm dome shadow, a left edge of a vertebral body, a right edge of the vertebral body, a right atrium shadow, and a right diaphragm dome shadow may be detected.

In the setting, the third lung area including the first lung area may be set, the first lung area being set as one or more areas, each of which is sandwiched by at least two of the boundary lines detected in the detecting.

According to this aspect, the first lung area in a chest X-ray image, where one or more of the lungs and the heart overlap, can be set more accurately on the basis of detected boundary lines.

In the above first aspect, for example,
  in the detecting, boundary lines of at least the left ventricle shadow, the descending aorta shadow, the left diaphragm dome shadow, the right edge of the vertebral body, and the right atrium shadow may be detected among boundary lines of the left ventricle shadow, the descending aorta shadow, the left diaphragm dome shadow, the left edge of the vertebral body, the right edge of the vertebral body, the right atrium shadow, and the right diaphragm dome shadow.

In the setting, the first lung area may be set as an area sandwiched by, among the boundary lines detected in the detecting, the boundary lines of the left ventricle shadow, the descending aorta shadow, and the left diaphragm dome shadow and an area sandwiched by the boundary lines of the right edge of the vertebral body and the right atrium shadow.

According to this aspect, the first lung area in a chest X-ray image, where one or more of the lungs and the heart overlap, can be set more accurately on the basis of detected boundary lines.

In the above first aspect, for example, in the detecting, boundary lines of at least the left edge of the vertebral body, the left ventricle shadow, the left diaphragm dome shadow, the right edge of the vertebral body, and the right atrium shadow may be detected among boundary lines of the left ventricle shadow, the descending aorta shadow, the left diaphragm dome shadow, the left edge of the vertebral body, the right edge of the vertebral body, the right atrium shadow, and the right diaphragm dome shadow.

In the setting, the first lung area may be set as an area sandwiched by, among the boundary lines detected in the detecting, the boundary lines of the left edge of the vertebral body, the left ventricle shadow, and the left diaphragm dome shadow and an area sandwiched by the boundary lines of the right edge of the vertebral body and the right atrium shadow.

According to this aspect, the first lung area in a chest X-ray image, where one or more of the lungs and the heart overlap, can be set more accurately on the basis of detected boundary lines.

In the above aspect, for example,
in the setting, the first lung area may be set as one or more closed area defined by the boundary lines detected in the detecting and interpolation lines connecting adjacent ones of the boundary lines to each other.

According to this aspect, the first lung area in a chest X-ray image, where one or more of the lungs and the heart overlap, can be set more certainly even if detected boundary lines do not form a closed area.

In the above first aspect, for example,
in the detecting, boundary lines of at least two of a right diaphragm dome shadow, a right dorsal lung base shadow, and a right edge of a vertebral body may be detected.

In the setting, the third lung area including the second lung area may be set, the second lung area being set as an area sandwiched by at least two of the boundary lines detected in the detecting.

According to this aspect, the second lung area in a chest X-ray image, where one of the lungs and the liver overlap, can be set more accurately on the basis of detected boundary lines.

In the above first aspect, for example, in the detecting, the boundary lines of at least the right diaphragm dome shadow and the right dorsal lung base shadow may be detected among the boundary lines of the right diaphragm dome shadow, the right dorsal lung base shadow, and the right edge of the vertebral body.

In the setting, the second lung area may be set as an area sandwiched by, among the boundary lines detected in the detecting, the boundary lines of the right diaphragm dome shadow and the right dorsal lung base shadow.

According to this aspect, the second lung area in a chest X-ray image, where one of the lungs and the liver overlap, can be set more accurately on the basis of detected boundary lines.

In the above first aspect, for example,
in the detecting, the boundary lines of the right diaphragm dome shadow, the right dorsal lung base shadow, and the right edge of the vertebral body may be detected.

In the setting, the second lung area may be set as an area sandwiched by the boundary lines of the right diaphragm dome shadow, the right dorsal lung base shadow, and the right edge of the vertebral body detected in the detecting.

According to this aspect, the second lung area in a chest X-ray image, where one of the lungs and the liver overlap, can be set more accurately on the basis of detected boundary lines.

In the above first aspect, for example,
in the setting, the second lung area may be set as a closed area defined by the boundary lines detected in the detecting and interpolation lines connecting adjacent ones of the boundary lines to each other.

According to this aspect, the second lung area in a chest X-ray image, where one of the lungs and the liver overlap, can be set more certainly even if detected boundary lines do not form a closed area.

The above first aspect may further include, for example,
calculating, if a boundary line of the right dorsal lung base shadow is detected in the detecting, a degree of reliability indicating how probable a result of the detecting of the boundary line of the right dorsal lung base shadow is using the computer and
estimating, if the degree of reliability is lower than or equal to a first threshold, the boundary line of the right dorsal lung base shadow on a basis of a position of at least one of the boundary lines detected in the detecting other than the boundary line of the right dorsal lung base shadow using the computer.

If the degree of reliability is higher than the first threshold in the setting of the second lung area, the boundary line of the right dorsal lung base shadow detected in the detecting may be used and, if the degree of reliability is lower than or equal to the first threshold, the boundary line of the right dorsal lung base shadow estimated in the estimating may be used.

According to this aspect, the second lung area can be set using an estimated right dorsal lung base shadow even if a degree of reliability, which indicates how probable a result of detection of the right dorsal lung base shadow is, is lower than or equal to the first threshold.

In the above first aspect, for example,
if the boundary line of the right dorsal lung base shadow estimated in the estimating is used in the setting of the second lung area, information for calling attention to an area including a right lung base may be output in the outputting.

According to this aspect, it is possible to get the user to pay attention to an area including the right lung base.

In the above first aspect, for example,
the third lung area may further include a fourth lung area located below the first lung area.

In the detecting, a boundary line of a left dorsal lung base shadow may be detected as one of the boundary lines.

According to this aspect, an abnormality can be detected in the fourth lung area below the first lung area (an area in a chest X-ray image where one or more of the lungs and the heart overlap) on the basis of the vascular index, the fourth lung area being often not included as an abnormality detection target area in the case of abnormality detection techniques in conventional diagnosis aiding techniques for chest X-ray images.

In the above first aspect, for example,
in the detecting, at least two boundary lines including the boundary line of the left dorsal lung base shadow may be detected among boundary lines of a left diaphragm dome shadow, the left dorsal lung base shadow, and a left edge of a vertebral body.

In the setting, the third lung area including the fourth lung area may be set, the fourth lung area being set as an area sandwiched by at least two of the boundary lines detected in the detecting.

According to this aspect, the fourth lung area in a chest X-ray image below the first lung area can be set more accurately on the basis of detected boundary lines.

In the above first aspect, for example,
in the detecting, the boundary lines of at least the left diaphragm dome shadow and the left dorsal lung base shadow may be detected among the boundary lines of the left diaphragm dome shadow, the left dorsal lung base shadow, and the left edge of the vertebral body.

In the setting, the fourth lung area may be set as an area sandwiched by, among the boundary lines detected in the detecting, the boundary lines of the left diaphragm dome shadow and the left dorsal lung base shadow.

According to this aspect, the fourth lung area in a chest X-ray image below the first lung area can be set more accurately on the basis of detected boundary lines.

In the above first aspect, for example,
in the detecting, boundary lines of a left diaphragm dome shadow, the left dorsal lung base shadow, and a left edge of a vertebral body may be detected.
In the setting, the fourth lung area may be set as an area sandwiched by the boundary lines of the left diaphragm dome shadow, the left dorsal lung base shadow, and the left edge of the vertebral body detected in the detecting.

According to this aspect, the fourth lung area in a chest X-ray image below the first lung area can be set more accurately on the basis of detected boundary lines.

In the above first aspect, for example,
in the setting, the fourth lung area may be set as a closed area defined by the boundary lines detected in the detecting and interpolation lines connecting adjacent ones of the boundary lines to each other.

According to this aspect, the fourth lung area in a chest X-ray image below the first lung area can be set more certainly even if detected boundary lines do not form a closed area.

The above first aspect may further include, for example,
calculating, using the computer, a degree of reliability indicating how probable a result of the detecting of the boundary line of the left dorsal lung base shadow is and
estimating, if the degree of reliability is lower than or equal to a second threshold, the boundary line of the left dorsal lung base shadow on a basis of a position of at least one of the boundary lines detected in the detecting other than the boundary line of the left dorsal lung base shadow using the computer.

If the degree of reliability is higher than the second threshold in the setting of the fourth lung area, the boundary line of the left dorsal lung base shadow detected in the detecting may be used and, if the degree of reliability is lower than or equal to the second threshold, the boundary line of the left dorsal lung base shadow estimated in the estimating may be used.

According to this aspect, the fourth lung area can be set using an estimated left dorsal lung base shadow even if a degree of reliability, which indicates how probable a result of detection of the left dorsal lung base shadow is, is lower than or equal to the second threshold.

In the above first aspect, for example,
if the boundary line of the left dorsal lung base shadow estimated in the estimating is used in the setting of the fourth lung area, information for calling attention to an area including a left lung base may be output in the outputting.

According to this aspect, it is possible to get the user to pay attention to an area including the left lung base.

In the above first aspect, for example,
in the outputting, an image of the area included in the third lung area determined to be in the abnormal state and details of the abnormal state of the area included in the third lung area may be output and displayed on a display as information indicating a result of the determining.

According to this aspect, beneficial information can be provided for the user.

The above first aspect may further include, for example, dividing, using the computer, the third lung area set in the setting into local areas 1 to n, each of which includes the area included in the third lung area, n being a natural number greater than or equal to 2.

In the extracting, a vascular index i indicating at least one of thickness or density of at least one pulmonary blood vessel present in a local area i may be extracted as the vascular index, i being a natural number greater than or equal to 1 and less than or equal to n.

In the determining, whether the local area i is in an abnormal state may be determined on a basis of the vascular index i and a reference index i based on indices extracted, using a method used to extract the vascular index i, in advance from an area in chest X-ray images in a normal state corresponding to the local area i.

In the outputting, an image of a local area j determined to be in an abnormal state and details of the abnormal state of the local area j may be displayed on the display, j being a natural number greater than or equal to 1 and less than or equal to n.

According to this aspect, since the third lung area is divided into local areas and whether each of the local areas is in an abnormal state is determined, the resolution of an area determined to be abnormal improves.

The above first aspect may further include, for example,
generating, using the computer, groups 1 to m including different ones of the local areas 1 to n in accordance with two-dimensional distances from hila in the obtained chest X-ray image, m being a natural number greater than or equal to 2.

In the extracting, a vascular index k indicating at least one of thickness or density of at least one pulmonary blood vessel present in a group k may be extracted as the vascular index, k being a natural number greater than or equal to 1 and less than or equal to m.

In the determining, whether the group k is in an abnormal state may be determined on a basis of the vascular index k and a reference index k based on indices extracted, using a method used to extract the vascular index k, in advance from an area in chest X-ray images in a normal state corresponding to the group k.

In the outputting, an image of a group h determined to be in an abnormal state and details of the abnormal state of the group h may be displayed on the display, h being a natural number greater than or equal to 1 and less than or equal to m.

According to this aspect, since local areas including similar thicknesses or densities of at least one pulmonary blood vessel are grouped together, the vascular index can be obtained more accurately for each group. The reference index, which is obtained in advance, can be obtained more easily since the number of training images for obtaining the reference index is greater than the number of images of local areas, for example, even if the number of training images for obtaining the reference index is small.

In the above first aspect, for example,
the model may be obtained by performing, using training chest X-ray images, which are the chest X-ray images in the normal state, as input data and images indicating boundary lines in the training chest X-ray images as training data, the machine learning on a basis of a neural network that makes predictions in units of pixels such that the boundary lines are detected from the training chest X-ray images.

According to this aspect, boundary lines are detected using a model obtained by performing, using training chest X-ray images, which are the chest X-ray images in the normal state, as input data and image indicating boundary lines in the training chest X-ray images as training data, machine learning on the basis of a neural network that makes predictions in units of pixels such that the boundary lines are detected from the training chest X-ray images. Since predictions are made in units of pixels, boundary lines can be accurately detected.

In the above first aspect, for example, the reference index may be a threshold set in advance for a probability density function of indices extracted, using the method used to extract the vascular index, in advance from the area in the chest X-ray images in the normal state corresponding to the area included in the third lung area or the indices extracted, using the method used to extract the vascular index, in advance from the area in the chest X-ray images in the normal state corresponding to the area included in the third lung area.

According to this aspect, an abnormality can be detected more accurately using a probability density function or a threshold.

A second aspect of the present disclosure is a non-transitory computer-readable recording medium storing a program for detecting an abnormality that causes a computer to function as an obtainer that obtains a chest X-ray image, a detector that detects, in the obtained chest X-ray image, boundary lines of images of anatomical structures whose ranges of X-ray transmittances are different from one another using a model constructed through machine learning before the detection, a setter that sets a third lung area in the chest X-ray image including at least one of a first lung area where one or more lungs and a heart overlap or a second lung area where one of the lungs and a liver overlap on a basis of the detected boundary lines, a determiner that extracts a vascular index indicating at least one of thickness or density of at least one pulmonary blood vessel present in an area included in the third lung area and that determines whether the area included in the third lung area is in an abnormal state on a basis of the extracted vascular index and a reference index based on indices extracted, using a method used to extract the vascular index, in advance from an area in chest X-ray images in a normal state corresponding to the area included in the third lung area, and an output controller that outputs, if it is determined that the area included in the third lung area is in an abnormal state, information indicating a result of the determination made by the determiner.

According to the second aspect, boundary lines are detected while focusing upon various boundary lines drawn in chest X-ray images. A third lung area including a first lung area where one or more of the lungs and the heart overlap and/or a second lung area where one of the lungs and the liver overlap, therefore, can be set on the basis of the boundary lines. According to the second aspect, whether there is an abnormality in an area included in the third lung area can be determined. If it is determined that there is an abnormality in the area included in the third lung area, information indicating a result of the determination is output. Useful information, therefore, can be provided for the user. As a result, the method for detecting an abnormality according to the second aspect can not only provide useful information for an interpreter but also be used by a clinician or a radiologist to give a diagnosis or study by himself/herself or a medical student to be educated or study by himself/herself. With the method for detecting an abnormality according to the second aspect, an abnormality can be detected in the first lung area (an area in a chest X-ray image where one or more of the lungs and the heart overlap) and/or the second lung area (an area in a chest X-ray image where one of the lungs and the liver overlap) on the basis of a vascular index, the first and second lung areas being often not included as abnormality detection target areas in the case of abnormality detection techniques in conventional diagnosis aiding techniques for chest X-ray images.

A third aspect of the present disclosure is an abnormality detection apparatus including an obtainer that obtains a chest X-ray image, a detector that detects, in the obtained chest X-ray image, boundary lines of images of anatomical structures whose ranges of X-ray transmittances are different from one another using a model constructed through machine learning before the detection, a setter that sets a third lung area in the chest X-ray image including at least one of a first lung area where one or more lungs and a heart overlap or a second lung area where one of the lungs and a liver overlap on a basis of the detected boundary lines, a determiner that extracts a vascular index indicating at least one of thickness or density of at least one pulmonary blood vessel present in an area included in the third lung area and that determines whether the area included in the third lung area is in an abnormal state on a basis of the extracted vascular index and a reference index based on indices extracted, using a method used to extract the vascular index, in advance from an area in chest X-ray images in a normal state corresponding to the area included in the third lung area, and an output controller that outputs, if it is determined that the area included in the third lung area is in an abnormal state, information indicating a result of the determination made by the determiner.

According to the third aspect, boundary lines are detected while focusing upon various boundary lines drawn in chest X-ray images. A third lung area including a first lung area where one or more of the lungs and the heart overlap and/or a second lung area where one of the lungs and the liver overlap, therefore, can be set on the basis of the boundary lines. According to the third aspect, whether there is an abnormality in an area included in the third lung area can be determined. If it is determined that there is an abnormality in the area included in the third lung area, information indicating a result of the determination is output. Useful information, therefore, can be provided for the user. As a result, the method for detecting an abnormality according to the third aspect can not only provide useful information for an interpreter but also be used by a clinician or a radiologist to give a diagnosis or study by himself/herself or a medical student to be educated or study by himself/herself. With the method for detecting an abnormality according to the third aspect, an abnormality can be detected in the first lung area (an area in a chest X-ray image where one or more of the lungs and the heart overlap) and/or the second lung area (an area in a chest X-ray image where one of the lungs and the liver overlap) on the basis of a vascular index, the first and second lung areas being often not included as abnormality detection target areas in the case of abnormality detection techniques in conventional diagnosis aiding techniques for chest X-ray images.

A fourth aspect of the present disclosure is a server apparatus including an obtainer that obtains a chest X-ray image, a detector that detects, in the obtained chest X-ray image, boundary lines of images of anatomical structures whose ranges of X-ray transmittances are different from one another using a model constructed through machine learning before the detection, a setter that sets a third lung area in the chest X-ray image including at least one of a first lung area where one or more lungs and a heart overlap each other or a second lung area where one of the lungs and a liver overlap on a basis of the detected boundary lines, a determiner that extracts a vascular index indicating at least one of thickness or density of at least one pulmonary blood vessel present in an area included in the third lung area and that determines whether the area included in the third lung area is in an abnormal state on a basis of the extracted vascular index and a reference index based on indices extracted, using a method used to extract the vascular index, in advance from an area in chest X-ray images in a normal state corresponding to the area included in the third lung area, and an output controller that outputs, if it is determined that the area included in the third lung area is in an abnormal state, information indicating a result of the determination made by the determiner.

According to the fourth aspect, a third lung area including a first lung area where one or more of the lungs and the heart overlap and/or a second lung area where one of the lungs and the liver overlap is set and whether an area included in the third lung area is in an abnormal state is determined. According to the fourth aspect, therefore, whether there is an abnormality in an area included in the third lung area can be determined. If it is determined that there is an abnormality in the area included in the third lung area, information indicating a result of the determination made by the determiner is output. Useful information, therefore, can be provided for the user. As a result, the server apparatus according to the fourth aspect can not only provide useful information for an interpreter but also be used by a clinician or a radiologist to give a diagnosis or study by himself/herself or a medical student to be educated or study by himself/herself. With the server apparatus method according to the fourth aspect, an abnormality can be detected in the first lung area (an area in a chest X-ray image where one or more of the lungs and the heart overlap) and/or the second lung area (an area in a chest X-ray image where one of the lungs and the liver overlap) on the basis of a vascular index, the first and second lung areas being often not included as abnormality detection target areas in the case of abnormality detection techniques in conventional diagnosis aiding techniques for chest X-ray images.

A fifth aspect of the present disclosure is a method for detecting an abnormality. The method includes obtaining, using a computer, a chest X-ray image, determining, using the computer, whether an area included in a third lung area in the obtained chest X-ray image including a first lung area where one or more lungs and a heart overlap and/or a second lung area where one of the lungs and a liver overlap is in an abnormal state, and outputting, if determining that an area included in the third lung area is in an abnormal state, information indicating that the area included in the third lung area is abnormal using the computer.

According to the fifth aspect, whether there is an abnormality in an area included in a third lung area, which includes a first lung area where one or more of the lungs and the heart overlap and/or a second lung area where one of the lungs and the liver overlap, can be determined in an obtained chest X-ray image. If it is determined that there is an abnormality in the area included in the third lung area, information indicating that the area included in the third area is abnormal is output. Useful information, therefore, can be provided for the user. As a result, the method for detecting an abnormality according to the fifth aspect can not only provide useful information for an interpreter but also be used by a clinician or a radiologist to give a diagnosis or study by himself/herself or a medical student to be educated or study by himself/herself. With the method for detecting an abnormality according to the fifth aspect, an abnormality can be detected in the first lung area (an area in a chest X-ray image where one or more of the lungs and the heart overlap) and/or the second lung area (an area in a chest X-ray image where one of the lungs and the liver overlap) on the basis of a vascular index, the first and second lung areas being often not included as abnormality detection target areas in the case of abnormality detection techniques in conventional diagnosis aiding techniques for chest X-ray images.

The fifth aspect may further include, for example, detecting, in the obtained chest X-ray image using the computer, a first boundary line between an image of the one or more lungs and an image of the heart and/or a second boundary line between an image of one of the lungs and an image of the liver, setting, on a basis of the first boundary line and/or the second boundary line using the computer, the third lung area in the obtained chest X-ray image, and extracting, using the computer, a vascular index indicating density of at least one blood vessel in an area included in the third lung area.

In the determining, whether the area included in the third lung area is in an abnormal state may be determined on a basis of the vascular index and a reference index indicating density of at least one blood vessel in an area in chest X-ray images in a normal state corresponding to the area included in the third lung area.

According to this aspect, since a reference index indicating the density of at least one blood vessel in an area in chest X-ray images in a normal state corresponding to an area included in the third lung area is used, an abnormality can be detected more accurately.

A sixth aspect of the present disclosure is a method for processing information. The method includes obtaining, using a computer, a chest X-ray image, detecting, in the obtained chest X-ray image using the computer and a model constructed through machine learning before the detecting, boundary lines of images of anatomical structures whose ranges of X-ray transmittances are different from one another, setting, using the computer, a third lung area in the chest X-ray image including at least one of a first lung area where one or more lungs and a heart overlap or a second lung area where one of the lungs and a liver overlap on a basis of the detected boundary lines, extracting, using the computer, a vascular index indicating at least one of thickness or density of at least one pulmonary blood vessel present in an area included in the third lung area, and outputting, using the computer, the extracted vascular index.

According to the sixth aspect, boundary lines are detected while focusing upon various boundary lines drawn in chest X-ray images. A third lung area including a first lung area where one or more of the lungs and the heart overlap and/or a second lung area where one of the lungs and the liver overlap, therefore, can be set on the basis of the boundary lines. According to the sixth aspect, therefore, a vascular index indicating at least one of the thickness or density of at least one pulmonary blood vessel in an area included in the third lung area can be extracted. The extracted vascular index is then output. The vascular index in the area included in the third lung area, therefore, can be provided for the user. As a result, the user can use the vascular index in the area included in the third lung area. For example, the user can understand a state of the at least one pulmonary blood vessel in the area included in the third lung area in the chest X-ray image with an objective value using the vascular index in the area included in the third lung area. The user, therefore, can more accurately determine whether the state of the at least one pulmonary blood vessel is abnormal.

In the above first aspect, for example,
the first lung area may be a first area where a left lung included in the lungs and the heart overlap, a second area where a right lung included in the lungs and the heart overlap, or both the first area and the second area.

EMBODIMENTS

Embodiments of the present disclosure will be described hereinafter with reference to the drawings. In the drawings, the same components are given the same reference numerals, and description thereof is omitted as necessary.

First Embodiment

Figure 1:
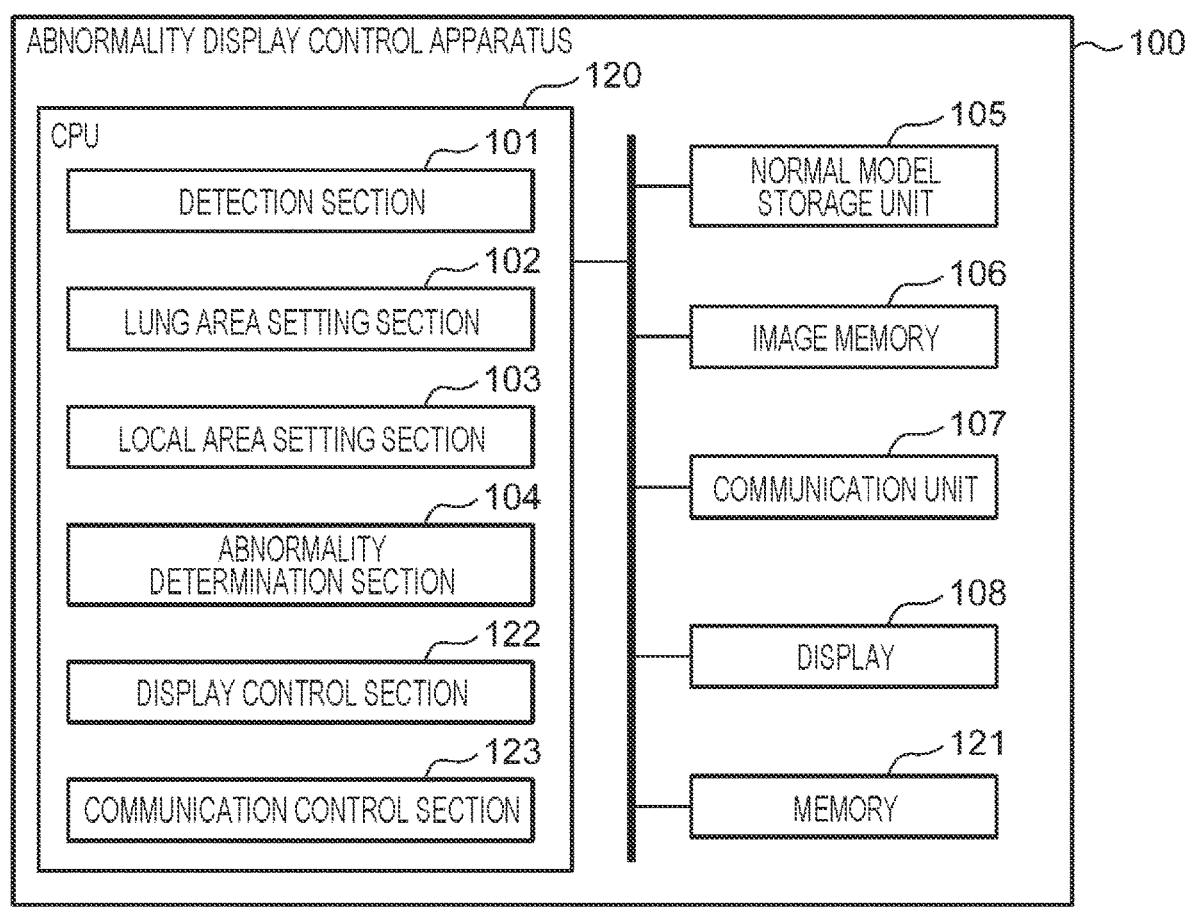
FIG. 1 is a block diagram of an abnormality display control apparatus according to a first embodiment.
Figure 2:
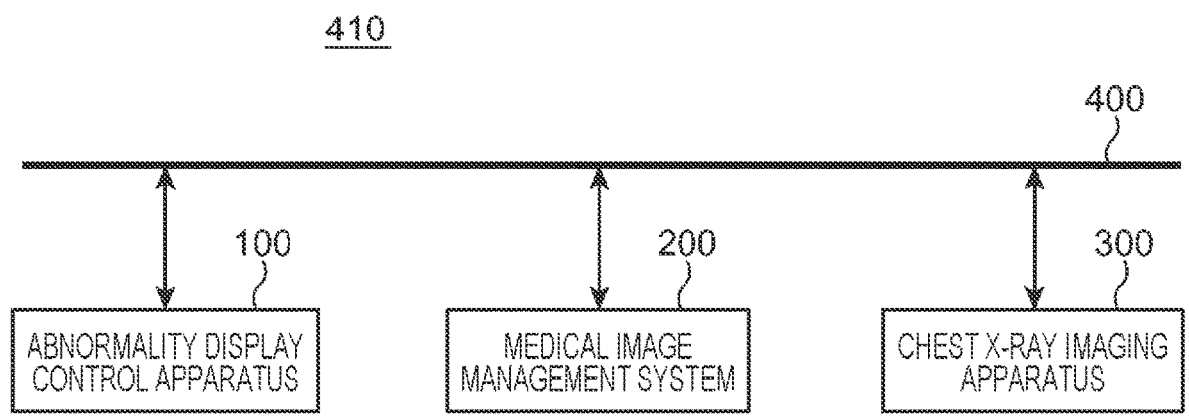
FIG. 2 is a block diagram of a network configuration in a medical facility according to the first embodiment.

FIG. 1 is a block diagram schematically illustrating the configuration of an abnormality display control apparatus 100 that executes a method for controlling display of an abnormality in a chest X-ray image. FIG. 2 is a block diagram schematically illustrating a network configuration 410 in a medical facility.

As illustrated in FIG. 2, the network configuration 410 in the medical facility includes an intranet 400. The abnormality display control apparatus 100, a medical image management system 200, and a chest X-ray imaging apparatus 300 are connected to the intranet 400. The medical image management system 200 saves and manages chest X-ray images, CT images, images generated as a result of magnetic resonance imaging (MRI), and the like. The chest X-ray imaging apparatus 300 captures a chest X-ray image of a patient or a person undergoing a medical examination. The chest X-ray image captured by the chest X-ray imaging apparatus 300 is transmitted to and saved in the medical image management system 200.

The abnormality display control apparatus 100, the medical image management system 200, and the chest X-ray imaging apparatus 300 need not necessarily be connected to the intranet 400 in the same medical facility. The abnormality display control apparatus 100 and the medical image management system 200 may be software operating on a data center server, a private cloud server, a public cloud server, or the like provided outside the medical facility, instead. The chest X-ray imaging apparatus 300 may be installed in a hospital or a vehicle used for a medical examination or the like, instead. The medical image management system 200 is, for example, a picture archiving and communication system (PACS).

As illustrated in FIG. 1, the abnormality display control apparatus 100 (an example of an abnormality detection apparatus) includes a normal model storage unit 105, an image memory 106, a communication unit 107, a display 108, a central processing unit (CPU) 120, and a memory 121. The abnormality display control apparatus 100 is achieved, for example, by a personal computer.

The communication unit 107 communicates with the medical image management system 200 and the like over the intranet 400. The normal model storage unit 105 is achieved, for example, by a hard disk or a semiconductor memory. The normal model storage unit 105 stores information for identifying a probability density function (described later with reference to FIG. 30) of an index and an expression for calculating an index at a time when each of predefined local areas (described later) is in a normal state. The information for identifying the probability density function will be described later. The expression for calculating an index refers to (i) an algorithm for extracting a linear structure (described later) from a local area and an expression for calculating an index obtained from the extracted linear structure or (ii) an algorithm for dimensionally reducing an image of a local area (a principal component analysis, a stacked autoencoder, a variational autoencoder, which will be described later, etc.) and an expression for calculating a reconstruction error in the image of the local area from the algorithm. In the present embodiment, the index indicates the thickness and/or density of blood vessels as described later, and also referred to as a "vascular index".

The image memory 106 is achieved, for example, by a hard disk or a semiconductor memory. The image memory 106 stores obtained target chest X-ray images. The display 108 is achieved, for example, by a liquid crystal monitor and used by a doctor or a radiographer, who is a user, to display a target chest X-ray image, which is a chest X-ray image to be read. The display 108 also displays medical record information regarding a patient for whom a target chest X-ray image has been captured, a report input screen for entering a result of an image diagnosis, and the like.

The memory 121 is achieved, for example, by a semiconductor memory. The memory 121 may be, for example, a read-only memory (ROM), a random-access memory (RAM), or an electrically erasable programmable ROM (EEPROM). The ROM of the memory 121 stores a control program according to the first embodiment for operating the CPU 120.

The CPU 120 executes the control program according to the first embodiment stored in the memory 121 to function as a detection section 101, a lung area setting section 102, a local area setting section 103, an abnormality determination section 104, a display control section 122, and a communication control section 123. The detection section 101 reads a target chest X-ray image saved in the image memory 106 and detects linear structures included in the read target chest X-ray image. The lung area setting section 102 sets an area defined by at least two of the linear structures detected by the detection section 101 as a lung area. The lung area may be a part of the lungs or the entirety of the lungs in the chest X-ray image. The local area setting section 103 divides the set lung area into local areas. The abnormality determination section 104 calculates an index for each of the local areas set by the local area setting section 103 and determines whether each of the local areas is in an abnormal state by comparing the probability density function of the index, which is stored in the normal model storage unit 105, at a time when the local area is in a normal state and the calculated index with each other. Functions of the display control section 122 and the communication control section 123 will be described later.

FIG. 3 is a flowchart schematically illustrating a process performed by the abnormality display control apparatus 100 according to the first embodiment. In step S50, the communication control section 123 (an example of an obtainer) obtains a target chest X-ray image, which is a chest X-ray image to be read, from the medical image management system 200 through the communication unit 107 and saves the obtained target chest X-ray image in the image memory 106. In step S100, the detection section 101 reads the target chest X-ray image from the image memory 106 and detects two or more predefined linear structures from the target chest X-ray image.

Here, an area or a boundary line in a chest X-ray image where an anatomical structure (e.g., an organ such as the heart) in a human body is drawn, an area or a boundary line in a chest X-ray image where a part of an anatomical structure in the human body is drawn, or a boundary line in a chest X-ray image where a boundary between anatomical structures in the human body whose X-ray transmittances are different from each other is drawn is defined as a "structure". Among such structures, especially a boundary line, an anatomical structure in the human body drawn as a line, and a part of an anatomical structure in the human body drawn as a line is defined as "linear structures". Structures that are not linear structures, that is, structures that are not regarded as being linear, are defined as "area structures". Even in the case of linear structures, some might have widths greater than one pixel in an image, and linear structures and area structures might not always be clearly distinguished from each other. By employing the following procedure, for example, linear structures and area structures can be distinguished from each other.

(i) Binarize an image (e.g., FIG. 4B or 5B) of an extracted structure using an appropriate threshold.

(ii) Perform thinning on the binarized image of the structure until the width is reduced to one pixel.

Figure 5A:
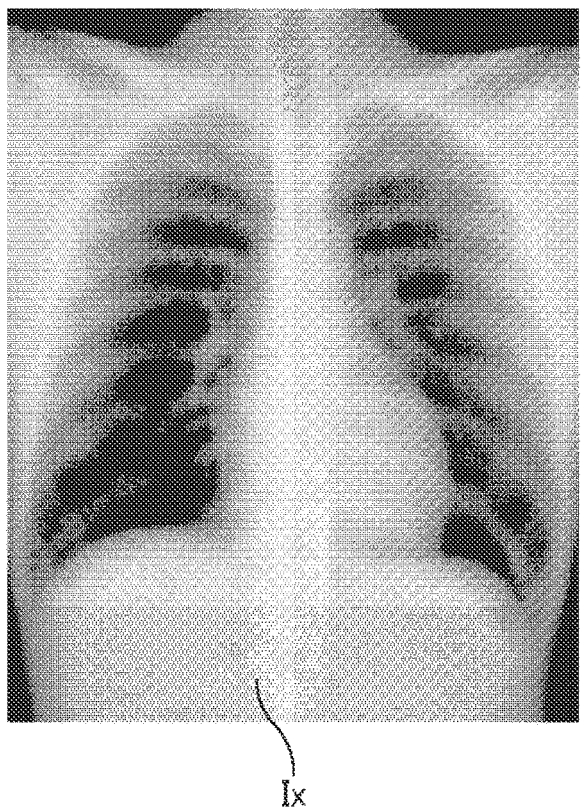
FIG. 5A is a diagram illustrating a chest X-ray image including a shadow of a right dorsal lung base.
Figure 5B:
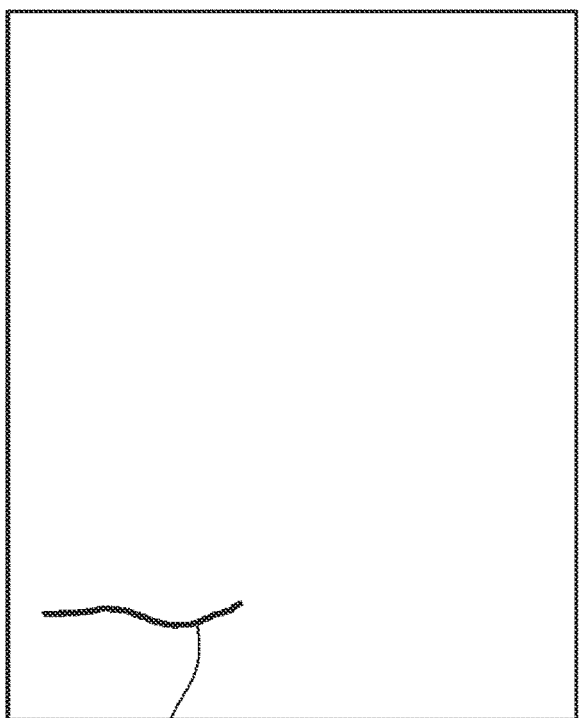
FIG. 5B is a diagram illustrating a mask image of the shadow of the right dorsal lung base.
Figure 5C:
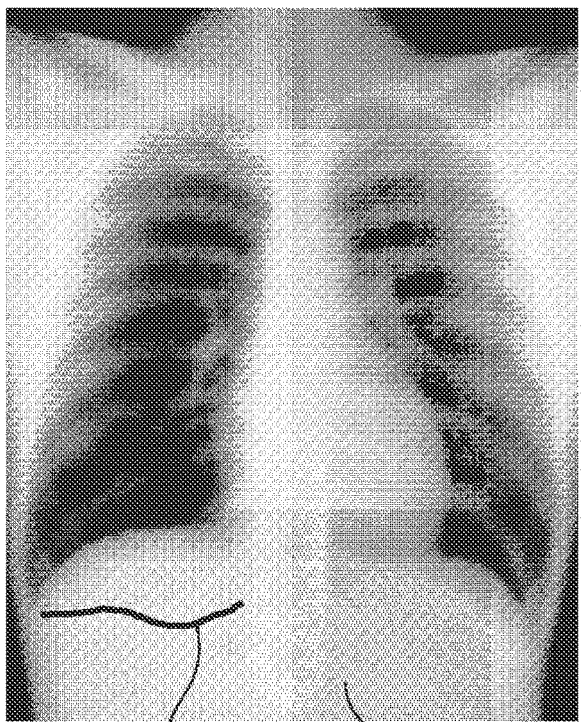
FIG. 5C is a diagram illustrating an image displayed by superimposing the mask image upon the chest X-ray image.
Figure 6A:
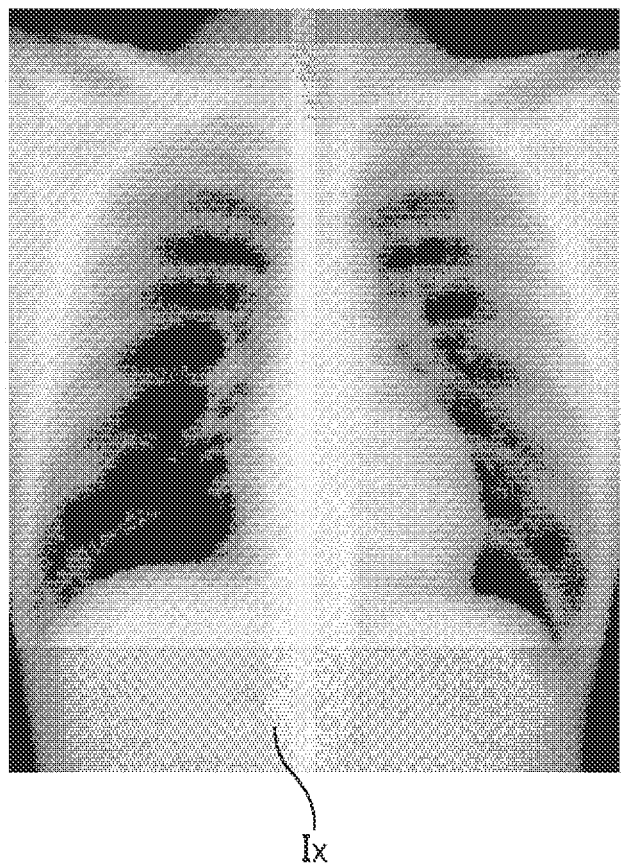
FIG. 6A is a diagram illustrating a chest X-ray image including a first thoracic vertebra.
Figure 6B:
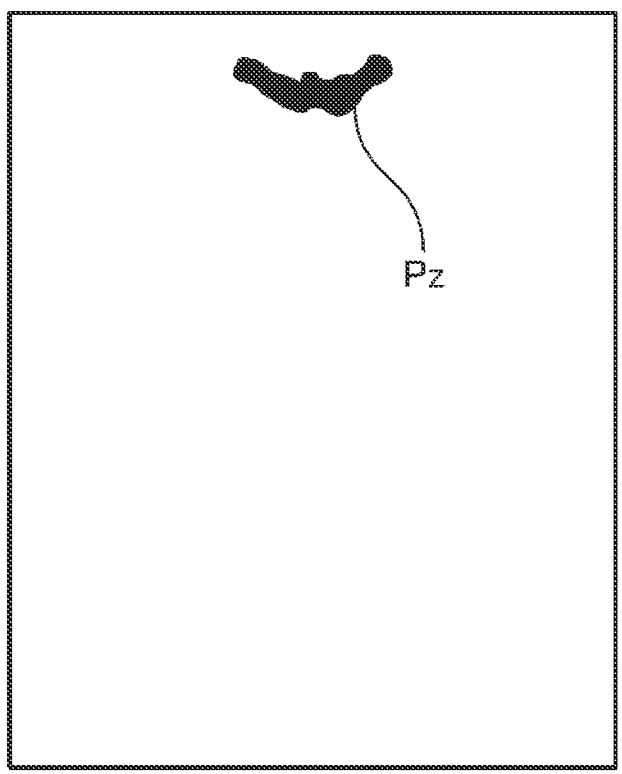
FIG. 6B is a diagram illustrating a mask image of the first thoracic vertebra.
Figure 6C:
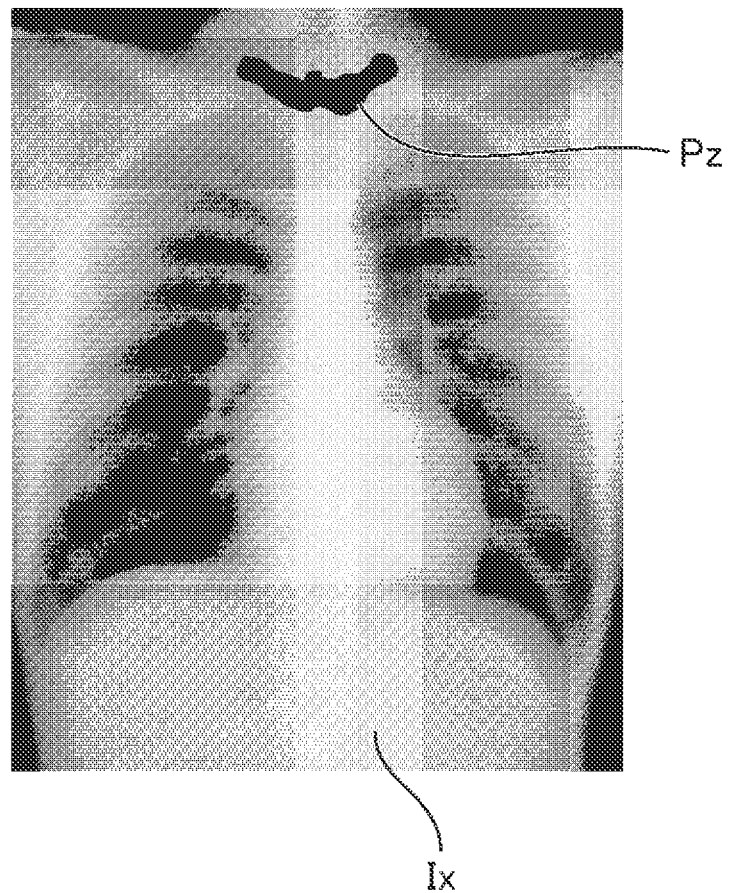
FIG. 6C is a diagram illustrating an image displayed by superimposing the mask image upon the chest X-ray image.

(iii) Calculate a ratio of the area of the structure in the image before the thinning to the area of the structure in the image after the thinning and determine, if the ratio is higher than or equal to a predetermined threshold, the structure to be a linear structure or, if not, the structure to be an area structure. The threshold may be set to an appropriate value with which a structure can be regarded as being linear. FIGS. 4A to 4C and 5A to 5C illustrate examples of linear structures, and FIGS. 6A to 6C illustrate an example of an area structure.

Figure 4A:
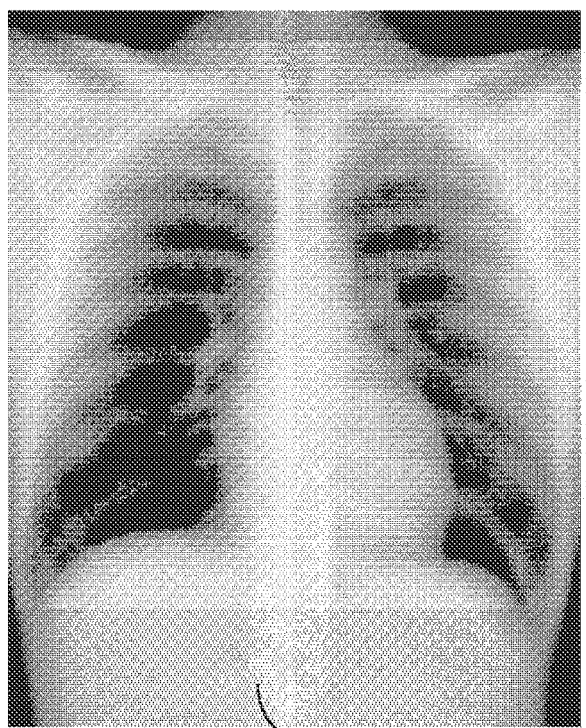
FIG. 4A is a diagram illustrating a chest X-ray image including a shadow of a descending aorta.
Figure 4B:
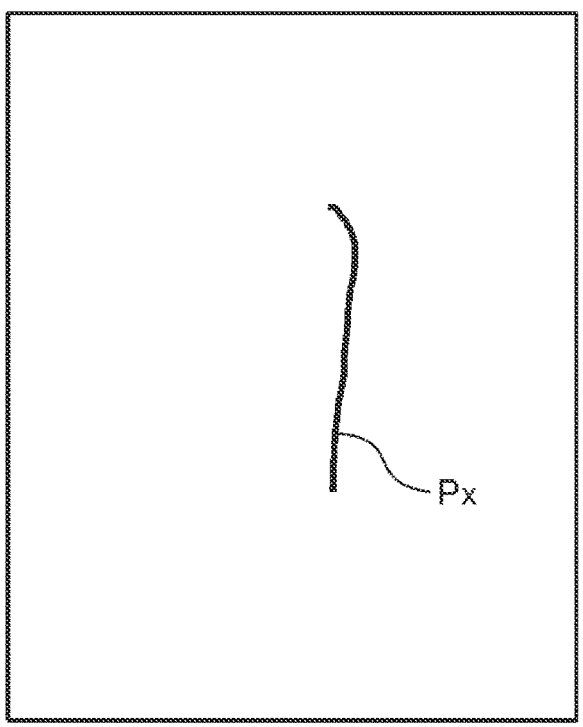
FIG. 4B is a diagram illustrating a mask image of the shadow of the descending aorta.
Figure 4C:
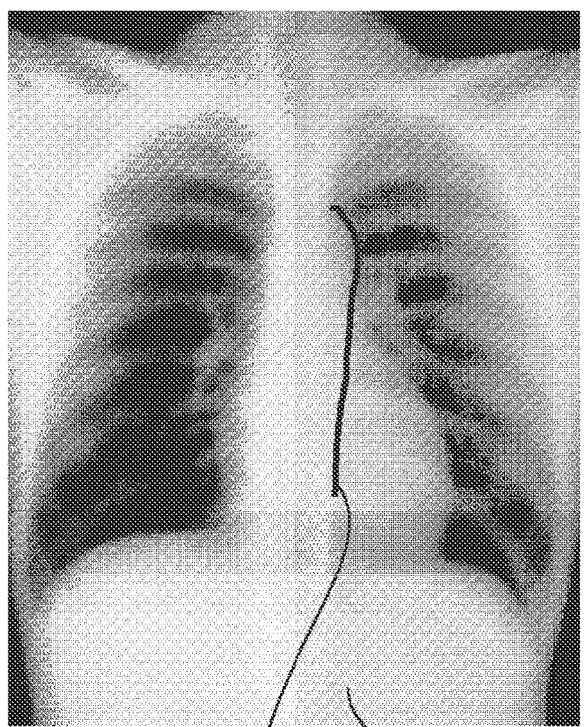
FIG. 4C is a diagram illustrating an image displayed by superimposing the mask image upon the chest X-ray image.

FIG. 4A is a diagram illustrating a chest X-ray image Ix including a shadow of a descending aorta (i.e., a boundary line drawn on the basis of a difference in X-ray transmittance between the descending aorta and a lung parenchyma). FIG. 4B is a diagram illustrating a mask image Px of the shadow of the descending aorta. FIG. 4C is a diagram illustrating an image displayed by superimposing the mask image Px illustrated in FIG. 4B upon the chest X-ray image Ix illustrated in FIG. 4A. FIG. 5A is a diagram illustrating the chest X-ray image Ix including a shadow of a right dorsal lung base (i.e., a boundary line drawn on the basis of a difference in X-ray transmittance between a dorsal bottom of the lung parenchyma and ventral organs). FIG. 5B is a diagram illustrating a mask image Py of the shadow of the right dorsal lung base. FIG. 5C is a diagram illustrating an image displayed by superimposing the mask image Py illustrated in FIG. 5B upon the chest X-ray image Ix illustrated in FIG. 5A. FIG. 6A is a diagram illustrating a chest X-ray image Ix including an area where a first thoracic vertebra is projected. FIG. 6B is a diagram illustrating a mask image Pz of the first thoracic vertebra. FIG. 6C is a diagram illustrating an image displayed by superimposing the mask image Pz illustrated in FIG. 6B upon the chest X-ray image Ix illustrated in FIG. 6A.

A mask image is a binary image expressing, in black, an area in a corresponding chest X-ray image where there is a structure and, in white, an area in the corresponding chest X-ray image where there is no structure. Alternatively, an area where there is a structure may be expressed in white, and an area where there is no structure may be expressed in black. When it is difficult for a person to find an area in an image where there is a structure, a mask image may be represented as a multi-valued (grayscale) image using an intermediate value indicating a possibility of presence. In order to set a multi-valued image, for example, a person who creates a mask image may set different levels of confidence, or binary mask images created by two or more persons may be averaged. Pairs of a chest X-ray image and a mask image corresponding to the chest X-ray image are used to construct the detection section 101 through machine learning, and the mask images are training data for the machine learning. A person with a medical background creates the mask images. The detection section 101 constructed through the machine learning reads a target chest X-ray image saved in the image memory 106, detects linear structures included in the read target chest X-ray image, and outputs a mask image indicating areas of the detected linear structures. In the present embodiment and later embodiments, the detection section 101 is an example of a "model".

In the present embodiment, a U-Net, which is disclosed in O. Ronneberger, P. Fischer, and T. Brox, "U-Net: Convolutional Networks for Biomedical Image Segmentation", Medical Image Computing and Computer-Assisted Intervention (MICCAI), Springer, LNCS, Vol. 9351: 234-241, 2015, is used as the detection section 101. The U-Net divides an input image into areas in units of pixels through semantic segmentation.

FIG. 7 is a diagram schematically illustrating the architecture of the U-Net. The U-Net is a convolutional neural network including an encoder ECD and a decoder DCD illustrated in FIG. 7. An input image is input to an input layer IL of the U-Net, and the U-Net outputs an output image from an output layer OL. A pair of input data and a mask image, which is training data, used to perform machine learning on the U-Net is, for example, a pair of the image illustrated in FIG. 4A and the image illustrated in FIG. 4B, a pair of the image illustrated in FIG. 5A and the image illustrated in FIG. 5B, or a pair of the image illustrated in FIG. 6A and the image illustrated in FIG. 6B.

Training data for the U-Net used to construct the detection section 101 that detects the shadow of the descending aorta from a target chest X-ray image is, for example, input data=the chest X-ray image Ix illustrated in FIG. 4A and training data=the mask image Px illustrated in FIG. 4B. When a target chest X-ray image is input to the detection section 101 that has been subjected to the machine learning and that detects the shadow of the descending aorta, the detection section 101 detects the shadow of the descending aorta from the input target chest X-ray image.

Training data for the U-Net used to construct the detection section 101 that detects the shadow of the right dorsal lung base from a target chest X-ray image is, for example, input data=the chest X-ray image Ix illustrated in FIG. 5A and training data=the mask image Py illustrated in FIG. 5B. When a target chest X-ray image is input to the detection section 101 that has been subjected to the machine learning and that detects the shadow of the right dorsal lung base, the detection section 101 detects the shadow of the right dorsal lung base from the input target chest X-ray image.

Training data for the U-Net used to construct the detection section 101 that detects the first thoracic vertebra from a target chest X-ray image is, for example, input data=the chest X-ray image Ix illustrated in FIG. 6A and training data=the mask image Pz illustrated in FIG. 6B. The detection section 101 that has been subjected to the machine learning and that detects the first thoracic vertebra reads a target chest X-ray image saved in the image memory 106, detects the first thoracic vertebra included in the read target chest X-ray image, and outputs an area image of the first thoracic vertebra.

The detection section 101 may be N U-Nets (N is an integer greater than or equal to 1) subjected to machine learning, that is, first to N-th U-Nets subjected to machine learning.

N pairs of a chest X-ray image and a corresponding mask image, that is, first to N-th pairs of a chest X-ray image and a mask image, may be prepared, and the first to N-th pairs of a chest X-ray image and a corresponding mask image may be used to perform machine learning on the first to N-th U-Nets, respectively. As a result, the N U-Nets subjected to machine learning are constructed.

The detection section 101 may be a U-Net subjected to machine learning, instead. In order to perform machine learning and construct the U-Net, N pairs of a chest X-ray image and a corresponding mask image may be used. That is, a U-Net may be constructed in such a way as to be able to perform multi-class segmentation, where a single U-Net detects N linear structures. Alternatively, another neural network such as one disclosed in L. Long, E. Shelhamer, and T. Darrell, "Fully Convolutional Networks for Semantic Segmentation", CVPR, 2015 may be used, instead, as an artificial neural network that performs semantic segmentation.

FIG. 3 will be referred to again. In step S200, the lung area setting section 102 (an example of a setter) sets a lung area, which is an area in the chest X-ray image where the lungs are projected, using the detected linear structures. FIGS. 8 to 13 illustrate examples where the lung area setting section 102 has set a lung area in the chest X-ray image.

Figure 11:
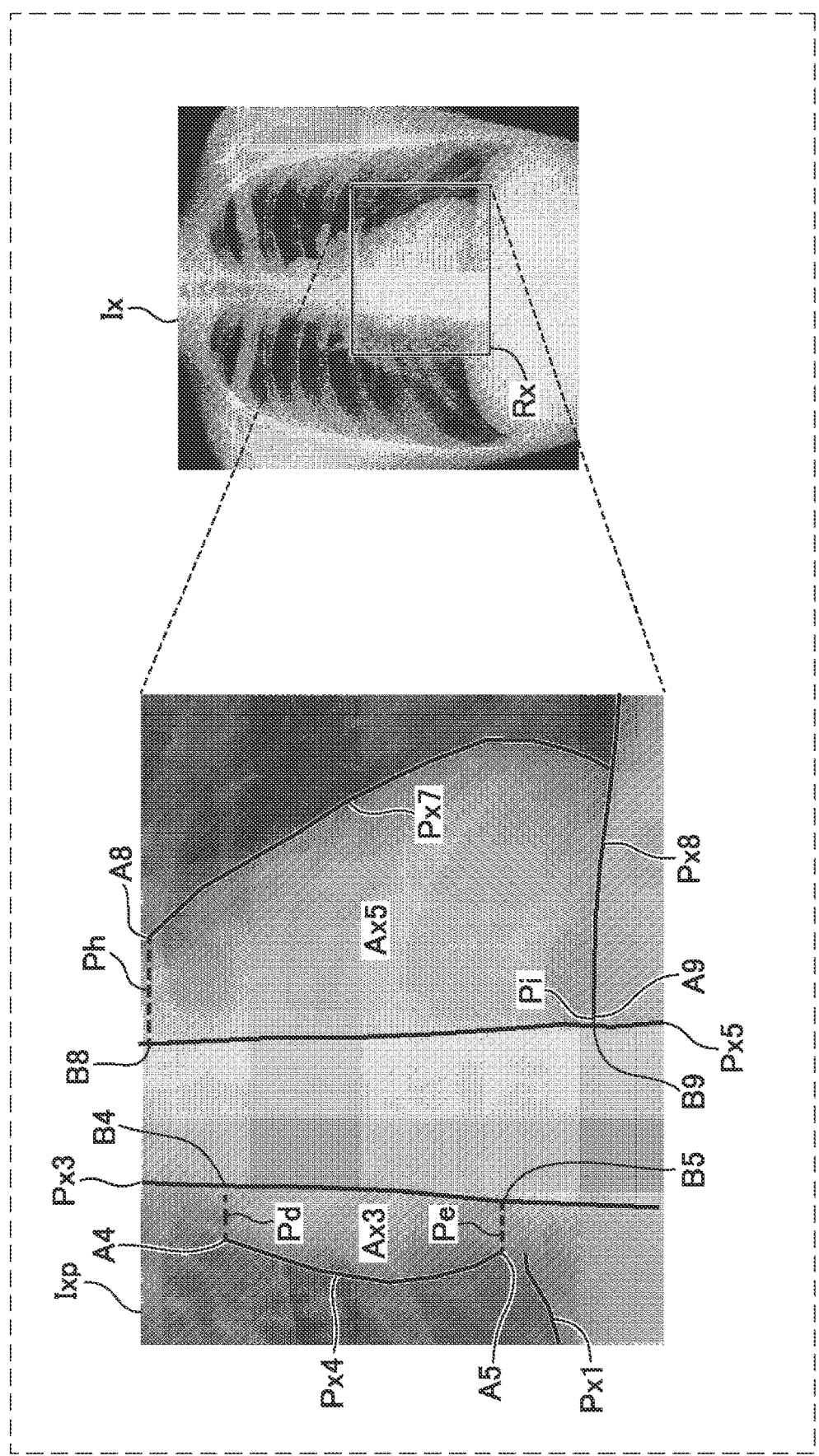
FIG. 11 is a diagram illustrating another example of the method for setting an area where one or more of the lungs and the heart overlap and the area.
Figure 12:
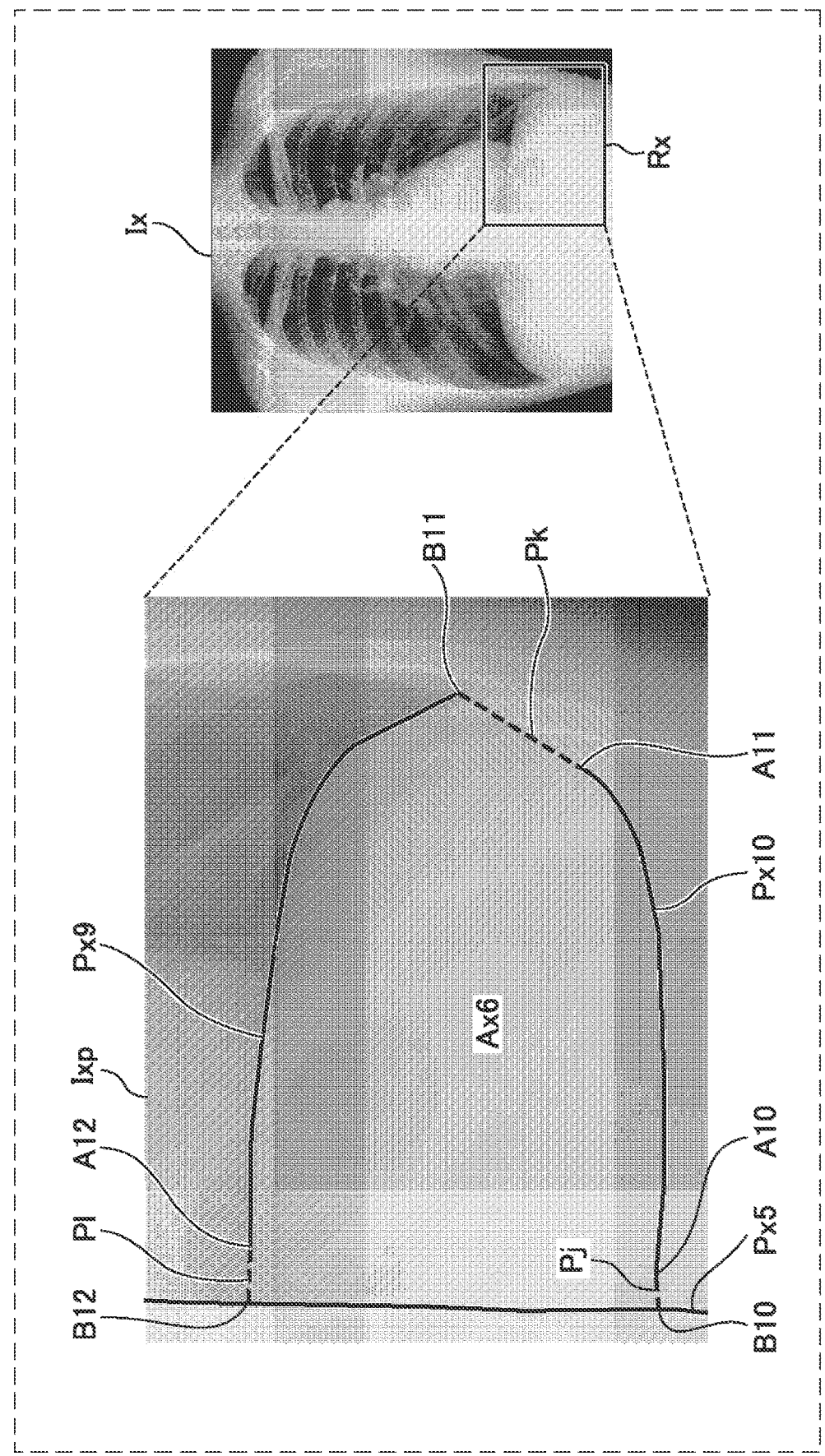
FIG. 12 is a diagram illustrating an example of a method for setting an area where one of the lungs and a stomach overlap and the area.
Figure 13:
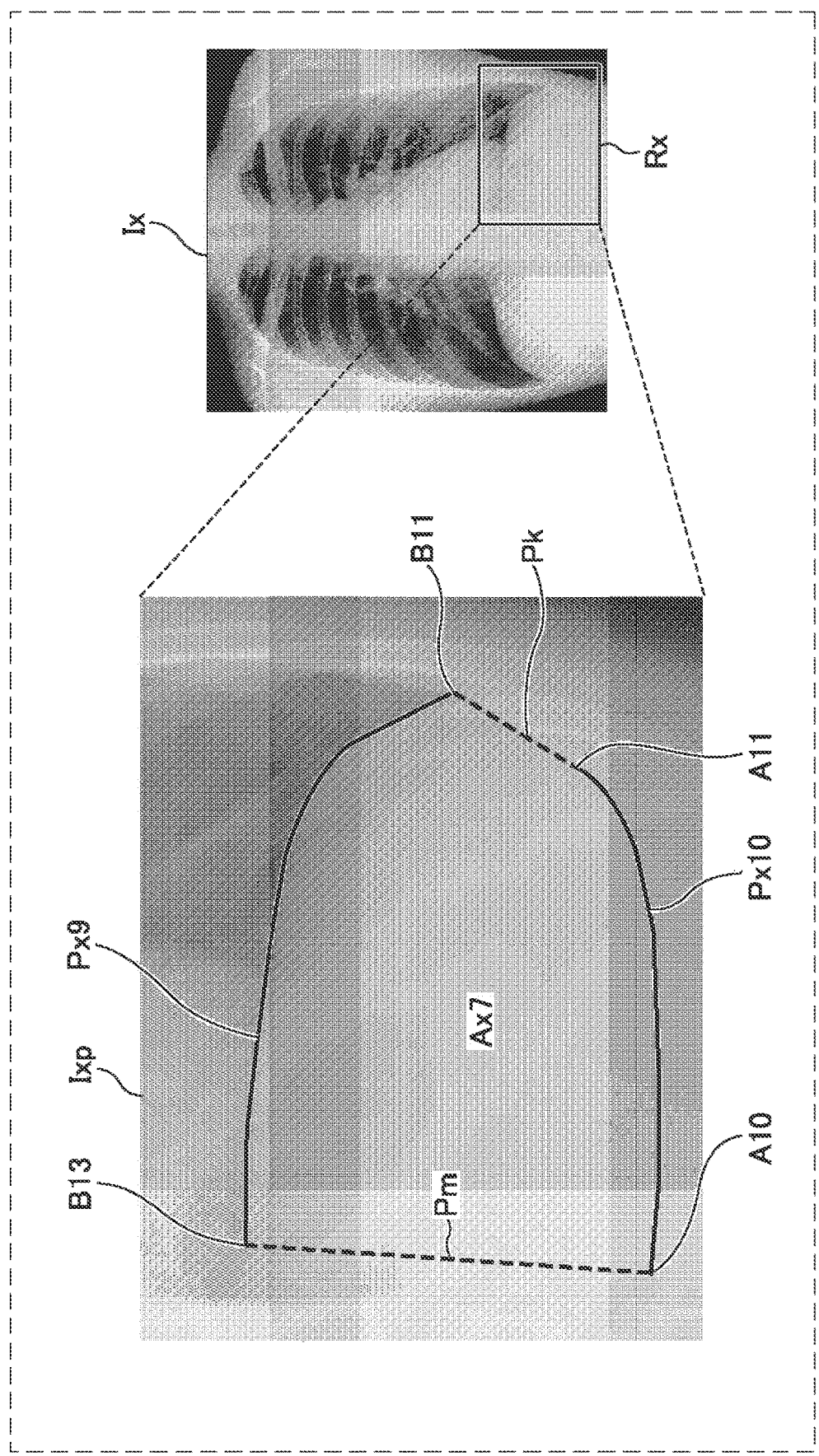
FIG. 13 is a diagram illustrating another example of the method for setting an area where one of the lungs and the stomach overlap and the area.

FIGS. 8 and 9 are diagrams illustrating examples of a method for setting an area in a chest X-ray image where one of the lungs and other organs, such as a liver and the diaphragm, overlap and the area. FIGS. 10 and 11 are diagrams illustrating examples of a method for setting an area in a chest X-ray image where one or more of the lungs and another organ, such as the heart, overlap and the area. FIGS. 12 and 13 are diagrams illustrating examples of a method for setting an area in a chest X-ray image where one of the lungs and another organ, such as a stomach, overlap and the area.

In FIG. 8, an image Ix is a chest X-ray image to be used by a doctor for a diagnosis (can also be referred to as a "target to be processed" in the present embodiment), and an image Ixp is obtained by enlarging an area Rx in the image Ix. Linear structures Px1, Px2, and Px3 are detected by the detection section 101 and indicate a right diaphragm dome shadow, a right dorsal lung base shadow, and a right edge of a vertebral body, respectively. The lung area setting section 102 sets, using these linear structures detected by the detection section 101, an area in the image Ixp where one of the lungs and other organs, such as the liver and the diaphragm, overlap. When a linear structure is broken in the middle, the lung area setting section 102 connects an end of one of the linear structures and a point on the linear structure closest to the end to each other with a straight interpolation line. When linear structures are separate from each other, the lung area setting section 102 connects an end of one of the linear structures and a point on another linear structure closest to the end to each other with a straight interpolation line. A straight line connecting an end A1 of the linear structure Px1 closest to the linear structure Px2 and a point B1 on the linear structure Px2 closest to the end A1 to each other is an interpolation line Pa. A straight line connecting another end A2 of the linear structure Px1 closest to the linear structure Px3 and a point B2 on the linear structure Px3 closest to the end A2 to each other is an interpolation line Pb. A closed area Ax1 is thus defined by the linear structures Px1, Px2, and Px3 and the interpolation lines Pa and Pb. The lung area setting section 102 sets the area Ax1 as an area included in an area indicating an image of the lungs. Similarly, FIGS. 9 to 13 illustrate other examples of the setting of a lung area.

In FIG. 9, the image Ix is a chest X-ray image to be used by a doctor for a diagnosis (can also be referred to as a "target to be processed" in the present embodiment), and the image Ixp is obtained by enlarging the area Rx in the image Ix. The linear structures Px1 and Px2 are detected by the detection section 101 and indicate the right diaphragm dome shadow and the right dorsal lung base shadow, respectively. The lung area setting section 102 sets, using these linear structures detected by the detection section 101, an area in the image Ixp where one of the lungs and other organs, such as the liver and the diaphragm, overlap. When a linear structure is broken in the middle, the lung area setting section 102 connects an end of one of the linear structures and a point on the linear structure closest to the end to each other with a straight interpolation line. When linear structures are separate from each other, the lung area setting section 102 connects an end of one of the linear structures and a point on another linear structure closest to the end to each other with a straight interpolation line. The straight line connecting the end A1 of the linear structure Px1 closest to the linear structure Px2 and the point B1 on the linear structure Px2 closest to the end A1 to each other is the interpolation line Pa. A straight line connecting the other end A2 of the linear structure Px1 closest to the linear structure Px2 and a point B3 on the linear structure Px2 closest to the end A2 to each other is an interpolation line Pc. A closed area Ax2 is thus defined by the linear structures Px1 and Px2 and the interpolation lines Pa and Pc. The lung area setting section 102 sets the area Ax2 as an area included in the area indicating the image of the lungs.

In FIG. 10, the image Ix is a chest X-ray image to be used by a doctor for a diagnosis (can also be referred to as a "target to be processed" in the present embodiment), and an image Ixp is obtained by enlarging an area Rx in the image Ix. Linear structures Px1, Px3, Px4, Px6, Px7, and Px8 are detected by the detection section 101 and indicate the right diaphragm dome shadow, the right edge of the vertebral body, a right atrium shadow, a descending aorta shadow, a left ventricle shadow, and a left diaphragm dome shadow, respectively. The lung area setting section 102 sets, using these linear structures detected by the detection section 101, an area in the image Ixp where one or more of the lungs and another organ, such as the heart, overlap. When a linear structure is broken in the middle, the lung area setting section 102 connects an end of one of the linear structures and a point on the linear structure closest to the end to each other with a straight interpolation line. When linear structures are separate from each other, the lung area setting section 102 connects an end of one of the linear structures and a point on another linear structure closest to the end to each other with a straight interpolation line. A straight line connecting an end A4 of the linear structure Px4 closest to the linear structure Px3 and a point B4 on the linear structure Px3 closest to the end A4 to each other is an interpolation line Pd. A straight line connecting another end A5 of the linear structure Px4 closest to the linear structure Px3 and a point B5 on the linear structure Px3 closest to the end A5 to each other is an interpolation line Pe. A straight line connecting an end A6 of the linear structure Px7 closest to the linear structure Px6 and a point B6 on the linear structure Px6 closest to the end A6 to each other is an interpolation line Pf. A straight line connecting an end A7 of the linear structure Px6 closest to the linear structure Px8 and a point B7 on the linear structure Px8 closest to the end A7 to each other is an interpolation line Pg. A closed area Ax3 is thus defined by the linear structures Px4 and Px3 and the interpolation lines Pd and Pe, and a closed area Ax4 is defined by the linear structures Px6, Px7, and Px8 and the interpolation lines Pf and Pg. The lung area setting section 102 sets the areas Ax3 and Ax4 as areas included in the area indicating the image of the lungs.

In FIG. 11, the image Ix is a chest X-ray image to be used by a doctor for a diagnosis (can also be referred to as a "target to be processed" in the present embodiment), and the image Ixp is obtained by enlarging the area Rx in the image Ix. Linear structures Px1, Px3, Px4, Px5, Px7, and Px8 are detected by the detection section 101 and indicate the right diaphragm dome shadow, the right edge of the vertebral body, the right atrium shadow, a left edge of the vertebral body, the left ventricle shadow, and the left diaphragm dome shadow, respectively. The lung area setting section 102 sets, using these linear structures detected by the detection section 101, an area in the image Ixp where one or more of the lungs and another organ, such as the heart, overlap. When a linear structure is broken in the middle, the lung area setting section 102 connects an end of one of the linear structures and a point on the linear structure closest to the end to each other with a straight interpolation line. When linear structures are separate from each other, the lung area setting section 102 connects an end of one of the linear structures and a point on another linear structure closest to the end to each other with a straight interpolation line. The straight line connecting the end A4 of the linear structure Px4 closest to the linear structure Px3 and the point B4 on the linear structure Px3 closest to the end A4 to each other is the interpolation line Pd. The straight line connecting the other end A5 of the linear structure Px4 closest to the linear structure Px3 and the point B5 on the linear structure Px3 closest to the end A5 to each other is the interpolation line Pe. A straight line connecting an end A8 of the linear structure Px7 closest to the linear structure Px5 and a point B8 on the linear structure Px5 closest to the end A8 to each other is an interpolation line Ph. A straight line connecting an end A9 of the linear structure Px8 closest to the linear structure Px5 and a point B9 on the linear structure Px5 closest to the end A9 to each other is an interpolation line Pi. The closed area Ax3 is thus defined by the linear structures Px4 and Px3 and the interpolation lines Pd and Pe, and a closed area Ax5 is defined by the linear structures Px5, Px7, and Px8 and the interpolation lines Ph and Pi. The lung area setting section 102 sets the areas Ax3 and Ax5 as areas included in the area indicating the image of the lungs. When linear structures detected by the detection section 101 are connected to each other from the start, interpolation lines need not be used.

In FIG. 12, the image Ix is a chest X-ray image to be used by a doctor for a diagnosis (can also be referred to as a "target to be processed" in the present embodiment), and an image Ixp is obtained by enlarging an area Rx in the image Ix. Linear structures Px5, Px9, and Px10 are detected by the detection section 101 and indicate the left edge of the vertebral body, the left diaphragm dome shadow, and a left dorsal lung base shadow, respectively. The lung area setting section 102 sets, using these linear structures detected by the detection section 101, an area in the image Ixp where one of the lungs and other organs, such as the stomach and the diaphragm, overlap. When a linear structure is broken in the middle, the lung area setting section 102 connects an end of one of the linear structures and a point on the linear structure closest to the end to each other with a straight interpolation line. When linear structures are separate from each other, the lung area setting section 102 connects an end of one of the linear structures and a point on another linear structure closest to the end to each other with a straight interpolation line. A straight line connecting an end A10 of the linear structure Px10 closest to the linear structure Px5 and a point B10 on the linear structure Px5 closest to the end A10 to each other is an interpolation line Pj. A straight line connecting another end A11 of the linear structure Px10 closest to the linear structure Px9 and a point B11 on the linear structure Px9 closest to the end A11 to each other is an interpolation line Pk. A straight line connecting an end A12 of the linear structure Px9 closest to the linear structure Px5 and a point B12 on the linear structure Px5 closest to the end A12 to each other is an interpolation line Pl. A closed area Ax6 is thus defined by the linear structures Px5, Px9, and Px10 and the interpolation lines Pj, Pk, and Pl. The lung area setting section 102 sets the area Ax6 as an area included in the area indicating the image of the lungs.

In FIG. 13, the image Ix is a chest X-ray image to be used by a doctor for a diagnosis (can also be referred to as a "target to be processed" in the present embodiment), and the image Ixp is obtained by enlarging the area Rx in the image Ix. The linear structures Px9 and Px10 are detected by the detection section 101 and indicate the left diaphragm dome shadow and the left dorsal lung base shadow, respectively. The lung area setting section 102 sets, using these linear structures detected by the detection section 101, an area in the image Ixp where one of the lungs and other organs, such as the stomach and the diaphragm, overlap. When a linear structure is broken in the middle, the lung area setting section 102 connects an end of one of the linear structures and a point on the linear structure closest to the end to each other with a straight interpolation line. When linear structures are separate from each other, the lung area setting section 102 connects an end of one of the linear structures and a point on another linear structure closest to the end to each other with a straight interpolation line. A straight line connecting the end A10 of the linear structure Px10 closest to the linear structure Px9 and a point B13 on the linear structure Px9 closest to the end A10 to each other is an interpolation line Pm. The straight line connecting the other end A11 of the linear structure Px10 closest to the linear structure Px9 and the point B11 on the linear structure Px9 closest to the end A11 to each other is the interpolation line Pk. A closed area Ax7 is thus defined by the linear structures Px9 and Px10 and the interpolation lines Pk and Pm. The lung area setting section 102 sets the area Ax7 as an area included in the area indicating the image of the lungs.

The detection of the linear structure Px2 (the right dorsal lung base shadow; FIGS. 8 and 9) and the linear structure Px10 (the left dorsal lung base shadow; FIGS. 12 and 13) might fail due to an insufficient luminance contrast in the detection of linear structures in step S100 (FIG. 3) depending on setting values during imaging, such as a dose of X-rays, setting values during image processing after the imaging, such as contrast conversion, and physical features of a subject (especially X-ray scattering in abdominal fat due to obesity). The lung area setting section 102, therefore, may calculate a degree of reliability indicating how probable a linear structure detected by the detection section 101 is.

If a calculated degree of reliability is higher than a certain threshold (first threshold), the lung area setting section 102 uses a linear structure (e.g., the right dorsal lung base shadow) detected by the detection section 101 in setting of an area (an example of a second lung area) where one of the lungs and other organs, such as the diaphragm and the liver, overlap. If a calculated degree of reliability is not higher than the certain threshold, on the other hand, the lung area setting section 102 may estimate a linear structure (e.g., the right dorsal lung base shadow) on the basis of a position of another certain anatomical structure detected by the detection section 101 and set the second lung area using the estimated linear structure (e.g., the right dorsal lung base shadow).

If a calculated degree of reliability is higher than another certain threshold (second threshold), the lung area setting section 102 uses a linear structure (e.g., the left dorsal lung base shadow) detected by the detection section 101 in setting of an area (an example of a fourth lung area) where one of the lungs and other organs, which may be abdominal organs such as the diaphragm and the stomach, overlap. If a calculated degree of reliability is not higher than the other certain threshold, the lung area setting section 102 may estimate a linear structure (e.g., the left dorsal lung base shadow) on the basis of a position of another certain anatomical structure detected by the detection section 101 and set the fourth lung area using the estimated linear structure (e.g., the left dorsal lung base shadow).

The linear structures to be estimated are not limited to the left and right dorsal lung base shadows, and other linear structures may be estimated, instead. The other linear structures may be, for example, the left and right diaphragm domes. A reason why the left and right diaphragm domes are estimated is that, especially in the case of women, the reliability of detection of the left and right diaphragm domes might decrease due to an overlap in a chest X-ray image between shadows of breasts and the shadows of the left and right diaphragm domes. A reason why the left diaphragm dome is estimated is that, regardless of gender, the reliability of detection of the left diaphragm dome might decrease due to a stomach bubble in an image observed near the left diaphragm dome.

A value of the output layer of the neural network, for example, may be used as a degree of reliability indicating how probable a linear structure detected by the detection section 101 is. In the case of the U-Net illustrated in FIG. 7, for example, the user sets, in the output layer OL, a mask image to be detected as training data during machine learning. More specifically, the user sets, in the output layer OL, training data in which, for example, a value of an area in the mask image Px expressed in black in FIG. 4B is 1.0 and a value of a background area expressed in white is 0.0. When the user inputs an unknown chest X-ray image to an input layer IL of a U-Net (i.e., the detection section 101 that detects the shadow of the descending aorta) subjected to machine learning and the U-Net detects the anatomical structure illustrated in FIG. 4B, an output value output to an output layer OL of the U-Net falls within a range of 0.0 to 1.0 at each of pixels. In this case, as the output value becomes closer to 1.0, it can be interpreted that the U-Net is more confident, and as the output value becomes closer to 0.0, it can be interpreted that the U-Net is less confident. Areas that are close to each other in an image and whose output values are larger than 0.0 and smaller than or equal to 1.0, therefore, may be regarded as areas corresponding to a certain anatomical structure, and an average of the output values can be used as a degree of reliability for the anatomical structure.

Alternatively, the lung area setting section 102 can calculate a degree of reliability indicating how probable a linear structure detected by the detection section 101 is by comparing an index such as a position or area of the linear structure with a probability density function of the index such as a position or area obtained in advance on the basis of a large number of normal cases.

A positional index of a linear structure is obtained as follows. A large number of binary mask images such as those illustrated in FIGS. 4B, 5B, and 6B are prepared. Coordinates (GXpj, GYpj) of a center of gravity of a mask image are calculated for each structure Pp and for each sample j, and these two-dimensional coordinates of the center of gravity are used as a positional index. The lung area setting section 102 can thus calculate a degree of reliability indicating how probable a linear structure detected by the detection section 101 is by comparing an index with a two-dimensional probability density function of the coordinates (GXpj, GYpj) of the center of gravity calculated from training binary mask images.

In order to absorb positional deviations during imaging performed by the chest X-ray imaging apparatus 300 and differences in physical features between subjects, bones (ribs, thoracic vertebrae, etc.) that are hardly affected by diseases compared to the lungs and that are not easily affected by the attitude of subjects during imaging may be detected and normalized to standard positions and physical features. An index may then be compared with a two-dimensional probability density function of normalized coordinates (NGXpj, NGYpj) of the center of gravity.

The lung area setting section 102 calculates coordinates of a center of gravity of a mask image of a structure Pp detected by the detection section 101. The lung area setting section 102 calculates a degree of reliability indicating how probable the linear structure detected by the detection section 101 is by comparing the calculated coordinates of the center of gravity with the two-dimensional probability density function of the center of gravity corresponding to the structure Pp saved in the normal model storage unit 105.

For example, an area index of a linear structure is obtained as follows. A large number of binary mask images such as those illustrated in FIGS. 4B, 5B, and 6B are prepared. An area Apj of a mask image is calculated for each structure Pp and for each sample j. This area is used as an index. A one-dimensional probability density function of the area Apj calculated from training binary mask images is thus obtained and stored in the normal model storage unit 105 in advance.

The lung area setting section 102 calculates area from a mask image of a structure Pp detected by the detection section 101. The lung area setting section 102 calculates a degree of reliability indicating how probable the linear structure detected by the detection section 101 is by comparing the calculated area with the one-dimensional probability density function of the area corresponding to the structure Pp saved in the normal model storage unit 105. As the area, the area of pixels constituting the structure Pp can be used. Alternatively, the number of pixels constituting the structure Pp may be used as the area.

When a detection target is a linear structure, the lung area setting section 102 may calculate a degree of reliability using the length of the linear structure detected by the detection section 101 after performing thinning in an area of the linear structure, instead of area. When a detection target is the left dorsal lung base or a right dorsal lung base, the lung area setting section 102 may calculate a degree of reliability indicating how probable a linear structure detected by the detection section 101 is by determining, on the basis of a standard deviation of pixel values or the like, whether there is enough contrast in an area under the left diaphragm dome shadow, where the left dorsal lung base is supposed to be present, or an area under the right diaphragm dome shadow, where the right dorsal lung base is supposed to be present, in a chest X-ray image (e.g., whether the standard deviation of pixel values is larger than or equal to a certain value).

Figure 14:
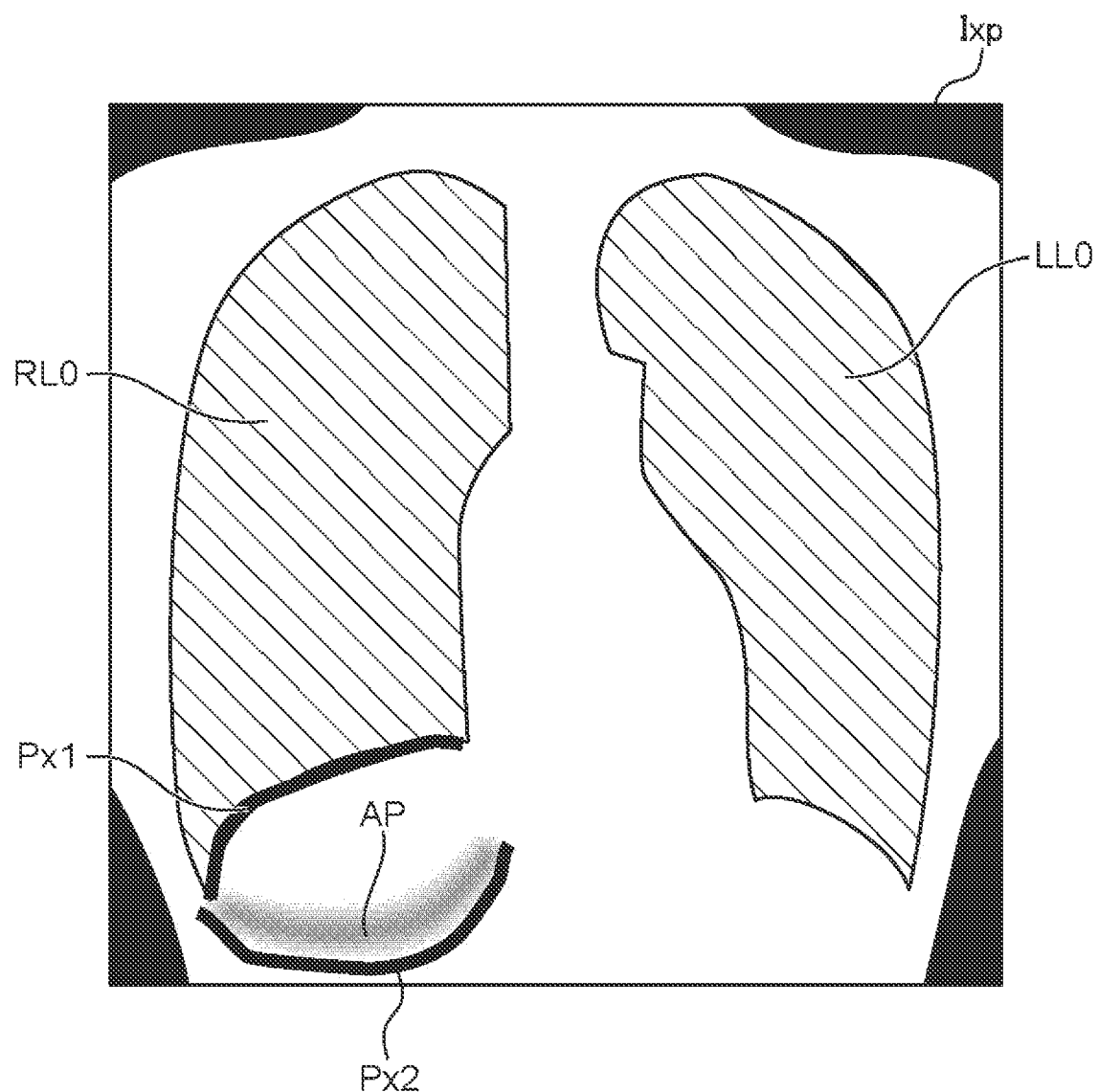
FIG. 14 is a diagram illustrating a method for estimating a right dorsal lung base shadow.

FIG. 14 is a diagram illustrating a method for estimating the right dorsal lung base shadow in a chest X-ray image. In FIG. 14, a right lung area RL0 and a left lung area LL0 indicate the image of the lungs in a chest X-ray image Ixp obtained as a result of threshold processing of pixel shading values. The method for estimating the right dorsal lung base shadow on the basis of a position of another certain anatomical structure detected by the detection section 101 will be described with reference to FIG. 14. For example, a positional relationship between the right diaphragm dome shadow and the right dorsal lung base shadow is obtained from a large number of normal cases and saved in the memory 121 in advance. As illustrated in FIG. 14, first, the lung area setting section 102 finds, on the basis of the positional relationship, an area AP in a right diaphragm dome shadow Px1 detected by the detection section 101 where a possibility of presence of the right dorsal lung base is higher than or equal to a certain value. Next, the lung area setting section 102 estimates a lower edge of the area AP to be a right dorsal lung base shadow Px2.

The left dorsal lung base shadow is harder to detect than the right dorsal lung base shadow due to presence of a stomach bubble (air or gas in the stomach). If a degree of reliability of the left dorsal lung base shadow is lower than or equal to the threshold (second threshold), the lung area setting section 102 may estimate the left dorsal lung base shadow using the method described with reference to FIG. 14. Alternatively, the lung area setting section 102 may estimate, as the left dorsal lung base shadow, a line symmetrical to the right dorsal lung base shadow across a central line of an area VT (FIG. 16) indicating an image of vertebrae (the thoracic vertebrae and lumbar vertebrae), the central line being regarded as a straight line in this case.

Figure 15:
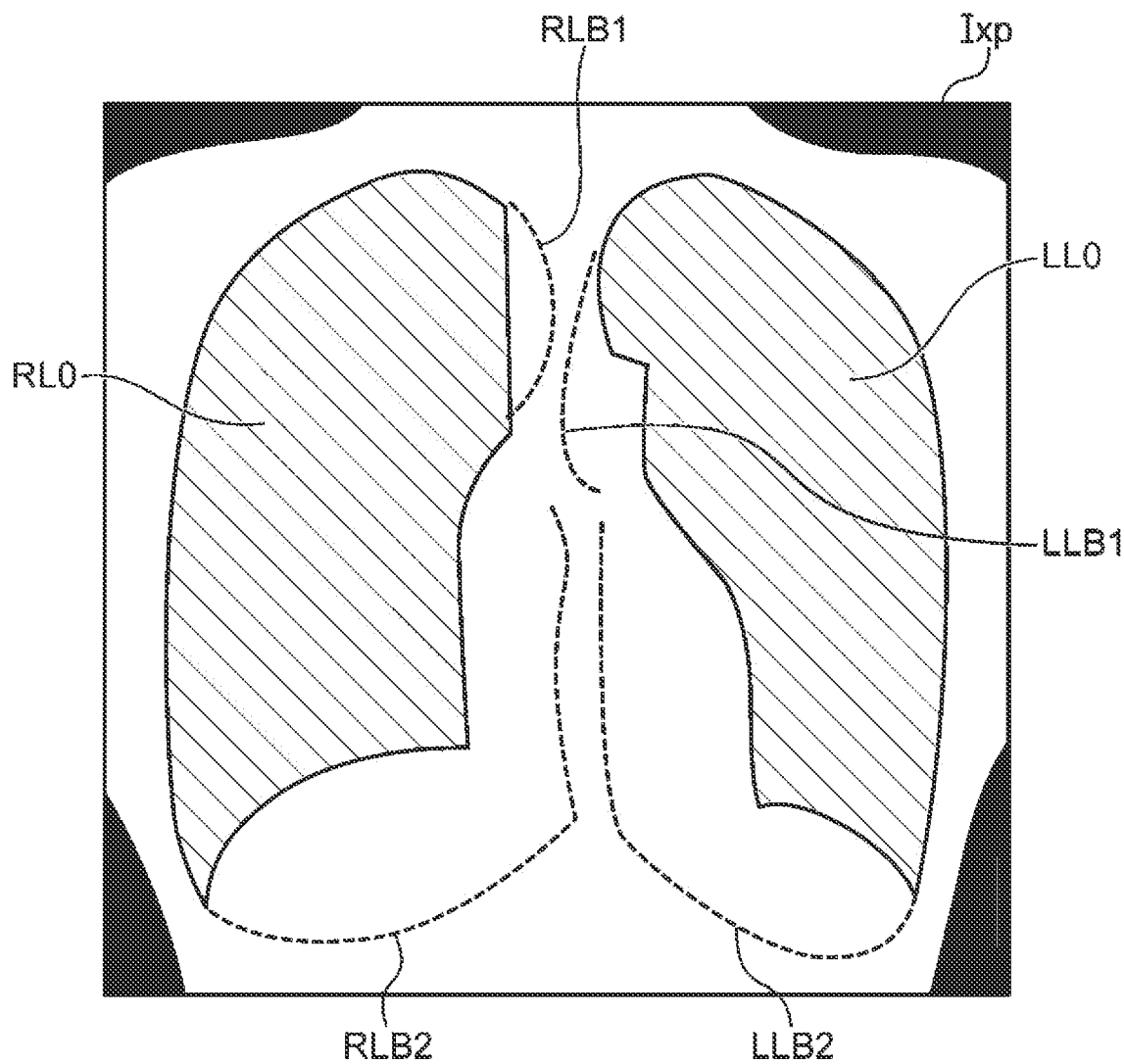
FIG. 15 is a diagram illustrating an area in a chest X-ray image where the lungs are present.
Figure 16:
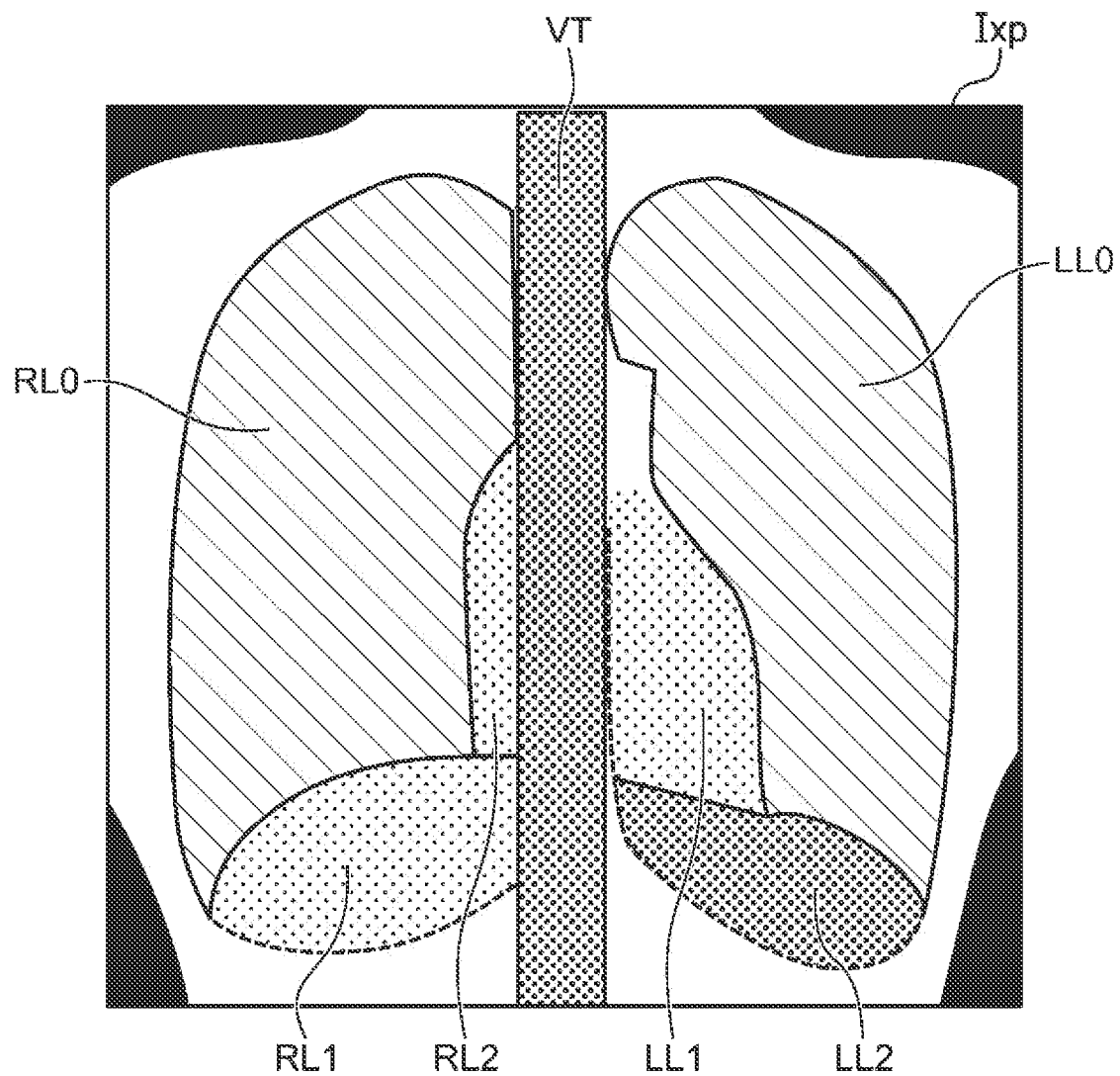
FIG. 16 is a diagram illustrating a lung area overlapping the heart and a lung area overlapping the liver.
Figure 17:
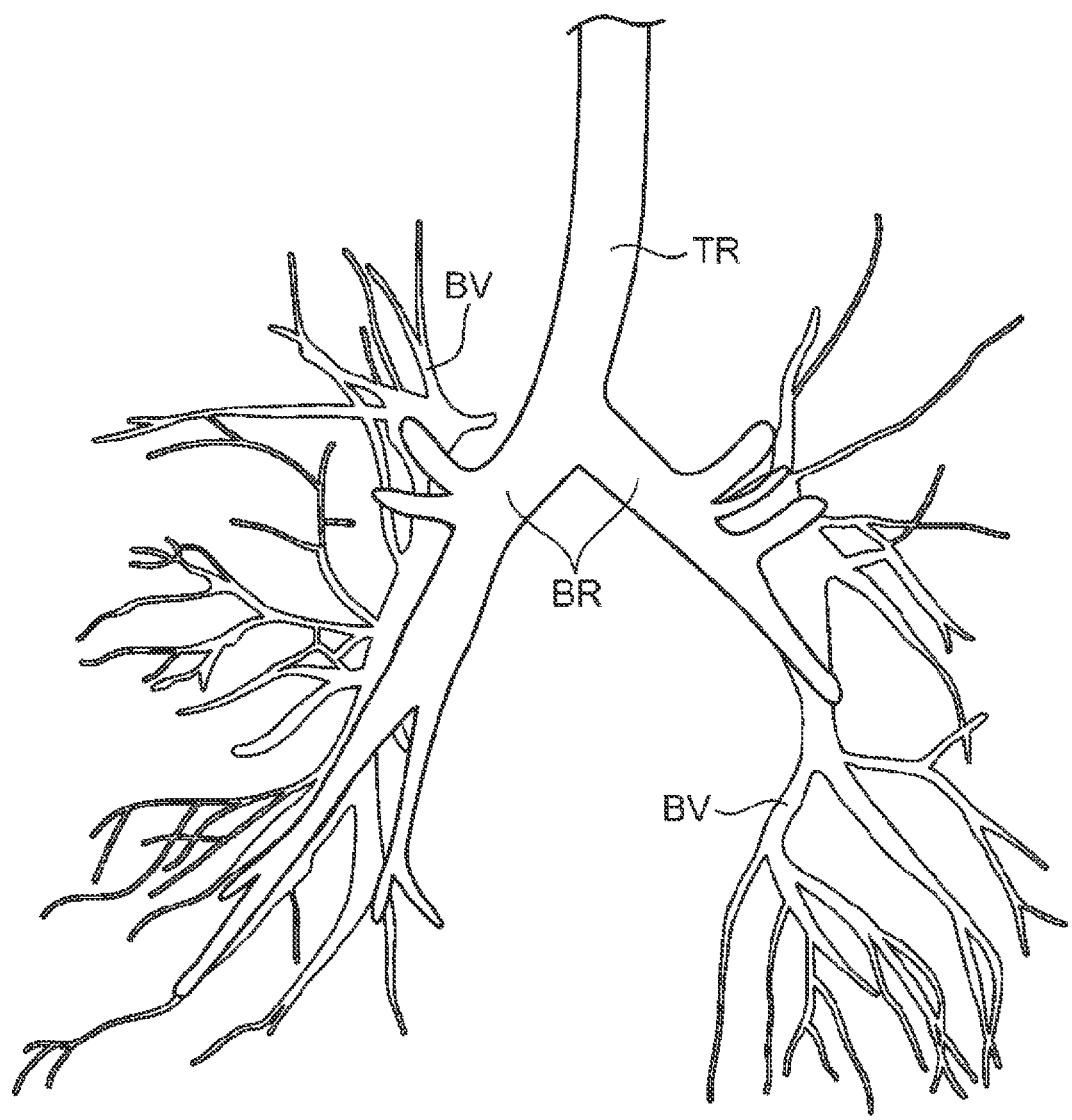
FIG. 17 is a diagram illustrating pulmonary blood vessels, a trachea, and bronchi.

FIGS. 15 and 16 are diagrams schematically illustrating an area in a chest X-ray image where the lungs are present. FIG. 17 is a diagram schematically illustrating pulmonary blood vessels BV, a trachea TR, and bronchi BR.

A lung area will be described with reference to FIG. 15. In FIG. 15, areas RL0 and LL0 in the chest X-ray image Ixp indicate an image of the lungs obtained as a result of threshold processing of pixel shading values. A skilled interpreter of chest X-ray images will interpret a lung area, which is an area indicating an image of the actual lungs, to be an area including the areas RL0 and LL0 and areas defined by lines including boundary lines RLB1, RLB2, LLB1, and LLB2 in FIG. 15. It is therefore important in diagnosis of lung cancer and pneumonia to determine an area including the areas RL0 and LL0 and the areas defined by the lines including the boundary lines RLB1, LLB1, RLB2, and LLB2 as a lung area. In step S200 illustrated in FIG. 3 according to the present embodiment, the lung area setting section 102 may extract the area RL0 and/or the area LL0 using, for example, the technique described in International Publication No. 2009/090894.

Another example of the setting of a lung area in the present disclosure will be described with reference to FIG. 16. In FIG. 16, the area VT indicates an image of the vertebrae (the thoracic vertebrae and the lumbar vertebrae). The lung area illustrated in FIG. 15 other than the area RL0, which indicates the right lung, and the area LL0, which indicates the left lung, is an area included in the area indicating an image of the lungs in FIG. 16 and includes areas RL1, RL2, LL1, and LL2 determined using the detected linear structures. It is important in lung diagnosis to focus upon how the pulmonary blood vessels run through the lungs. As illustrated in FIG. 17, when normal, the pulmonary blood vessels gradually become thinner from hila to pleura, that is, from the center of the lungs to the periphery, while branching out. With current chest X-ray imaging techniques, it is difficult to visually recognize blood vessels near the pleura. An abnormality, that is, a change in the thickness of blood vessels from a normal state due to a disease, can be detected using a difference between the thickness and/or density of blood vessels in a chest X-ray image to be interpreted and the thickness and/or density of blood vessels in a normal state. The density of blood vessels is, for example, a ratio of the area of blood vessels in a local area in an image to the area of the local area. With respect to the thickness of blood vessels, for example, areas occupied by blood vessels are detected from a local area as binary images and labeled as one or more connected areas, and a direction in which lines run in each of the connected areas is identified as a main axis direction in binary image processing. Length in a direction perpendicular to the running direction is obtained as line width, and an average of line widths in all the connected areas is then obtained. When the binary images of the areas occupied by the blood vessels are generated, binarization may be performed after performing line pattern emphasis disclosed in "Development of New Filter Bank for Detection of Nodular Patterns and Line Patterns in Medical Images", The transactions of the Institute of Electronics, Information and Communication Engineers, Vol. J87-D-11, No. 1, pp. 175-185.

FIG. 16 will be referred to again. As illustrated in FIG. 15, the boundary lines RLB1 and LLB1 and the like indicating the area of the lungs are present in the area VT illustrated in FIG. 16 in practice. In this area, however, it is difficult to recognize an image of blood vessels because of an image pattern of the vertebrae.

In the chest X-ray image Ixp, one of the lungs and other organs, such as the diaphragm and the liver, overlap in the area RL1 (an example of a second lung area and an example of a third lung area). Because the X-ray absorbance of the diaphragm and the liver is substantially uniform, however, a strong contrast tends to appear in the lung area (the area RL in the chest X-ray image Ixp illustrated in FIG. 16), which slightly overlaps the diaphragm and the liver from the back in the human body, in the chest X-ray image Ixp between a vascular area and a peripheral area (i.e., the lung parenchyma). In the area RL1, therefore, information regarding the vascular area can be used for image diagnosis.

Similarly, in the chest X-ray image Ixp, one of the lungs and another organ, such as the heart (especially the right atrium), overlap in the area RL2 (an example of a first lung area and an example of the third lung area), and the other of the lungs and another organ, such as the heart (especially the left ventricle), overlap in the area LL1 (an example of the first lung area and an example of the third lung area). Because the X-ray absorbance of the heart is substantially uniform, a strong contrast tends to appear in the lung area (the areas RL2 and LL1 in the chest X-ray image Ixp illustrated in FIG. 16), which slightly overlaps the heart from the back in the human body, in the chest X-ray image Ixp between a vascular area and a peripheral area (i.e., the lung parenchyma). In the areas RL2 and LL1, therefore, information regarding the vascular area can be used for image diagnosis.

In the chest X-ray image Ixp, one of the lungs and other organs, which may be abdominal organs such as the diaphragm and the stomach, overlap in the area LL2 (an example of a fourth lung area). The pulmonary blood vessels might be hard to recognize when there is air or gas inside the stomach, but information regarding a vascular area can be used for image diagnosis, too, in the lung area (the area LL2 in the chest X-ray image Ixp illustrated in FIG. 16), which slightly overlaps the diaphragm and the stomach from the back in the human body. In the present disclosure, therefore, an abnormality is detected while focusing upon patterns of how the pulmonary blood vessels run especially in the areas RL1, RL2, LL1, and LL2.

FIG. 3 will be referred to again. In step S300, the local area setting section 103 divides the lung area set by the lung area setting section 102, that is, the areas RL1, RL2, LL1, and LL2 illustrated in FIG. 16, into local areas.

Figure 18:
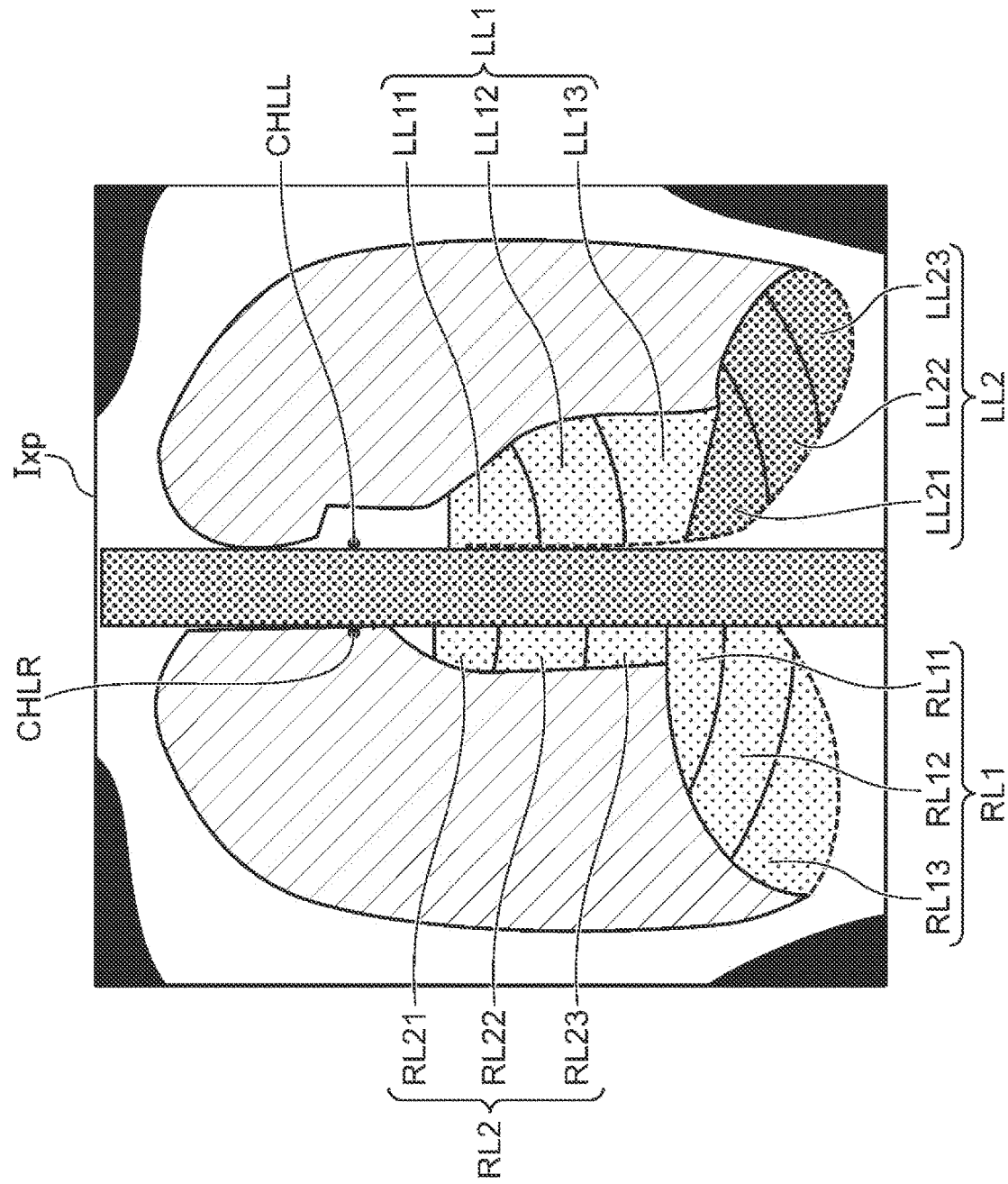
FIG. 18 is a diagram illustrating an example of set local areas.
Figure 19:
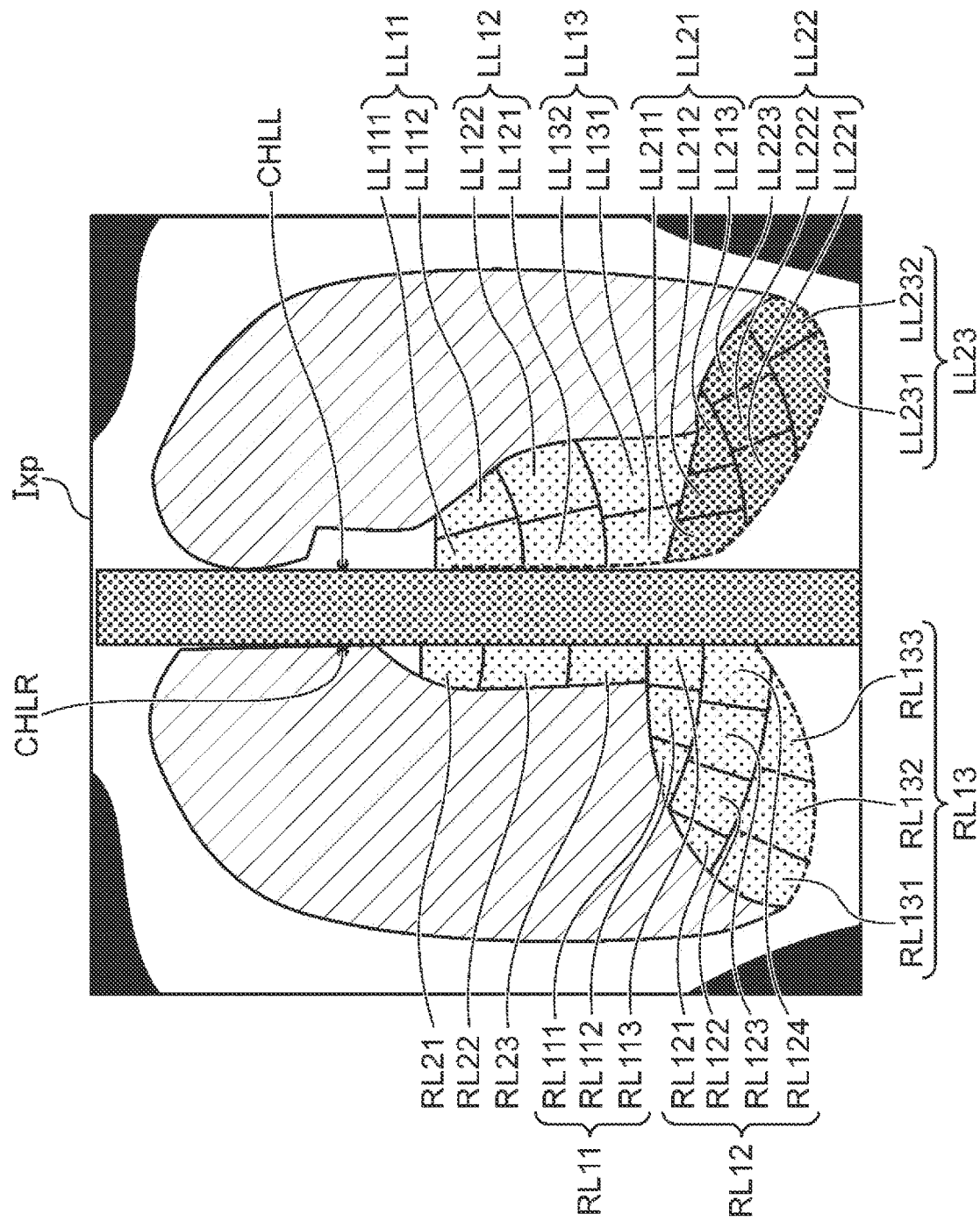
FIG. 19 is a diagram illustrating another example of the set local areas.
Figure 20:
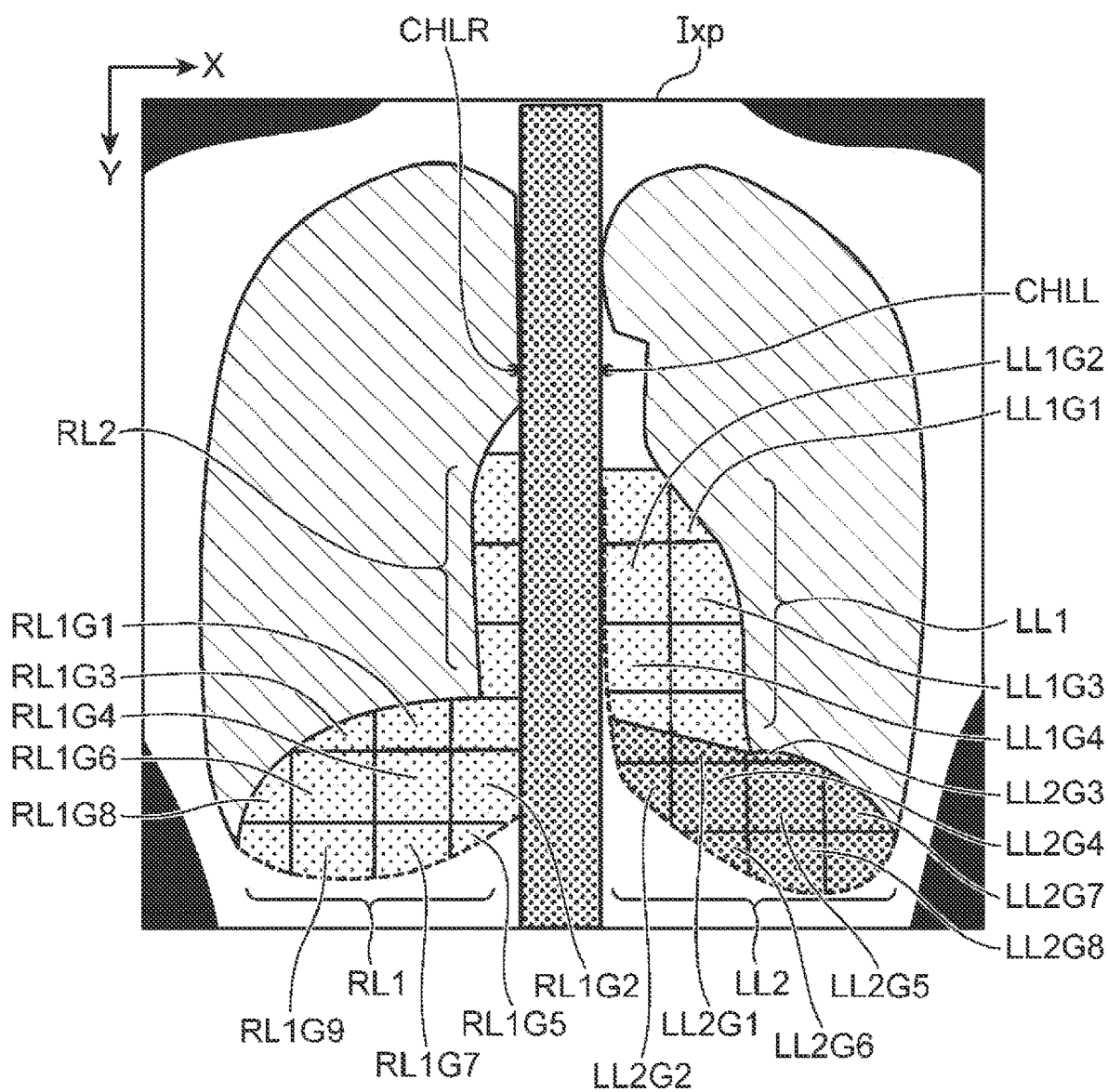
FIG. 20 is a diagram illustrating another example of the set local areas.
Figure 21:
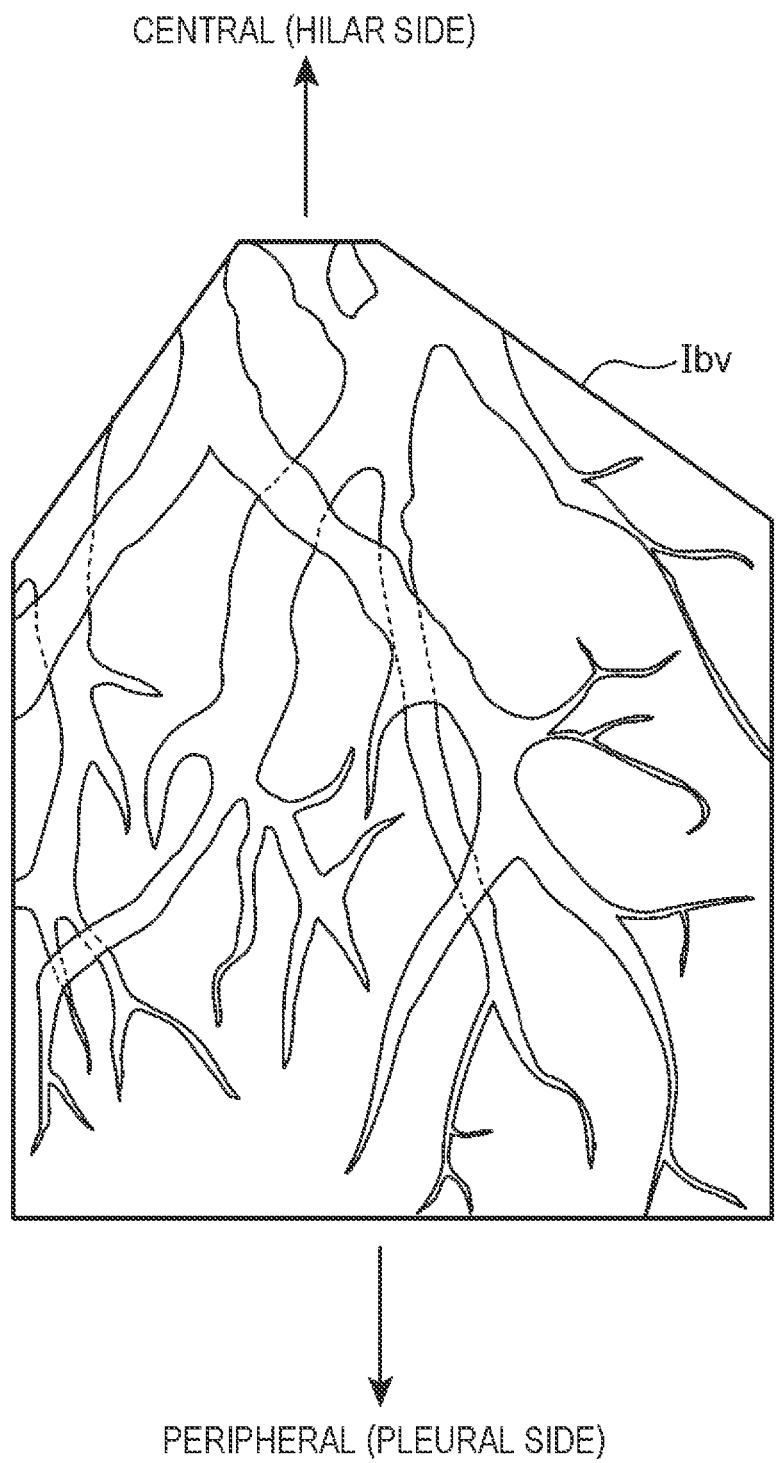
FIG. 21 is a diagram illustrating changes in the thickness and density of the pulmonary blood vessels.
Figure 22:
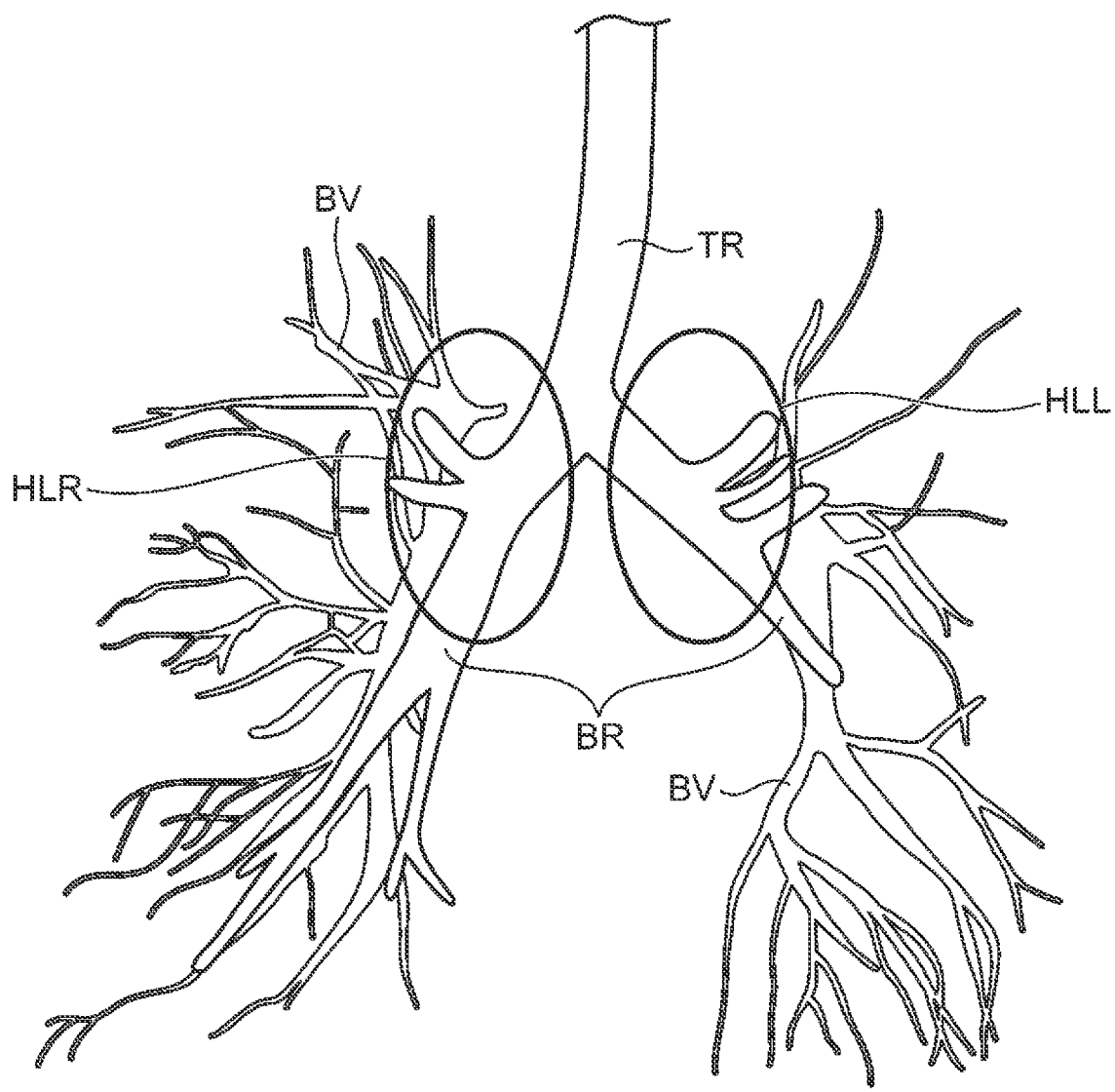
FIG. 22 is a diagram illustrating the pulmonary blood vessels, the trachea, and the bronchi in a human body.

FIGS. 18 to 20 are diagrams schematically illustrating the local areas. FIG. 21 is a diagram schematically illustrating changes in the thickness and density of pulmonary blood vessels. FIG. 21 schematically illustrate a state at a time when pulmonary blood vessels having a depth in an X-ray radiation direction in a body in a part of the lung areas in a chest X-ray image are projected onto a two-dimensional X-ray image. FIG. 22 is a diagram illustrating the pulmonary blood vessels, the trachea, and the bronchi in the human body. In FIG. 22, ellipses indicate positions of the hila.

In FIG. 18, two-dimensional distances, from a right hilum CHLR (described later) in the chest X-ray image Ixp, of lines indicating boundaries between adjacent local areas in the area RL1 illustrated in FIG. 16 are substantially the same. Two-dimensional distances, from the right hilum CHLR in the chest X-ray image Ixp, of lines indicating boundaries between adjacent local areas in the area RL2 are substantially the same. Two-dimensional distances, from a left hilum CHLL (described later) in the chest X-ray image Ixp, of lines indicating boundaries between adjacent local areas in the area LL1 are substantially the same. Two-dimensional distances, from the left hilum CHLL in the chest X-ray image Ixp, of lines indicating boundaries between adjacent local areas in the area LL2 are substantially the same.

Left and right hila HLL and HLR illustrated in FIG. 22, which illustrates the pulmonary blood vessels, the trachea, and the bronchi in the human body, are areas where the bronchi BR, pulmonary arteries, and pulmonary veins enter or go out of the left and right lungs. Because the X-ray absorbance of the pulmonary arteries is high in the chest X-ray image Ixp, an area of the pulmonary arteries can be easily detected in the chest X-ray image Ixp through image processing. In the present disclosure, the local area setting section 103 detects intersections between areas of the pulmonary arteries of the left and right lungs detected through the image processing and the boundary lines of the area VT as the positions of the left hilum CHLL and the right hilum CHLR, respectively. Because the X-ray absorbance of the trachea and the bronchi in a central shadow (not illustrated) is lower than that of the surrounding shadow in a chest X-ray image, the local area setting section 103 can easily detect the trachea and the bronchi. The local area setting section 103, therefore, may detect intersections between the bronchi of the left and right lungs detected through the image processing and the boundary lines of the area VT as the positions of the left hilum CHLL and the right hilum CHLR, respectively, in FIGS. 18 to 20. The central shadow refers to an area sandwiched by the left and right lungs in the chest X-ray image and in FIGS. 18 to 20, refers to an area including the area VT, the area indicating the heart (the areas RL2 and LL1), and the area (not illustrated) indicating the descending aorta.

In FIG. 18, the area RL1 includes local areas RL11, RL12, and RL13. A boundary line between the local areas RL11 and RL12 is a set of dots whose two-dimensional distances from the right hilum CHLR are substantially the same (i.e., an arc around the right hilum CHLR). A boundary line between the local areas RL12 and RL13 is a set of dots whose two-dimensional distances from the right hilum CHLR are substantially the same. In FIG. 18, the area RL2 includes local areas RL21, RL22, and RL23. A boundary line between the local areas RL21 and RL22 is a set of dots whose two-dimensional distances from the right hilum CHLR are substantially the same. A boundary line between the local areas RL22 and RL23 is a set of dots whose two-dimensional distances from the right hilum CHLR are substantially the same.

In FIG. 18, the area LL1 includes local areas LL11, LL12, and LL13. A boundary line between the local areas LL11 and LL12 is a set of dots whose two-dimensional distances from the left hilum CHLL are substantially the same (i.e., an arc around the left hilum CHLL). A boundary line between the local areas LL12 and LL13 is a set of dots whose two-dimensional distances from the left hilum CHLL are substantially the same. In FIG. 18, the area LL2 includes local areas LL21, LL22, and LL23. A boundary line between the local areas LL21 and LL22 is a set of dots whose two-dimensional distances from the left hilum CHLL are substantially the same. A boundary line between the local areas LL22 and LL23 is a set of dots whose two-dimensional distances from the left hilum CHLL are substantially the same.

In the example illustrated in FIG. 18, the areas RL1, RL2, and LL1 are an example of the third lung area, and the local areas RL11, RL12, RL13, RL21, RL22, RL23, LL11, LL12, and LL13 are an example of local areas 1 to n. That is, n=9 in the example illustrated in FIG. 18.

As illustrated in FIG. 19, the local area setting section 103 may divide the local areas along straight lines passing through the hila. In FIG. 19, the local area RL11 is divided into three local areas RL111, RL112, and RL113 along a first set of straight lines passing through the right hilum CHLR. The local area RL12 is divided into four local areas RL121, RL122, RL123, and RL124 along a second set of straight lines passing through the right hilum CHLR. The local area RL13 is divided into three local areas RL131, RL132, and RL133 along a third set of straight lines passing through the right hilum CHLR.

The local area LL11 is divided into two local areas LL111 and LL112 along a straight line passing through the left hilum CHLL. The local area LL12 is divided into two local areas LL121 and LL122 along a straight line passing through the left hilum CHLL. The local area LL13 is divided into two local areas LL121 and LL122 along a straight line passing through the left hilum CHLL. The local area LL21 is divided into three local areas LL211, LL212, and LL213 along a fourth set of straight lines passing through the left hilum CHLL. The local area LL22 is divided into three local areas LL221, LL222, and LL223 along a fifth set of straight lines passing through the left hilum CHLL. The local area LL23 is divided into two local areas LL231 and LL232 along a straight line passing through the left hilum CHLL.

As illustrated in FIG. 20, the local area setting section 103 may divide the areas RL1, RL2, LL1, and LL2 into a grid using one or more straight lines parallel to an X-axis set for the chest X-ray image Ixp and/or one or more straight lines parallel to a Y-axis set for the chest X-ray image Ixp, instead. In FIG. 20, the local area setting section 103 may group the local areas on the basis of two-dimensional distances between the hilum CHLR or CHLL and centers of gravity of the local areas. In this case, a reference index (described later with reference to FIG. 30) obtained in advance on the basis of a normal model (i.e., a standard image of the lungs created on the basis of a large number of normal cases) is obtained for each of groups and saved in the normal model storage unit 105 in advance.

In FIG. 20, for example, the local area setting section 103 may include local areas LL1G1 and LL1G2 in a first group and local areas LL1G3 and LL1G4 in a second group. The local area setting section 103 may include local areas RL1G1 and RL1G2 in a third group, local areas RL1G3, RL1G4, RL1G5 in a fourth group, local areas RL1G6 and RL1G7 in a fifth group, and local areas RL1G8 and RL1G9 in a sixth group. The local area setting section 103 may include local areas LL2G1 and LL2G2 in a seventh group, local areas LL2G3 and LL2G4 in an eighth group, local areas LL2G5 and LL2G6 in a ninth group, and local areas LL2G7 and LL2G8 in a tenth group. In the example illustrated in FIG. 20, the local area setting section 103 generates the first to tenth groups, and these ten groups are an example of groups 1 to m. That is, m=10 in the example illustrated in FIG. 20.

When local areas are grouped together and a reference index in a normal model is obtained for each of groups of local areas, the number of local images for obtaining the reference index increases compared to when a reference index in a normal model is obtained for each of local areas, provided that the number of chest X-ray images at a time when the reference index is obtained using a normal model remains the same. As a result, statistical reliability of an obtained reference index in a normal model increases.

Advantageous effects produced by the division into local areas will be described. As illustrated in FIG. 21, the diameter of pulmonary blood vessels decreases from the hila, which is the center of the lungs, to the pleura, which is the periphery. The pulmonary blood vessels also branch out, and the number of pulmonary blood vessels increases. When the diameter reaches a certain value, it becomes difficult to draw an area of the pulmonary blood vessels in a chest X-ray image Ibv. When areas whose distances from the hila are substantially the same are determined as the same local areas at a time of division, therefore, the diameter (thickness) of blood vessels and the density of the blood vessels (e.g., a ratio of the area of the blood vessels in a local area in an image to the area of the local area) become substantially uniform within the local areas. As a result, a normal state in the local areas whose distances from the hila are substantially the same can be defined well, which is advantageous because such a condition is suitable for detection of an abnormality based on a reference index in a normal model.

In addition, when the areas are finely divided into local areas as illustrated in FIGS. 19 and 20, the resolution of an area where an abnormality is detected improves because, as described later, an abnormality is detected in each of the local areas in the present embodiment.

FIG. 3 will be referred to again. In step S400, the abnormality determination section 104 selects one (local area i) of the local areas set by the local area setting section 103. In step S500, the abnormality determination section 104 extracts an index (an example of a vascular index) indicating the thickness and density of the pulmonary blood vessels. The abnormality determination section 104 may extract an index indicating one of the thickness or density of the pulmonary blood vessels, instead. It is only required that the abnormality determination section 104 extract at least one of the thickness or density of the pulmonary blood vessels. Various techniques may be used for the extraction of the index.

After an area of blood vessels is extracted, for example, a feature value indicating at least one of the thickness or density of the blood vessels may be separately extracted. A method for extracting linear structures using a maximum eigenvalue calculated from elements of a Hessian matrix, which is described in "Development of New Filter Bank for Detection of Nodular Patterns and Line Patterns in Medical Images", may be used to extract blood vessels. In addition, when bandwidth filter banks for generating elements of a Hessian matrix are constructed, linear structures can be extracted at each resolution level, that is, vascular areas whose sizes are different from one another can be extracted. After linear structures at each resolution level are extracted using the bandwidth filter banks, density at each resolution level can be calculated on the basis of a ratio of pixel values in a foreground (linear structures) to pixel values in a background. For example, an index indicating at least one of the thickness or density of the pulmonary blood vessels can be extracted using the above method. When the number of filter banks is FB and a one-dimensional (scholar) value is used as density, a feature value in FB dimensions can be extracted from each local area.

Low-dimensional feature values can be extracted not by explicitly extracting an index relating to the pulmonary blood vessels, that is, a feature value, but by dimensionally reducing an image of a local area while assuming that the image includes an index indicating at least one of the thickness or density of the pulmonary blood vessels. This method will be described later with respect to step S700.

FIG. 3 will be referred to again. In step S600, the abnormality determination section 104 extracts, from the normal model storage unit 105, a reference index of a local area in a normal model corresponding to the local area i included in the image of the lungs to be interpreted. Various methods may be used for associating local areas set by the local area setting section 103 and local areas in a normal model stored in the normal model storage unit 105 with each other.

When a reference index is stored in the normal model storage unit 105 for a local area in advance, for example, an index indicating a position of the local area in the lung area illustrated in FIG. 16 may be attached to the local area. As the index, for example, a position of center coordinates of the local area relative to an external rectangle of the area RL0, RL1, or RL2 in FIG. 16 may be used.

Figure 23:
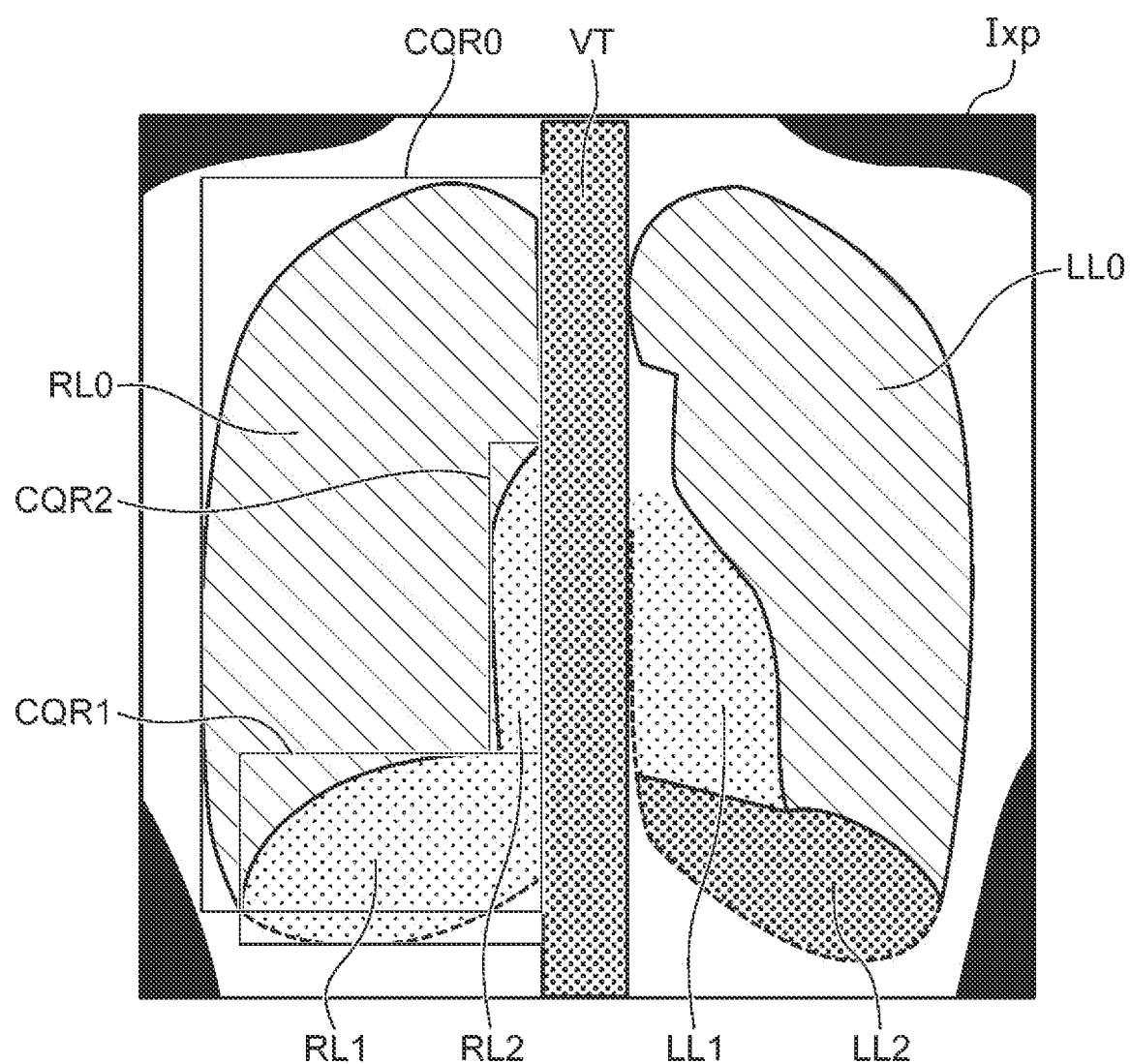
FIG. 23 is a diagram illustrating external rectangles of the areas illustrated in FIG. 16.

FIG. 23 is a diagram illustrating external rectangles CQR0, CQR1, and CQR2 of the areas RL0, RL1, and RL2, respectively, illustrated in FIG. 16. Normalized center coordinates (x, y) of a local area at a time when a start point and an end point of an X-coordinate of a reference external rectangle are 0 and 1, respectively, and a start point and an end point of a Y-coordinate of the reference external rectangle are 0 and 1, respectively, can be defined.

Figure 24:
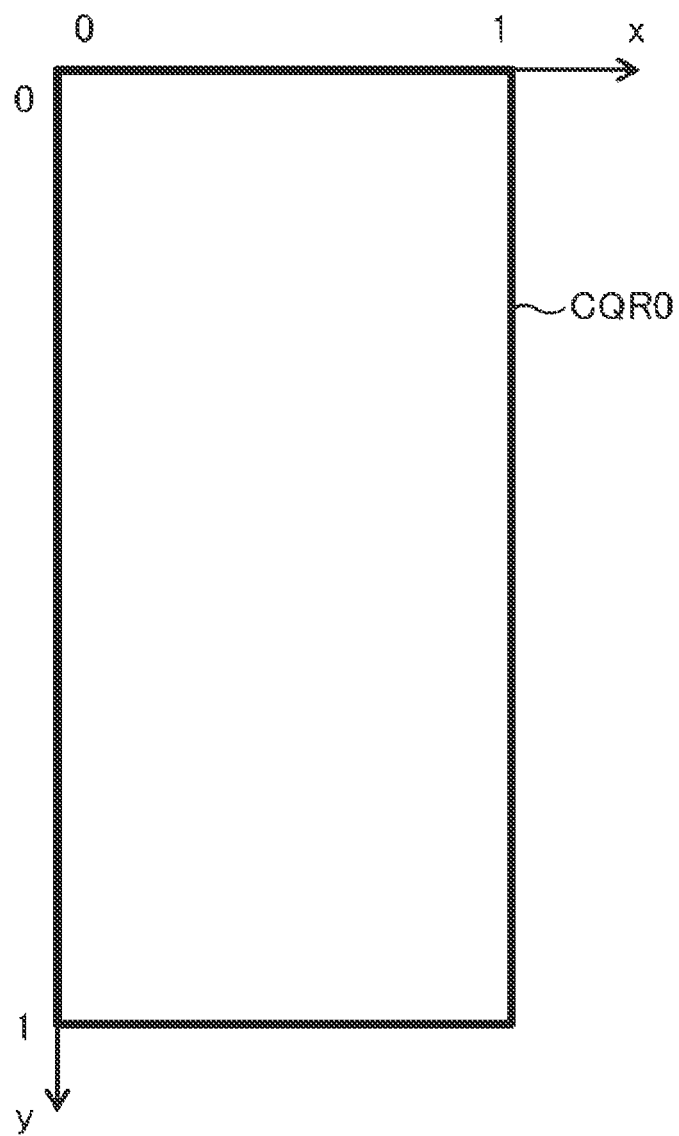
FIG. 24 is a diagram illustrating a normalized coordinate system based on one of the external rectangles of the areas.
Figure 25:
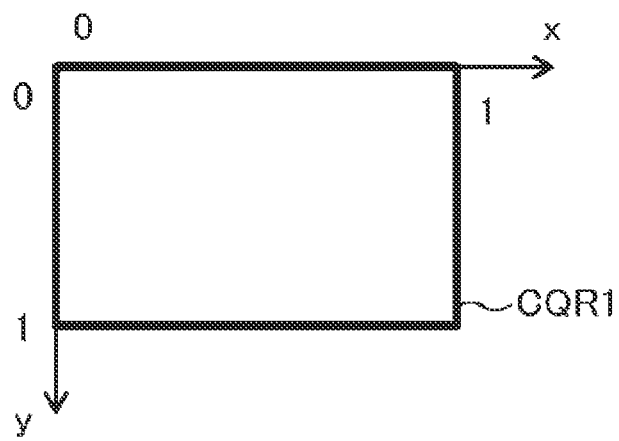
FIG. 25 is a diagram illustrating a normalized coordinate system based on another of the external rectangles of the areas.
Figure 26:
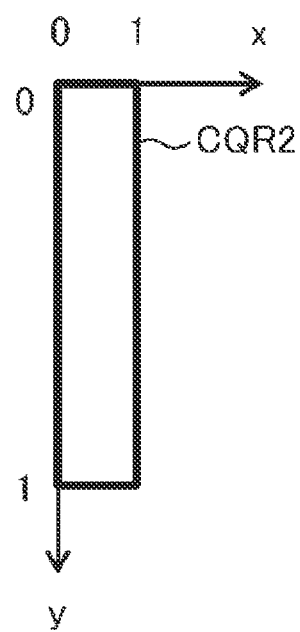
FIG. 26 is a diagram illustrating a normalized coordinate system based on the other of the external rectangles of the areas.

FIGS. 24, 25, and 26 are diagrams illustrating normalized coordinate systems based on the external rectangles CQR0, CQR1, and CQR2 of the areas RL0, RL1, and RL2, respectively. As normalized center coordinates of a local area, a position of a center of gravity of a local area image (a binary image where the inside of the local area is 1 and the outside of the local area is 0) in a coordinate system of an area including the local area can be used.

Figure 27:
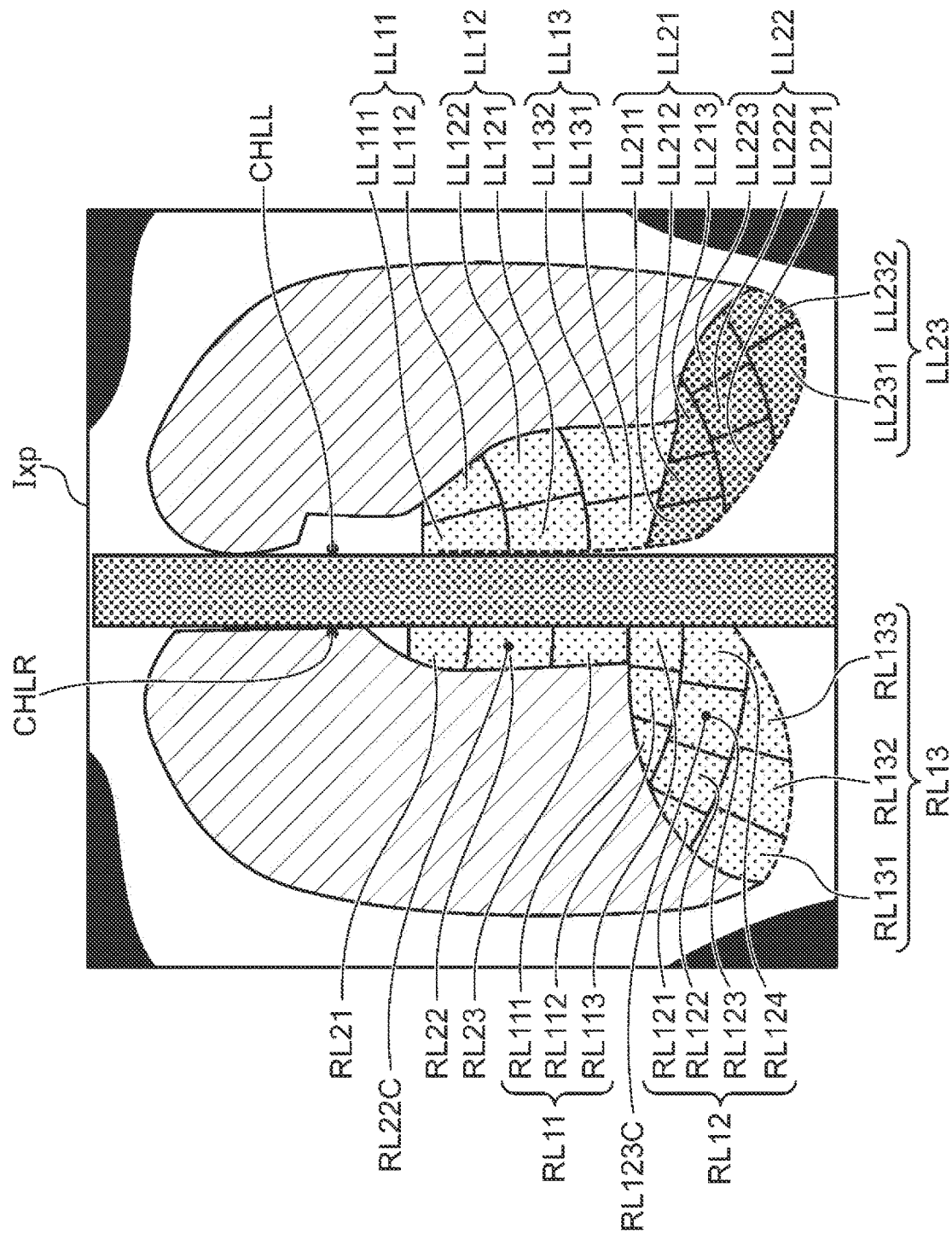
FIG. 27 is a diagram illustrating an example of positions of centers of gravity of local areas in a chest X-ray image illustrated in FIG. 19.

FIG. 27 is a diagram illustrating an example of positions of centers of gravity of the local areas in the chest X-ray image illustrated in FIG. 19. In FIG. 27, for example, coordinates of a position RL123C of a center of gravity of the local area RL123 is represented by the normalized coordinate system of the area RL1 (the normalized coordinate system based on the external rectangle CQR1) illustrated in FIG. 25. Similarly, in FIG. 27, coordinates of a position RL22C of a center of gravity of the local area RL22 is represented by the normalized coordinate system of the area RL2 (the normalized coordinate system based on the external rectangle CQR2) illustrated in FIG. 26.

Here, $0 \le x \le 1$ and $0 \le y \le 1$. Association between local areas from different normal cases when a normal model is created or association between a local area in which an abnormality is to be detected (i.e., a local area to be interpreted by a doctor) during detection of an abnormality and a local area in a normal model can be achieved by searching for a target with which a distance to the normalized center coordinates (x, y) becomes the smallest. For example, the association between a local area in which an abnormality is to be detected during detection of an abnormality and a local area in a normal model will be described with reference to FIGS. 28 and 29.

Figure 28:
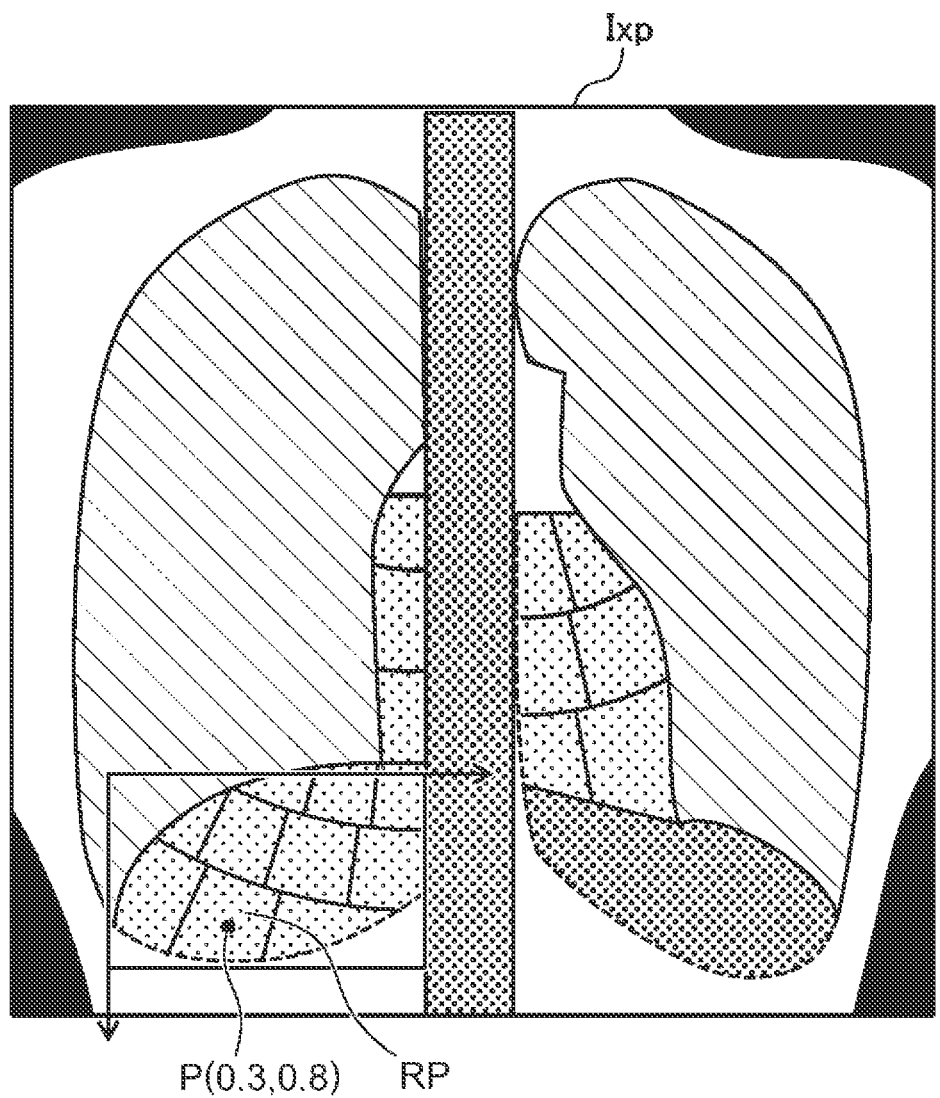
FIG. 28 is a diagram illustrating a chest X-ray image in which an abnormality is to be detected.
Figure 29:
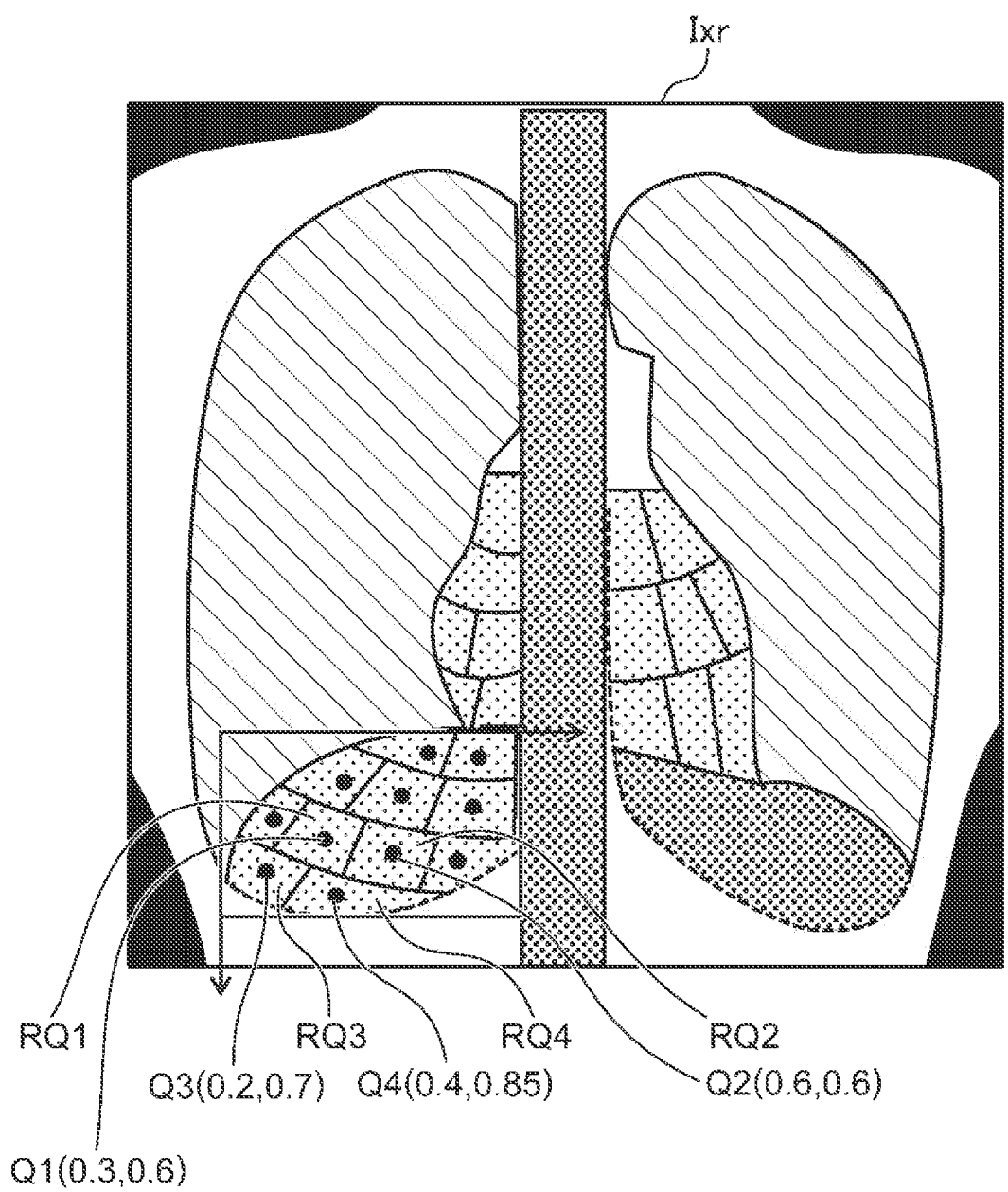
FIG. 29 is a diagram illustrating a chest X-ray image in a normal model.

FIG. 28 is a diagram illustrating the chest X-ray image Ixp in which an abnormality is to be detected (i.e., the chest X-ray image Ixp to be interpreted by a doctor). FIG. 29 is a diagram illustrating a chest X-ray image Ixr of a normal model. A case will be assumed where a local area RP whose normalized center coordinates are a point P(0.3, 0.8) and a local area in the normal model for which indices are to be compared are identified in the chest X-ray image Ixp (FIG. 28) to be interpreted, in which an abnormality is to be detected. In this case, among points Q1 to Q4, a point whose normalized center coordinates whose distance from those of the point P are the smallest is the point Q4(0.4, 0.85) in the chest X-ray image Ixr in the normal model (FIG. 29). An index of the local area RP and a reference index of a local area RQ4, therefore, are compared with each other.

Association between local areas from different normal cases when a normal model is created is performed in the same manner. At this time, one of the normal cases for creating a normal model is selected as a reference case for determining a method for dividing local areas, and local areas in the other normal cases are all associated with local areas in the reference case. A normal case whose number of local areas set is the largest may be selected as the reference case in order to emphasize position resolution.

When setting local areas, the local area setting section 103 may set local areas while using the same number of local areas divided according to a distance from the hila and the same number of local areas divided in a direction perpendicular to a distance direction from the hila in different chest X-ray images, and attach the same index to corresponding local areas. In this case, the abnormality determination section 104 can extract, from the normal model storage unit 105, a reference index of a local area in a normal model corresponding to a local area included in a chest X-ray image in which an abnormality is to be detected by comparing an index added to the normal model and an index added to the chest X-ray image in which an abnormality is to be detected.

When a normal model is created, the size and a position of an image of the lungs are essentially normalized by introducing a normalized coordinate system in the above description. The abnormality determination section 104, therefore, may determine that, among local areas included in a normal model, one having the largest area overlapping the local area i included in the image of the lungs to be interpreted is a local area corresponding to the local area i after normalizing the size and position of the image of the lungs to be interpreted and superimposing the normal model stored in the normal model storage unit 105 (i.e., the standard image of the lungs created on the basis of a large number of normal cases) upon the image of the lungs to be interpreted.

In step S700, the abnormality determination section 104 (an example of a determiner) compares the index extracted in step S500 with the reference index extracted in step S600 and determines, on the basis of a result of the comparison, whether the local area i included in the image of the lungs to be interpreted is in an abnormal state. The abnormality determination section 104 saves an abnormality determination result, that is, a local area determined to be in an abnormal state and details of an abnormality, in the memory 121.

Although a local area whose normalized center coordinates are the closest to those in a normal model is selected as a local area corresponding to a local area in a chest X-ray image in which an abnormality is to be detected and a reference index of the selected local area is used for an abnormality determination in the above description, an index used is not limited to this. For example, normalized center coordinates of local areas in a normal model that are close to normalized center coordinates of a local area in a chest X-ray image in which an abnormality is to be detected may be selected, and a single reference index may be newly obtained from reference indices of the selected local areas in accordance with the closeness to the normalized center coordinates of the local area in the chest X-ray image.

When local areas in a normal model are selected, local areas having normalized center coordinates whose distances from normalized center coordinates of a local area in a chest X-ray image in which an abnormality is to be detected are smaller than a certain value or a certain number of local areas having normalized center coordinates whose distances from the normalized center coordinates of the local area in the chest X-ray image are the smallest may be selected. It is assumed in FIGS. 28 and 29, for example, that three local areas having normalized center coordinates whose distances from the normalized center coordinates of the local area in the chest X-ray image in which an abnormality is to be detected are the smallest are selected. In this case, the normalized center coordinates Q4, Q3, and Q1 are selected as normalized center coordinates of the chest X-ray image Ixr (FIG. 29) in the normal model corresponding to the normalized center coordinates P of the chest X-ray image Ixr (FIG. 28) in which an abnormality is to be detected. That is, among local areas RQ1, RQ2, RQ3, and RQ4, the local areas RQ4, RQ3, and RQ1 having the normalized center coordinates Q4, Q3, and Q1, respectively, are selected. A new reference index can then be calculated by combining together reference indices of the local areas RQ4, RQ3, and RQ1 while weighting the reference indices with reciprocals of the distances.

With respect to a reference index, a large number of chest X-ray images in normal cases are prepared in advance, and a probability density function of indices (vascular indices indicating the thickness and density of blood vessels in the present embodiment) is calculated from the chest X-ray images for each of local areas using the method in step S500. The probability density functions of indices corresponding to the local areas are saved in the normal model storage unit 105 in advance as reference indices.

Figure 30:
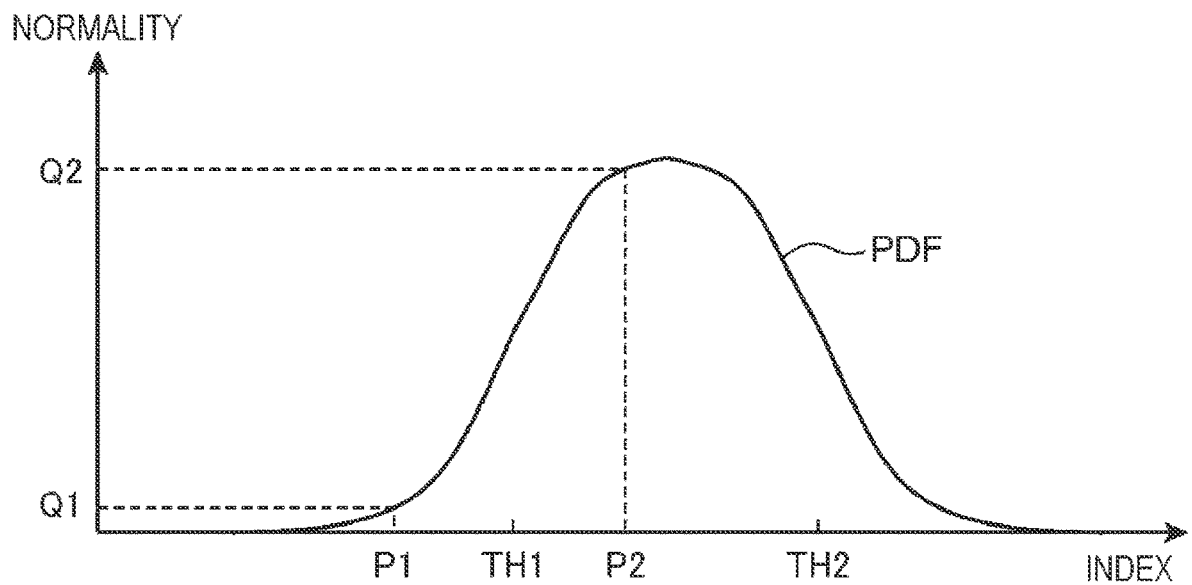
FIG. 30 is a diagram schematically illustrating a probability density function, which is an example of a reference index.

FIG. 30 is a diagram schematically illustrating an example of a probability density function PDF of an index. The probability density function PDF of an index illustrated in FIG. 30 is obtained by calculating indices from chest X-ray images in a large number of normal cases using a certain algorithm and plotting the frequency of the calculated indices. In the present embodiment, the probability density function PDF of an index illustrated in FIG. 30 is saved in the normal model storage unit 105 as a reference index. The probability density function PDF of an index is obtained in advance for each of local areas. The abnormality determination section 104 determines whether each of the local areas is in an abnormality state using, for example, the probability density function PDF illustrated in FIG. 30. FIG. 30 illustrates a probability density function of a one-dimensional index, but in the case of a multidimensional index, that is, an FB-dimensional feature value, for example, "index" represented by a horizontal axis in FIG. 30 is replaced by "vector" and the probability density function PDF exhibits a normal distribution in an FB-dimensional space. The abnormality determination section 104 determines the normality of an index extracted from a local area with a probability in the probability density function PDF of an index corresponding to the index. In FIG. 30, for example, the normality of extracted indices P1 and P2 is Q1 and Q2, respectively. The abnormality determination section 104, therefore, determines that the index P2 is probably normal and that the index P1 is probably abnormal.

When the probability density function is one-dimensional as illustrated in FIG. 30, it can be determined, on the basis of a comparison between a mode or a mean (the two match in the case of a normal distribution) of the probability density function and an index, whether a reason for an abnormality is an excessive index or an insufficient index. When the probability density function is multidimensional, it can be determined, on the basis of a position of an index in a multidimensional space relative to a position of a mode or a mean of the probability density function, whether a reason for an abnormality is an insufficient index or an excessive index in a certain dimension. With this method, for example, whether wider, normal, or narrower blood vessels are increasing or decreasing can be identified as a reason for an abnormality.

Methods for representing the probability density function PDF include a method in which a parametric model based on a relatively small number of parameters is used and a method in which a nonparametric model for identifying a type of distribution on the basis of individual data without assuming a particular functional type is used. When a low-dimensional index is extracted from a local area, the abnormality determination section 104 determines whether the local area is in an abnormal state using the probability density function. When a parametric model is used, for example, parameters (e.g., an average and a standard deviation of a normal distribution) indicating the probability density function are stored in the normal model storage unit 105 as reference indices.

When a feature value indicating the thickness and density of blood vessels is extracted, details of an abnormality can be set, such as whether the blood vessels are thicker, narrower, or different than in a normal state and whether the blood vessels are sparser, denser, or different than in the normal state. In a local area where an infiltration shadow due to pneumonia or a nodular shadow or a tumor shadow due to lung cancer exists, for example, a vascular pattern is hard to recognize, and blood vessels become sparser than in a normal state. In a local area where honeycombing is observed, for example, a usual vascular pattern is hard to recognize, a pattern of walls of a honeycomb lung is extracted instead of blood vessels, and thicknesses or densities of vascular shadows different from ones in a normal state are obtained. In a local area where pleural thickening has occurred due to a heart failure, for example, a pattern of pleural thickening is extracted instead of blood vessels in an area where a vascular pattern is not observed in a normal state, and thicknesses or densities of vascular shadows different from ones in the normal state are obtained.

When a high-dimensional index is extracted from a local area, on the other hand, a method for determining an abnormality based on dimensionality reduction can be used. This method can be used when, as mentioned in step S500, a low-dimensional feature value is extracted by dimensionally reducing an image of a local area while assuming that the image includes an index indicating at least one of the thickness or density of pulmonary blood vessels.

Figure 31:
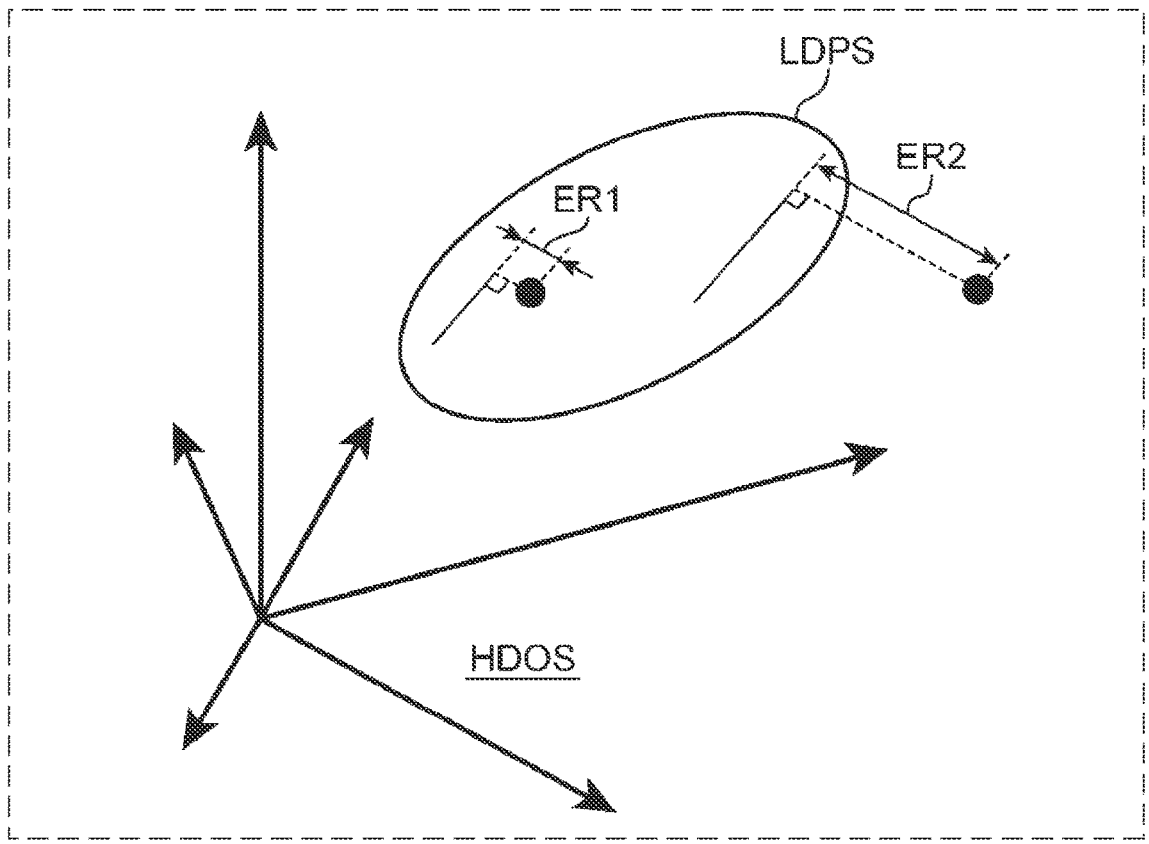
FIG. 31 is a diagram illustrating an abnormality determination method based on dimensionality reduction.

FIG. 31 is a diagram illustrating an abnormality determination method based on a reconstruction error in dimensionality reduction. During machine learning for obtaining a reference index of a normal model, a low-dimensional partial space LDPS, which is obtained as a result of dimensionality reduction, is obtained from a high-dimensional original image HDOS in which a training data set is distributed. When the low-dimensional partial space LDPS is obtained while constructing the training data set with normal data, the low-dimensional partial space LDPS is supposed to be a space reflecting features of the normal data. When an index extracted from a local area is projected onto the low-dimensional partial space LDPS, a reconstruction error ER1 smaller than a certain threshold is obtained if the index is similar to the original training data (i.e., if the index is normal data). If the index is abnormal data, on the other hand, a reconstruction error ER2 larger than or equal to the certain threshold is obtained. On the basis of this characteristic, the abnormality determination section 104 determines whether the local area is in an abnormal state. A reconstruction error can be calculated from a distance between a vector at a time when an index extracted from a local area is projected onto the low-dimensional partial space LDPS (i.e., at a time of dimensionality reduction) and a vector in the high-dimensional original space HDOS. For the dimensionality reduction, a principal component analysis, a stacked autoencoder, a variational autoencoder, or the like can be used.

Figure 32:
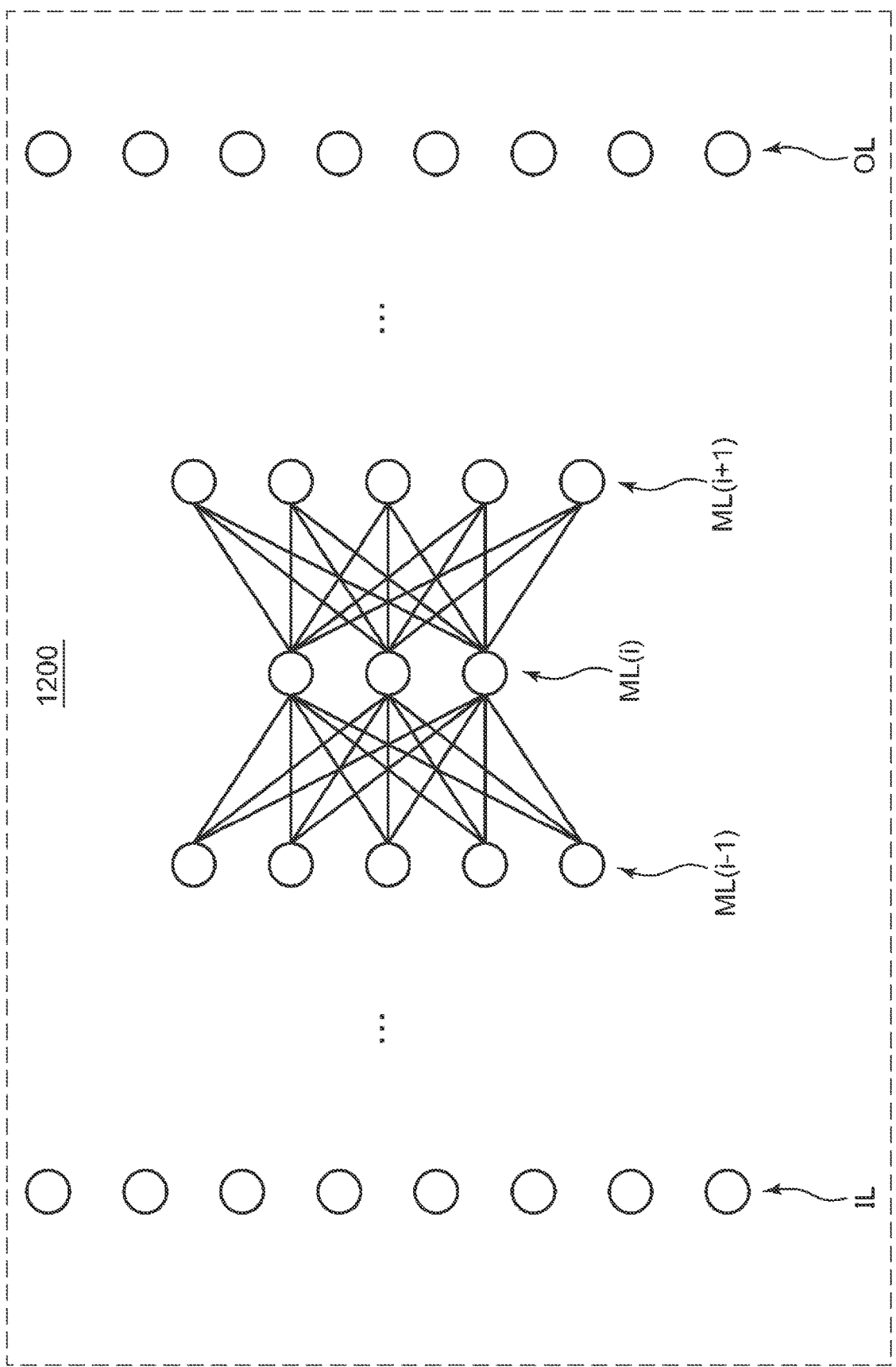
FIG. 32 is a diagram illustrating the network configuration of a stacked autoencoder.

FIG. 32 is a diagram illustrating the network configuration of a stacked autoencoder 1200. As illustrated in FIG. 32, the stacked autoencoder 1200 is an hourglass feedforward network that includes an input layer IL, an output layer OL, and two or more hidden layers ML and in which the number of neurons in each of the hidden layers ML is smaller than that in the input layer IL or the output layer OL. The stacked autoencoder 1200 learns input data as training data in order to obtain an output that reproduces an input. At an end of the learning, the hidden layers ML become able to clearly express features of the training data set. An output of a hidden layer ML(i), therefore, can be used as dimensionality reduction data.

FIG. 33 is a diagram illustrating the network configuration of a variational autoencoder 1300. As illustrated in FIG. 33, the variational autoencoder 1300 is an hourglass network that includes an input layer IL, an output layer OL, and two or more hidden layers and in which, as with the stacked autoencoder 1200 (FIG. 32), the number of neurons in each of the hidden layers is smaller than that in the input layer IL or the output layer OL. Jinwon An and Sungzoon Cho, "Variational Autoencoder based Anomaly Detection Using Reconstruction Probability", Dec. 27, 2015, SNU Data Mining Center, 2015-2, Special Lecture on IE, for example, discloses a variational autoencoder. FIG. 33 corresponds to FIG. 2 or 3 of "Variational Autoencoder based Anomaly Detection Using Reconstruction Probability".

In the variational autoencoder 1300, an encoder ECD receives an image x and outputs parameters of a distribution $q\varphi(z|x)$ of z, which is a latent variable LV for generating the image x. A decoder DCD outputs a distribution $p\theta(x|z)$ of the generated image on the basis of z sampled from the distribution $q\varphi(z|x)$. Learning based on the variational autoencoder 1300 is performed by maximizing a variational lower bound of a logarithmic marginal likelihood $\log p\theta(x)$ of each point x of the data set. In "Variational Autoencoder based Anomaly Detection Using Reconstruction Probability", a training algorithm is described as algorithm 3.

An abnormality determination employing the variational autoencoder 1300 is performed as follows. A target chest X-ray image y is input to the encoder ECD subjected to learning, and a distribution $f(z|y)$ whose latent variable LV is z is obtained. The latent variable z is then obtained by performing sampling from this distribution, and a likelihood $p\theta(y|z)$ of the target chest X-ray image y is obtained using the obtained latent variable z. The abnormality determination section 104 then determines whether a local area is abnormal or normal on the basis of the likelihood $p\theta(y|z)$. In "Variational Autoencoder based Anomaly Detection Using Reconstruction Probability", a determination algorithm is described as algorithm 4.

In the case of the principal component analysis, a matrix to be subjected to dimensionality reduction is stored in the normal model storage unit 105 as a reference index in a normal model. In the case of a stacked autoencoder or a variational autoencoder, a network structure subjected to learning and parameters are stored in the normal model storage unit 105 as a reference index in a normal model.

Because it is difficult for the abnormality determination section 104 to identify a reason for an abnormality from a reconstruction error in the case of the method based on dimensionality reduction, only information indicating a local area determined to be in an abnormal state is saved in the memory 121 as an abnormality determination result.

FIG. 3 will be referred to again. In step S800, the abnormality determination section 104 determines whether all the local areas have been selected. If so (YES in step S800), the process proceeds to step S900. If not (NO in step S800), on the other hand, the process returns to step S400. A next local area is selected, and the above steps are repeated. In step S900, the display control section 122 displays local areas determined in step S700 to be in an abnormal state and details of an abnormality on the display 108.

Figure 34A:
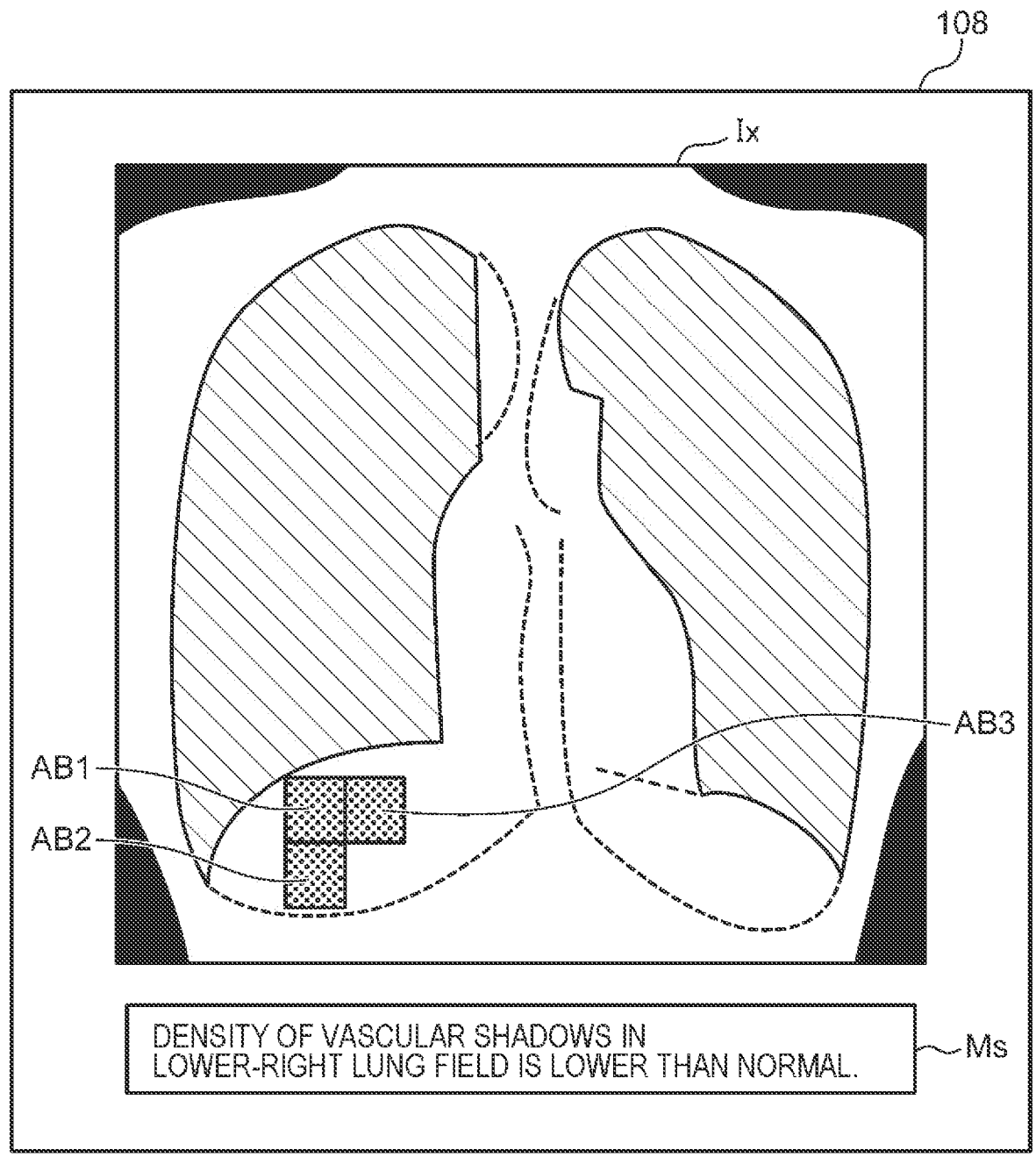
FIG. 34A is a diagram illustrating an example of information displayed on a display according to the first embodiment.

FIG. 34A is a diagram schematically illustrating an example of information displayed on the display 108. As illustrated in FIG. 34A, the display control section 122 displays, on the display 108, a target chest X-ray image Ix, local areas AB1, AB2, and AB3 determined to be in an abnormal state, and a message Ms indicating details of the abnormal state. Names of local areas and the message Ms are defined and saved in the memory 121 in advance. In the example illustrated in FIG. 34A, the local areas AB1, AB2, and AB3 are examples of a local area j.

Figure 34B:
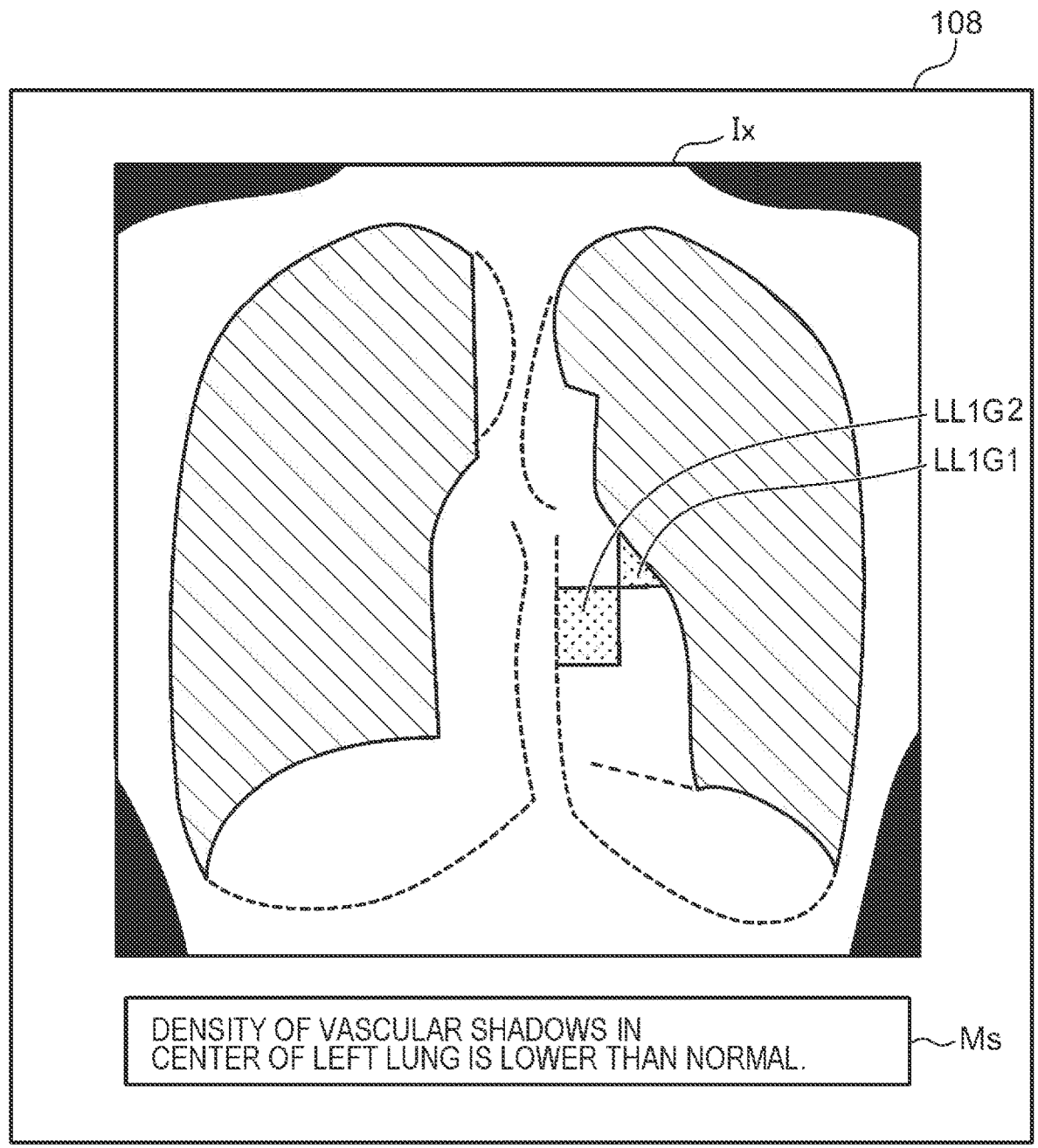
FIG. 34B is a diagram illustrating another example of the information displayed on the display.

FIG. 34B is a diagram schematically illustrating another example of the information displayed on the display 108. In the example illustrated in FIG. 34B, the display control section 122 displays, on the display 108, a target chest X-ray image Ix, the local areas LL1G1 and LL1G2 determined to be in an abnormal state, and a message Ms indicating details of the abnormal state. As described with reference to FIG. 20, the local area setting section 103 includes the local areas LL1G1 and LL1G2 in the first group. That is, in the example illustrated in FIG. 34B, the first group including the local areas LL1G1 and LL1G2 is an example of a group h.

Figure 35:
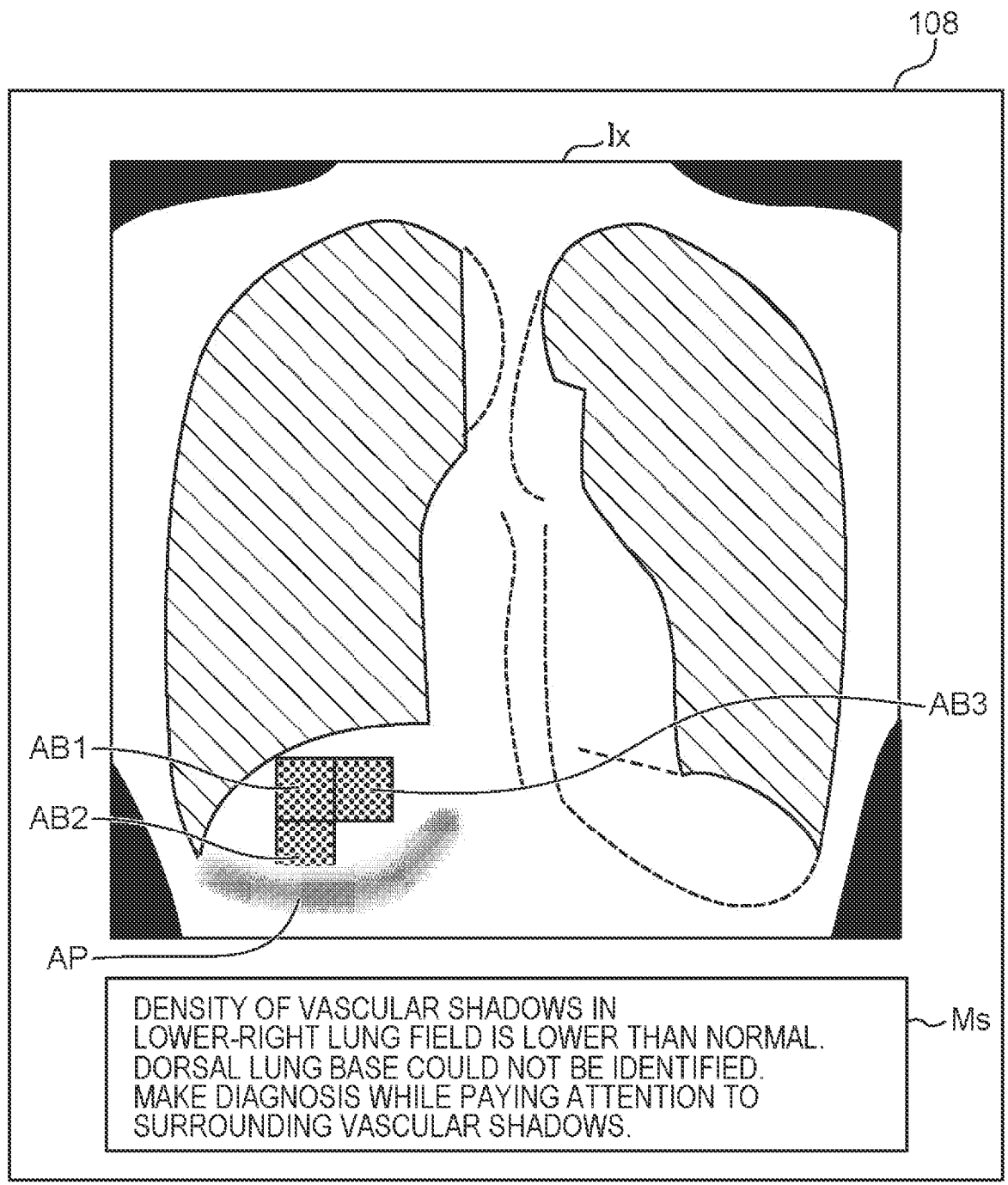
FIG. 35 is a diagram illustrating another example of the information displayed on the display.

FIG. 35 is a diagram schematically illustrating yet another example of the information displayed on the display 108. As described above, the lung area setting section 102 may calculate a degree of reliability indicating how probable a linear structure detected by the detection section 101 is. If the calculated degree of reliability is not higher than a certain threshold, the lung area setting section 102 may estimate another linear structure on the basis of a position of another certain anatomical structure detected by the detection section 101 and set a lung area using the estimated linear structure. In this case, a boundary of the set lung area might not be correct. As illustrated in FIG. 35, therefore, the display control section 122 may display, as the message Ms displayed on the display 108, a sentence indicating that an area to be processed has not been identified (i.e., an area to be processed is defined by the estimated linear structure) and that the user needs to take a careful look around a boundary of the area, as well as a sentence indicating details of an abnormal state.

In FIG. 35, as described with reference to FIG. 14, the area AP is an area where the possibility of presence of the right dorsal lung base is higher than or equal to the certain value, the possibility having been calculated from the right diaphragm dome shadow Px1 (e.g., FIG. 8) detected by the detection section 101 on the basis of the positional relationship between the right diaphragm dome shadow and the right dorsal lung base shadow. In the present embodiment, a blurred image having a certain degree of transparency, such as the area AP, is created for each of linear structures and saved in the memory 121 in advance. That is, data indicating a blurred image (the area AP illustrated in FIG. 35) for the right dorsal lung base and data indicating a blurred image (not illustrated) for the left dorsal lung base are saved in the memory 121 in advance. If a degree of reliability calculated by the lung area setting section 102 is lower than or equal to the certain threshold, the display control section 122 reads data indicating a blurred image from the memory 121. The display control section 122 displays the blurred image and a chest X-ray image on the display 108 while superimposing the blurred image upon the chest X-ray image through alpha blending.

Alternatively, the display control section 122 may also display, on the display 108, the estimated lower edge (FIG. 14) of the area AP indicating the right dorsal lung base shadow Px2. Alternatively, the display control section 122 may display the area AP (FIG. 35) on the display 108 if a degree of reliability of the right dorsal lung base shadow Px10 (e.g., FIG. 12) detected by the detection section 101 is higher than or equal to the threshold. Alternatively, the display control section 122 may allow the user to select whether to display the area AP (FIG. 35) on the display 108 using an operation panel (not illustrated) included in the abnormality display control apparatus 100.

Figure 36:
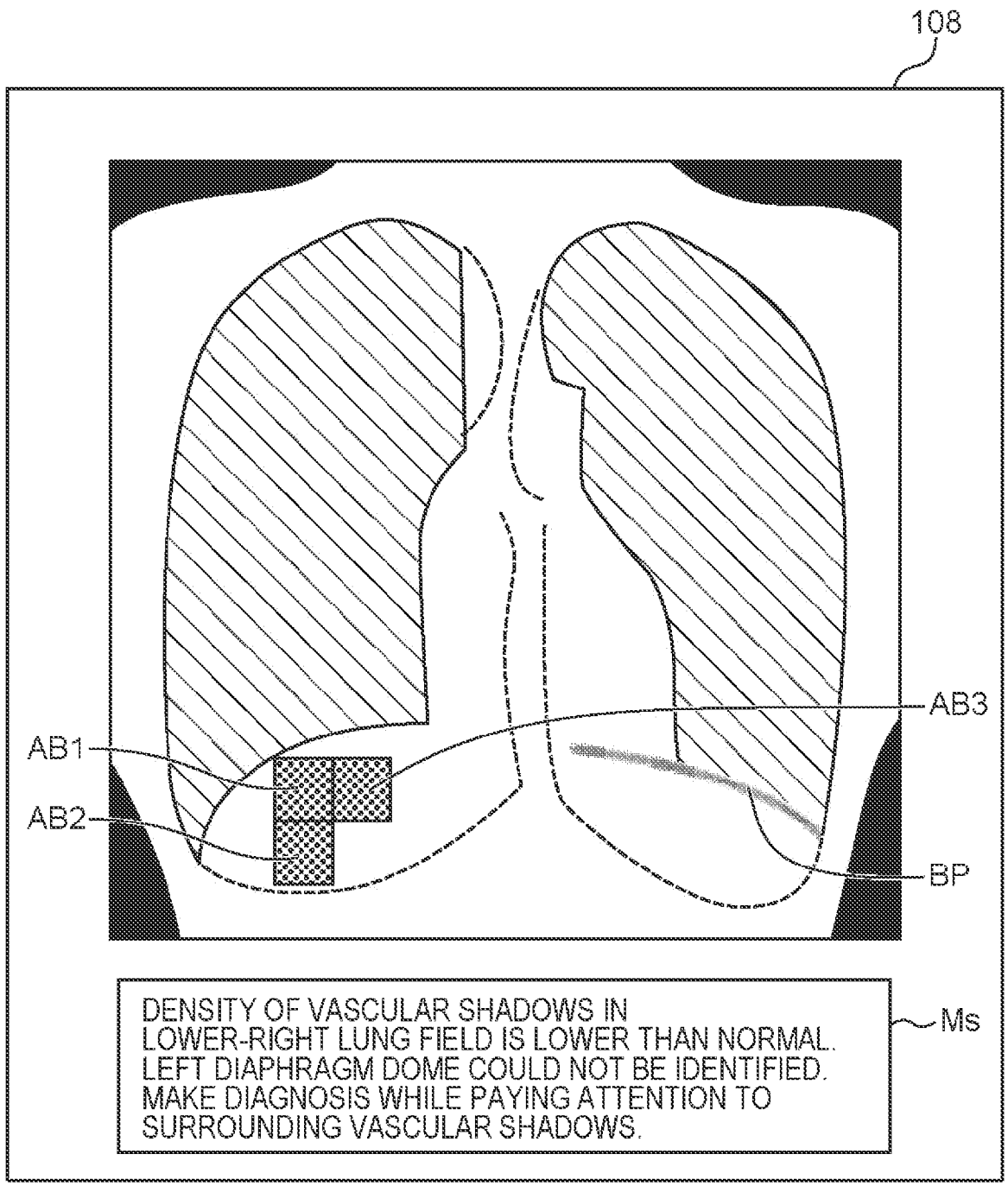
FIG. 36 is a diagram illustrating another example of the information displayed on the display.

FIG. 36 is a diagram schematically illustrating yet another example of the information displayed on the display 108. In the example illustrated in FIG. 36, for example, a positional relationship between the left diaphragm dome shadow and the left dorsal lung base shadow is obtained from a large number of normal cases and saved in the memory 121 in advance. In FIG. 36, an area BP is an area where a possibility of presence of the left diaphragm dome is higher than or equal to a certain value, the possibility having been obtained from the left dorsal lung base shadow Px10 (e.g., FIG. 12) detected by the detection section 101 on the basis of the positional relationship. The display control section 122 may also display an estimated upper edge of the area BP on the display 108.

As described above, according to the first embodiment of the present disclosure, whether there is an abnormality in an area in a chest X-ray image where one or more of the lungs and the heart overlap and an area in a chest X-ray image where one of the lungs and the liver overlap can be determined.

In addition, information indicating which and how local areas are different from normal states can be presented to the user, which is beneficial to the user. As a result, not only an interpreter but also a clinician or a radiologist can give a diagnosis or study by himself/herself, or a medical student can be educated or study by himself/herself.

In addition, since the areas RL1, RL2, LL1, and LL2 are divided into the local area RL21 and the other local areas as illustrated in FIG. 18, for example, the resolution of an area determined to be abnormal improves.

Modifications of First Embodiment

Although the areas RL1, RL2, LL1, and LL2 are divided into the local area RL21 and the other local areas as illustrated in FIG. 18, for example, and whether each of the local areas is in an abnormal state is determined in the first embodiment, a method used is not limited to this. For example, the abnormality determination section 104 may determine whether each of the areas RL1, RL2, LL1, and LL2 is in an abnormal state without dividing the areas RL1, RL2, LL1, and LL2, instead.

Figure 37:
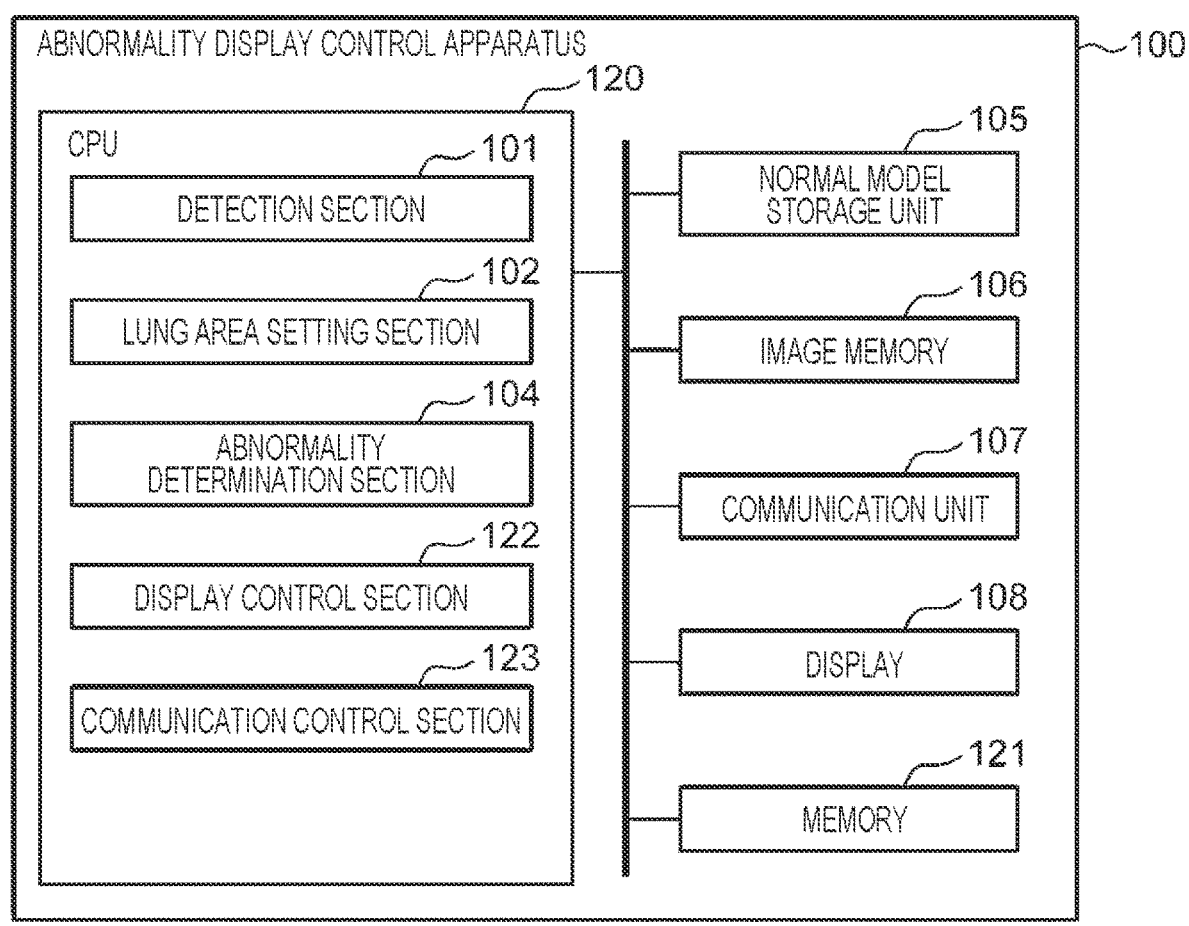
FIG. 37 is a block diagram of an abnormality display control apparatus having a configuration different from that illustrated in FIG. 1.

FIG. 37 is a block diagram illustrating an abnormality display control apparatus having a configuration different from that illustrated in FIG. 1. As illustrated in FIG. 37, an abnormality display control apparatus 100 (another example of the abnormality detection apparatus) includes a normal model storage unit 105, an image memory 106, a communication unit 107, a display 108, a CPU 120, and a memory 121. The abnormality display control apparatus 100 is achieved, for example, by a personal computer.

A ROM of the memory 121 stores a control program according to a modification of the first embodiment that causes the CPU 120 to operate. The CPU 120 executes the control program according to the modification of the first embodiment stored in the memory 121 to function as the detection section 101, the lung area setting section 102, the abnormality determination section 104, the display control section 122, and the communication control section 123. The CPU 120 thus does not include a local area setting section in the embodiment illustrated in FIG. 37.

The normal model storage unit 105 stores not reference indices of predefined local areas in the first embodiment but reference indices of the predefined areas RL1, RL2, LL1, and LL2. That is, in the embodiment illustrated in FIG. 37, a reference index is defined within a range of the diameter (i.e., thickness) of blood vessels or the density of blood vessels (i.e., a ratio of the area occupied by the blood vessels in an image to the area of a local area) included in each of the areas RL1, RL2, LL1, and LL2.

The abnormality determination section 104 extracts a vascular index indicating at least one of the thickness or density of pulmonary blood vessels from each of the areas RL1, RL2, LL1, and LL2. The abnormality determination section 104 determines whether each of the areas RL1, RL2, LL1, and LL2 is in an abnormal state by comparing the extracted vascular index with a reference index extracted from the normal model storage unit 105.

In the embodiment illustrated in FIG. 37, even if the area RL1, RL2, LL1, or LL2 is determined to be abnormal, a position in the area at which there is an abnormality is not identified. In the embodiment illustrated in FIG. 37, however, whether there is an abnormality in an area in a chest X-ray image where one or more of the lungs and the heart overlap and an area in a chest X-ray image where one of the lungs overlaps the diaphragm and the stomach can be determined as in the first embodiment.

Second Embodiment

Figure 38:
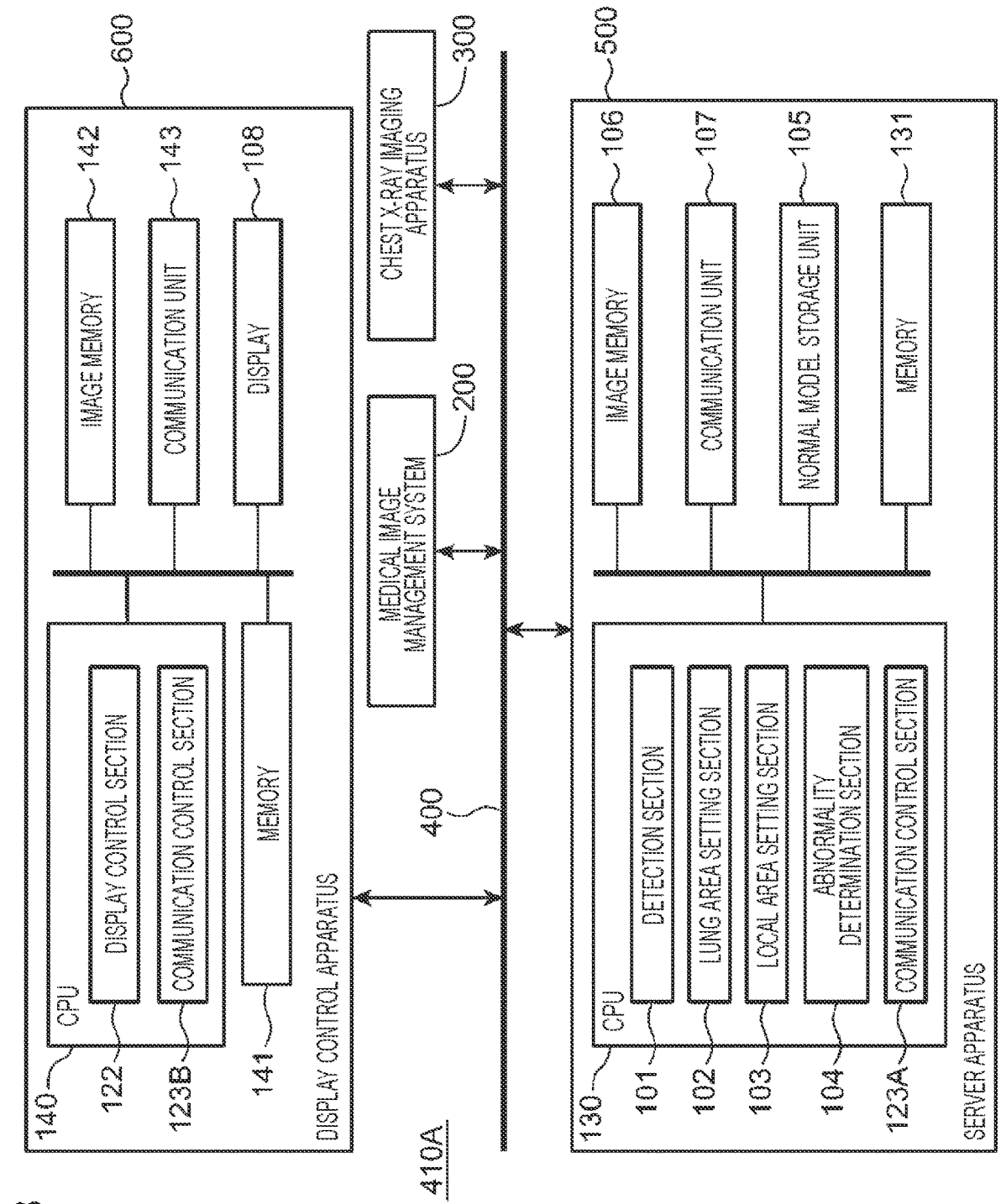
FIG. 38 is a block diagram of a network configuration in a medical facility according to a second embodiment.

FIG. 38 is a block diagram schematically illustrating a network configuration 410A in a medical facility according to a second embodiment. As illustrated in FIG. 38, a server apparatus 500, a display control apparatus 600, the medical image management system 200, and the chest X-ray imaging apparatus 300 are connected to an intranet 400 in the medical facility in the second embodiment.

The server apparatus 500, the display control apparatus 600, the medical image management system 200, and the chest X-ray imaging apparatus 300 need not necessarily be connected to the intranet 400 in the same medical facility. The display control apparatus 600 and the medical image management system 200 may be software operating on a data center server, a private cloud server, a public cloud server, or the like provided outside the medical facility.

As illustrated in FIG. 38, the server apparatus 500 includes the normal model storage unit 105, the image memory 106, the communication unit 107, a CPU 130, and a memory 131. The memory 131 is achieved, for example, by a semiconductor memory. The memory 131 includes, for example, a ROM, a RAM, or an EEPROM. The ROM of the memory 131 stores a control program for causing the CPU 130 to operate.

The CPU 130 executes the control program stored in the memory 131 to function as the detection section 101, the lung area setting section 102, the local area setting section 103, the abnormality determination section 104 (another example of the determiner), and a communication control section 123A (another example of the obtainer). The communication control section 123A obtains a target chest X-ray image from the medical image management system 200 through the communication unit 107 and saves the obtained target chest X-ray image in the image memory 106. The communication control section 123A transmits a result of detection performed by the detection section 101 and a result of a determination made by the abnormality determination section 104 to the display control apparatus 600 through the communication unit 107.

The display control apparatus 600 (an example of a terminal apparatus) is achieved, for example, by a tablet computer and carried by a medical worker such as a doctor or a radiologist. As illustrated in FIG. 38, the display control apparatus 600 includes a CPU 140, a memory 141, an image memory 142, a communication unit 143, and the display 108.

The memory 141 is achieved, for example, by a semiconductor memory. The memory 141 includes, for example, a ROM, a RAM, and an EEPROM. The ROM of the memory 141 stores a control program for causing the CPU 140 to operate. The CPU 140 executes the control program stored in the memory 141 to function as the display control unit 122 and a communication control unit 123B.

The communication control unit 123B receives, through the communication unit 143, data regarding a target chest X-ray image transmitted from the server apparatus 500 and stores the received data in the image memory 142. The communication control unit 123B also receives, through the communication unit 143, data regarding local areas determined to be in an abnormal state and a message indicating details of an abnormality transmitted from the server apparatus 500 and stores the received data and message in the memory 141. The display control unit 122 displays the same screen as in FIG. 34, 35, or 36 on the display 108 on the basis of the information transmitted from the server apparatus 500. According to the second embodiment, the same advantageous effects as those produced by the first embodiment can be produced. In the above embodiments, the local areas AB1, AB2, and AB3 determined to be in an abnormality state and the message Ms indicating details of an abnormality are an example of information indicating a result of a determination made by the abnormality determination section 104.

Other Embodiments (1) Although the lung area setting section 102 sets, in the chest X-ray image Ixp, the areas RL2 and LL1 where the lungs and the heart overlap, the area RL1 where one of the lungs overlaps the liver and the diaphragm, and the area LL2 where one of the lungs overlaps the diaphragm and the stomach in the above embodiments as illustrated in FIG. 16, for example, a method used is not limited to this. The lung area setting section 102 may set, in the chest X-ray image Ixp, one or both of the areas RL2 and LL1 where the lungs and the heart overlap, the area RL1 where one of the lungs overlaps the liver and the diaphragm, and the area LL2 where one of the lungs overlap the diaphragm and the stomach, instead. That is, it is only required that the lung area setting section 102 set, in the chest X-ray image Ixp, at least one of the areas RL2 and LL1 where the lungs and the heart overlap, the area RL1 where one of the lungs overlaps the liver and the diaphragm, and the area LL2 where one of the lungs overlaps the diaphragm and the stomach.

(2) Although the display control section 122 displays, on the display 108, local areas determined to be in an abnormal state and details of an abnormality in the above embodiments as illustrated in FIG. 34, for example, a method used is not limited to this. The display control section 122 (an example of an output controller) may output local areas determined to be in an abnormal state and details of an abnormality to a memory removably attached to the abnormality display control apparatus 100, instead. The removably attached memory may be, for example, a universal serial bus (USB) memory, a compact disc-recordable (CD-R), a compact disc-rewritable (CD-RW), or a digital versatile disc-recordable (DVD-R). In this embodiment, too, useful information can be provided for the user.

(3) In the above embodiments, the probability density function PDF (FIG. 30) of an index, for example, is saved in the normal model storage unit 105 as a reference index. Alternatively, thresholds for an index may be saved in the normal model storage unit 105 as a reference index. The thresholds for an index are, for example, a first value TH1 and a second value TH2 shown in the horizontal axis in FIG. 30. In this case, if an index P is TH1≤P≤TH2, the abnormality determination section 104 determines that a corresponding local area is probably normal, and if the index P is P<TH1 or TH2<P, the abnormality determination section 104 determines that the corresponding local area is probably abnormal.

(4) In the above embodiments, the display control section 122 may display the index extracted in step S500 on the display 108 or output the index extracted in step S500 to the removably attached memory, instead of performing step S600, S700, S800, and S900 illustrated in FIG. 3. According to this embodiment, the index extracted in step S500 can be provided for the user. As a result, the user can use the index extracted in step S500. For example, the user can understand a state of pulmonary blood vessels in a local area in a chest X-ray image with an objective value using the index extracted in step S500. The user, therefore, can more accurately determine whether the state of the pulmonary blood vessels is abnormal.

The present disclosure can be used in diagnosis aiding systems for chest X-ray images to be interpreted and interpretation education systems for medical students or interns.

What is claimed is:

1. A method for detecting an abnormality, the method comprising:
    obtaining, using a computer, a chest X-ray image;
    detecting, in the obtained chest X-ray image using the computer and a model constructed through machine learning before the detecting, boundary lines of images of anatomical structures whose ranges of X-ray transmittances are different from one another;
    setting, using the computer, a third lung area in the chest X-ray image including at least one of a first lung area where one or more lungs and a heart overlap or a second lung area where one of the lungs and a liver overlap on a basis of the detected boundary lines;
    extracting, using the computer, a vascular index indicating at least one of thickness or density of at least one pulmonary blood vessel present in an area included in the third lung area;
    determining, using the computer, whether the area included in the third lung area is in an abnormal state on a basis of the vascular index and a reference index based on indices extracted, using a method used to extract the vascular index, in advance from an area in chest X-ray images in a normal state corresponding to the area included in the third lung area; and
    outputting, if it is determined that the area included in the third lung area is in an abnormal state, information indicating a result of the determining using the computer.

2. The method according to claim 1,
    wherein, in the detecting, boundary lines of at least two of a left ventricle shadow, a descending aorta shadow, a left diaphragm dome shadow, a left edge of a vertebral body, a right edge of the vertebral body, a right atrium shadow, and a right diaphragm dome shadow are detected, and
    wherein, in the setting, the third lung area including the first lung area is set, the first lung area being set as one or more areas, each of which is sandwiched by at least two of the boundary lines detected in the detecting.

3. The method according to claim 2,
wherein, in the detecting, boundary lines of at least the left ventricle shadow, the descending aorta shadow, the left diaphragm dome shadow, the right edge of the vertebral body, and the right atrium shadow are detected among boundary lines of the left ventricle shadow, the descending aorta shadow, the left diaphragm dome shadow, the left edge of the vertebral body, the right edge of the vertebral body, the right atrium shadow, and the right diaphragm dome shadow, and
wherein, in the setting, the first lung area is set as an area sandwiched by, among the boundary lines detected in the detecting, the boundary lines of the left ventricle shadow, the descending aorta shadow, and the left diaphragm dome shadow and an area sandwiched by the boundary lines of the right edge of the vertebral body and the right atrium shadow.

4. The method according to claim 2,
wherein, in the detecting, boundary lines of at least the left edge of the vertebral body, the left ventricle shadow, the left diaphragm dome shadow, the right edge of the vertebral body, and the right atrium shadow are detected among boundary lines of the left ventricle shadow, the descending aorta shadow, the left diaphragm dome shadow, the left edge of the vertebral body, the right edge of the vertebral body, the right atrium shadow, and the right diaphragm dome shadow, and
wherein, in the setting, the first lung area is set as an area sandwiched by, among the boundary lines detected in the detecting, the boundary lines of the left edge of the vertebral body, the left ventricle shadow, and the left diaphragm dome shadow and an area sandwiched by the boundary lines of the right edge of the vertebral body and the right atrium shadow.

5. The method according to claim 2,
wherein, in the setting, the first lung area is set as one or more closed areas defined by the boundary lines detected in the detecting and interpolation lines connecting adjacent ones of the boundary lines to each other.

6. The method according to claim 1,
wherein, in the detecting, boundary lines of at least two of a right diaphragm dome shadow, a right dorsal lung base shadow, and a right edge of a vertebral body are detected, and
wherein, in the setting, the third lung area including the second lung area is set, the second lung area being set as an area sandwiched by at least two of the boundary lines detected in the detecting.

7. The method according to claim 6,
wherein, in the detecting, the boundary lines of at least the right diaphragm dome shadow and the right dorsal lung base shadow are detected among the boundary lines of the right diaphragm dome shadow, the right dorsal lung base shadow, and the right edge of the vertebral body, and
wherein, in the setting, the second lung area is set as an area sandwiched by, among the boundary lines detected in the detecting, the boundary lines of the right diaphragm dome shadow and the right dorsal lung base shadow.

8. The method according to claim 6,
wherein, in the detecting, the boundary lines of the right diaphragm dome shadow, the right dorsal lung base shadow, and the right edge of the vertebral body are detected, and
wherein, in the setting, the second lung area is set as an area sandwiched by the boundary lines of the right diaphragm dome shadow, the right dorsal lung base shadow, and the right edge of the vertebral body detected in the detecting.

9. The method according to claim 6,
wherein, in the setting, the second lung area is set as a closed area defined by the boundary lines detected in the detecting and interpolation lines connecting adjacent ones of the boundary lines to each other.

10. The method according to claim 6, further comprising:
calculating, if a boundary line of the right dorsal lung base shadow is detected in the detecting, a degree of reliability indicating how probable a result of the detecting of the boundary line of the right dorsal lung base shadow is using the computer; and
estimating, if the degree of reliability is lower than or equal to a first threshold, the boundary line of the right dorsal lung base shadow on a basis of a position of at least one of the boundary lines detected in the detecting other than the boundary line of the right dorsal lung base shadow using the computer;
wherein, if the degree of reliability is higher than the first threshold in the setting of the second lung area, the boundary line of the right dorsal lung base shadow detected in the detecting is used and, if the degree of reliability is lower than or equal to the first threshold, the boundary line of the right dorsal lung base shadow estimated in the estimating is used.

11. The method according to claim 10,
wherein, if the boundary line of the right dorsal lung base shadow estimated in the estimating is used in the setting of the second lung area, information for calling attention to an area including a right lung base is output in the outputting.

12. The method according to claim 1,
wherein the third lung area further includes a fourth lung area located below the first lung area, and
wherein, in the detecting, a boundary line of a left dorsal lung base shadow is detected as one of the boundary lines.

13. The method according to claim 12,
wherein, in the detecting, at least two boundary lines including the boundary line of the left dorsal lung base shadow are detected among boundary lines of a left diaphragm dome shadow, the left dorsal lung base shadow, and a left edge of a vertebral body, and
wherein, in the setting, the third lung area including the fourth lung area is set, the fourth lung area being set as an area sandwiched by at least two of the boundary lines detected in the detecting.

14. The method according to claim 12,
wherein, in the detecting, the boundary lines of at least the left diaphragm dome shadow and the left dorsal lung base shadow are detected among the boundary lines of the left diaphragm dome shadow, the left dorsal lung base shadow, and the left edge of the vertebral body, and
wherein, in the setting, the fourth lung area is set as an area sandwiched by, among the boundary lines detected in the detecting, the boundary lines of the left diaphragm dome shadow and the left dorsal lung base shadow.

15. The method according to claim 12,
wherein, in the detecting, boundary lines of a left diaphragm dome shadow, the left dorsal lung base shadow, and a left edge of a vertebral body are detected, and wherein, in the setting, the fourth lung area is set as an area sandwiched by the boundary lines of the left diaphragm dome shadow, the left dorsal lung base shadow, and the left edge of the vertebral body detected in the detecting.

16. The method according to claim 13,
wherein, in the setting, the fourth lung area is set as a closed area defined by the boundary lines detected in the detecting and interpolation lines connecting adjacent ones of the boundary lines to each other.

17. The method according to claim 13, further comprising:
calculating, using the computer, a degree of reliability indicating how probable a result of the detecting of the boundary line of the left dorsal lung base shadow is; and
estimating, if the degree of reliability is lower than or equal to a second threshold, the boundary line of the left dorsal lung base shadow on a basis of a position of at least one of the boundary lines detected in the detecting other than the boundary line of the left dorsal lung base shadow using the computer,
wherein, if the degree of reliability is higher than the second threshold in the setting of the fourth lung area, the boundary line of the left dorsal lung base shadow detected in the detecting is used and, if the degree of reliability is lower than or equal to the second threshold, the boundary line of the left dorsal lung base shadow estimated in the estimating is used.

18. The method according to claim 17,
wherein, if the boundary line of the left dorsal lung base shadow estimated in the estimating is used in the setting of the fourth lung area, information for calling attention to an area including a left lung base is output in the outputting.

19. The method according to claim 1,
wherein, in the outputting, an image of the area included in the third lung area determined to be in the abnormal state and details of the abnormal state of the area included in the third lung area are output and displayed on a display as information indicating a result of the determining.

20. The method according to claim 19, further comprising:
dividing, using the computer, the third lung area set in the setting into local areas 1 to n, each of which includes the area included in the third lung area, n being a natural number greater than or equal to 2,
wherein, in the extracting, a vascular index i indicating at least one of thickness or density of at least one pulmonary blood vessel present in a local area i is extracted as the vascular index, i being a natural number greater than or equal to 1 and less than or equal to n,
wherein, in the determining, whether the local area i is in an abnormal state is determined on a basis of the vascular index i and a reference index i based on indices extracted, using a method used to extract the vascular index i, in advance from an area in chest X-ray images in a normal state corresponding to the local area i, and
wherein, in the outputting, an image of a local area j determined to be in an abnormal state and details of the abnormal state of the local area j are displayed on the display, j being a natural number greater than or equal to 1 and less than or equal to n.

21. The method according to claim 20, further comprising:
generating, using the computer, groups 1 to m including different ones of the local areas 1 to n in accordance with two-dimensional distances from hila in the obtained chest X-ray image, m being a natural number greater than or equal to 2,
wherein, in the extracting, a vascular index k indicating at least one of thickness or density of at least one pulmonary blood vessel present in a group k is extracted as the vascular index, k being a natural number greater than or equal to 1 and less than or equal to m,
wherein, in the determining, whether the group k is in an abnormal state is determined on a basis of the vascular index k and a reference index k based on indices extracted, using a method used to extract the vascular index k, in advance from an area in chest X-ray images in a normal state corresponding to the group k, and
wherein, in the outputting, an image of a group h determined to be in an abnormal state and details of the abnormal state of the group h are displayed on the display, h being a natural number greater than or equal to 1 and less than or equal to m.

22. The method according to claim 1,
wherein the model is obtained by performing, using training chest X-ray images, which are the chest X-ray images in the normal state, as input data and images indicating boundary lines in the training chest X-ray images as training data, the machine learning on a basis of a neural network that makes predictions in units of pixels such that the boundary lines are detected from the training chest X-ray images.

23. The method according to claim 1,
wherein the reference index is a threshold set in advance for a probability density function of indices extracted, using the method used to extract the vascular index, in advance from the area in the chest X-ray images in the normal state corresponding to the area included in the third lung area or the indices extracted, using the method used to extract the vascular index, in advance from the area in the chest X-ray images in the normal state corresponding to the area included in the third lung area.

24. A non-transitory computer-readable recording medium storing a program for detecting an abnormality that causes a computer to function as:
an obtainer that obtains a chest X-ray image;
a detector that detects, in the obtained chest X-ray image, boundary lines of images of anatomical structures whose ranges of X-ray transmittances are different from one another using a model constructed through machine learning before the detection;
a setter that sets a third lung area in the chest X-ray image including at least one of a first lung area where one or more lungs and a heart overlap or a second lung area where one of the lungs and a liver overlap on a basis of the detected boundary lines;
a determiner that extracts a vascular index indicating at least one of thickness or density of at least one pulmonary blood vessel present in an area included in the third lung area and that determines whether the area included in the third lung area is in an abnormal state on a basis of the extracted vascular index and a reference index based on indices extracted, using a method used to extract the vascular index, in advance from an area in chest X-ray images in a normal state corresponding to the area included in the third lung area; and an output controller that outputs, if it is determined that the area included in the third lung area is in an abnormal state, information indicating a result of the determination made by the determiner.

25. An abnormality detection apparatus comprising:
an obtainer that obtains a chest X-ray image;
a detector that detects, in the obtained chest X-ray image, boundary lines of images of anatomical structures whose ranges of X-ray transmittances are different from one another using a model constructed through machine learning before the detection;
a setter that sets a third lung area in the chest X-ray image including at least one of a first lung area where one or more lungs and a heart overlap or a second lung area where one of the lungs and a liver overlap on a basis of the detected boundary lines;
a determiner that extracts a vascular index indicating at least one of thickness or density of at least one pulmonary blood vessel present in an area included in the third lung area and that determines whether the area included in the third lung area is in an abnormal state on a basis of the extracted vascular index and a reference index based on indices extracted, using a method used to extract the vascular index, in advance from an area in chest X-ray images in a normal state corresponding to the area included in the third lung area; and
an output controller that outputs, if it is determined that the area included in the third lung area is in an abnormal state, information indicating a result of the determination made by the determiner.

26. A server apparatus comprising:
an obtainer that obtains a chest X-ray image;
a detector that detects, in the obtained chest X-ray image, boundary lines of images of anatomical structures whose ranges of X-ray transmittances are different from one another using a model constructed through machine learning before the detection;
a setter that sets a third lung area in the chest X-ray image including at least one of a first lung area where one or more lungs and a heart overlap or a second lung area where one of the lungs and a liver overlap on a basis of the detected boundary lines;
a determiner that extracts a vascular index indicating at least one of thickness or density of at least one pulmonary blood vessel present in an area included in the third lung area and that determines whether the area included in the third lung area is in an abnormal state on a basis of the extracted vascular index and a reference index based on indices extracted, using a method used to extract the vascular index, in advance from an area in chest X-ray images in a normal state corresponding to the area included in the third lung area; and
an output controller that outputs, if it is determined that the area included in the third lung area is in an abnormal state, information indicating a result of the determination made by the determiner.

27. A method for detecting an abnormality, the method comprising:
obtaining, using a computer, a chest X-ray image;
determining, using the computer, whether an area included in a third lung area in the obtained chest X-ray image including a first lung area where one or more lungs and a heart overlap and/or a second lung area where one of the lungs and a liver overlap is in an abnormal state; and
outputting, if determining that the area included in the third lung area is in an abnormal state, information indicating that the area included in the third lung area is abnormal using the computer.

28. The method according to claim 27, further comprising:
detecting, in the obtained chest X-ray image using the computer, a first boundary line between an image of the one or more lungs and an image of the heart and/or a second boundary line between an image of one of the lungs and an image of the liver;
setting, using the computer, the third lung area in the obtained chest X-ray image on a basis of the first boundary line and/or the second boundary line; and
extracting, using the computer, a vascular index indicating density of at least one blood vessel in the area included in the third lung area,
wherein, in the determining, whether the area included in the third lung area is in an abnormal state is determined on a basis of the vascular index and a reference index indicating density of at least one blood vessel in an area in chest X-ray images in a normal state corresponding to the area included in the third lung area.

29. A method for processing information, the method comprising:
obtaining, using a computer, a chest X-ray image;
detecting, in the obtained chest X-ray image using the computer and a model constructed through machine learning before the detecting, boundary lines of images of anatomical structures whose ranges of X-ray transmittances are different from one another;
setting, using the computer, a third lung area in the chest X-ray image including at least one of a first lung area where one or more lungs and a heart overlap or a second lung area where one of the lungs and a liver overlap on a basis of the detected boundary lines;
extracting, using the computer, a vascular index indicating at least one of thickness or density of at least one pulmonary blood vessel present in an area included in the third lung area; and
outputting, using the computer, the extracted vascular index.

30. The method according to claim 1,
wherein the first lung area is a first area where a left lung included in the lungs and the heart overlap, a second area where a right lung included in the lungs and the heart overlap, or both the first area and the second area.

* * * * *

UNITED STATES PATENT AND TRADEMARK OFFICE
CERTIFICATE OF CORRECTION

PATENT NO. : 11,935,234 B2
APPLICATION NO. : 17/492732
DATED : March 19, 2024
INVENTOR(S) : Kenji Kondo et al.

Page 1 of 1

It is certified that error appears in the above-identified patent and that said Letters Patent is hereby corrected as shown below:

On the Title Page

In item (73) Assignee: replace "PANASONIC CORPORATION, Osaka (JP)" with
-- PANASONIC HOLDINGS CORPORATION, Osaka (JP) --.

Signed and Sealed this
Twenty-third Day of July, 2024

Katherine Kelly Vidal
*Director of the United States Patent and Trademark Office*